US011884666B2

(12) United States Patent
Ellis et al.

(10) Patent No.: US 11,884,666 B2
(45) Date of Patent: Jan. 30, 2024

(54) AZABICYCLO AND DIAZEPINE DERIVATIVES

(71) Applicant: Alcon Inc., Fribourg (CH)

(72) Inventors: David Ellis, Durham, NC (US); Howard Allen Ketelson, Dallas, TX (US)

(73) Assignee: Alcon Inc., Fribourg (CH)

( * ) Notice: Subject to any disclaimer, the term of this patent is extended or adjusted under 35 U.S.C. 154(b) by 18 days.

(21) Appl. No.: 17/699,606

(22) Filed: Mar. 21, 2022

(65) Prior Publication Data

US 2022/0267328 A1 Aug. 25, 2022

Related U.S. Application Data

(62) Division of application No. 16/760,192, filed as application No. PCT/IB2018/058631 on Nov. 2, 2018, now Pat. No. 11,306,090.

(60) Provisional application No. 62/749,610, filed on Oct. 23, 2018, provisional application No. 62/581,073, filed on Nov. 3, 2017.

(51) Int. Cl.
| | |
|---|---|
| *C07D 471/08* | (2006.01) |
| *A61P 27/10* | (2006.01) |
| *A61K 9/00* | (2006.01) |
| *C07D 243/38* | (2006.01) |
| *C07D 471/04* | (2006.01) |

(52) U.S. Cl.
CPC .......... *C07D 471/08* (2013.01); *A61K 9/0048* (2013.01); *A61P 27/10* (2018.01); *C07D 243/38* (2013.01); *C07D 471/04* (2013.01)

(58) Field of Classification Search
CPC ...... C07D 471/08; A61K 9/0048; A61P 27/10
See application file for complete search history.

(56) References Cited

U.S. PATENT DOCUMENTS 7,585,974 B2  9/2009 Galli et al.

FOREIGN PATENT DOCUMENTS

| CN | 1583744 A | 2/2005 | |
|---|---|---|---|
| EA | 007793 B1 | 2/2007 | |
| EP | 2657234 A1 | 10/2013 | |
| RU | 2591701 C2 | 7/2016 | |
| WO | WO 02/096418 * | 12/2002 | ............. A61K 31/42 |

OTHER PUBLICATIONS

Toda et al., Corner. 15(2): 120-128, Mar. 1996 (Abstract Only).*
G. M. Dyson, P. May, "May's Chemistry of Synthetic Drugs", London: Longmans, Green and Co., 1959, Moscow: Mir, 1964, pp. 12-19.
K. Kummerer, "Pharmaceuticals in the environment, Annual Review of Environment and Resources", 2010, vol. 35, pp. 57-75.
Kharkevich, D.A., "Farmakologiya" (Pharmacology: A Handbook), 10th Ed., 2010, pp. 72-82.
Koretskaya N. I. et al., "Synthesis and pharmacologic study of the tropine esters of a-substituted tropic acids", Khimiko-Farmatsevticheskii Zhurnal (1972), 6(7), pp. 3-8.
Mashkovsky M. D. et al., "Antihistamine and antiserotoinin properties of new tropine esters", Farmakologiya i Toksikologiya (Moscow) (1979), 42(1), pp. 3-7.
Mashkovsky M.D, "Medicaments" (Lekarstvennye Sredstva), 14th ed., Moscow, 2001, vol. 1, p. 11.
Perederiy, V.A., "Glaznyye bolezni. Polnyy spravochnik" (Eye diseases. Complete Reference, Moscow: Eksmo, 2008, pp. 13, 4th paragraph, pp. 81-85).
PubChem CID 100075964 , entered into PubChem Dec. 11, 2015.
PubChem CID 11859594, entered into PubChem Nov. 9, 2006.
PubChem CID 11859595, entered into PubChem Nov. 9, 2006.
PubChem CID 124919201, entered into PubChem Apr. 10, 2017.
PubChem CID 124919202, entered into PubChem Apr. 10, 2017.
PubChem CID 3428362 , CAS RN 402846-42-8, 9-methyl-9-azabicyclo[4.2.1]nonan-3-yl) 3-hydroxy-2-phenylpropanoate, entered into PubChem Sep. 8, 2005, and isomers thereof.
PubChem CID 51414129, entered into PubChem May 20, 2011.
PubChem CID 98052117, entered into PubChem Dec. 11, 2015.
Ting-Chao Chou, "Drug Combination Studies and Their Synergy Quantification Using the Chou-Talalay Method", Cancer Res. 70(2), 2010, pp. 440-446.
V. G. Belikov, "Farmatsevticheskaya Khimiya" (Pharmaceutical Chemistry: A Scholar Manual), Moscow: MEDpress-Inform, 2007, pp. 27-29.
Vengerovskiy, A.I.,Фармакоl огическа я несовмес тимость "(Pharmacological incompatibility),Бюлл етень сиби рской меди цины (Bulletin of Siberian Medicine), No. 3, 2003, pp. 49-56.
Tatham, Peter E. R., et al. "The Practice of Medicinal Chemistry", The Netherlands, Elsevier Science, 2009, pp. 310-313 section 2. Carboxylic esters bioisosteres.

* cited by examiner

*Primary Examiner* — Alicia L Otton

(74) *Attorney, Agent, or Firm* — Jian Zhou

(57) ABSTRACT

The present invention provides in one aspect azabicyclo and diazepine derivatives useful as modulators of muscarinic receptors. In another aspect, the present invention provides pharmaceutical compositions for treating ocular diseases, the compositions comprising at least one muscarinic receptor modulator.

13 Claims, 33 Drawing Sheets

AZABICYCLO AND DIAZEPINE DERIVATIVES

FIELD OF THE INVENTION

The present invention relates to azabicyclo and diazepine derivatives useful as modulators of muscarinic receptors and methods of treating disease using same.

BACKGROUND OF THE INVENTION

The muscarinic receptor is a target for the excitatory neurotransmitter acetylcholine, and was named based on the selective activation of the receptor by muscarine. The muscarinic receptor is widely distributed throughout human tissues, and is further classified into subtypes of M1 to M5. The modulation of muscarinic receptors has been considered a therapeutic target for disorders ranging from overactive bladder to cognitive disorders (Abrams et al., *Br. J Pharmacol* 2006 July; 148(5): 565-578).

Myopia is an ocular refractive error caused by excessive growth of the eye in a longitudinal direction. This elongation of the eye causes the visual image to be focused in front of the retina and typically results in blurred vision of distant objects. The non-selective muscarinic antagonist atropine has been reported to be effective as a topical 1% drop in the treatment of myopia. (Chua et al., *Ophthalmology* 2006 December; 113(12):2285-91). However, numerous side effects were reported, including mydriasis (dilation of the pupil) and blurring of near vision due to cycloplegia (inability to accommodate). Presently, corrective lenses represent the primary means for ameliorating eye-length disorders such as myopia. However, lenses optically correct the refractive errors without treating the underlying cause which is excessive growth of the eye. Thus, there remains a need for methods to treat disorders relating to excessive growth of the eye.

SUMMARY OF THE INVENTION

There remains a need for new treatments and therapies for excessive growth of the eye. The invention provides compounds, pharmaceutically acceptable salts thereof, pharmaceutical compositions thereof and combinations thereof, which compounds are muscarinic modulators. The invention further provides methods of treating, preventing, or ameliorating disorders relating to excessive growth of the eye, comprising administering to a subject in need thereof an effective amount of a muscarinic modulator. Various embodiments of the invention are described herein.

Within certain aspects, provided herein is a compound of formula (I) or (II) or a pharmaceutically acceptable salt thereof:

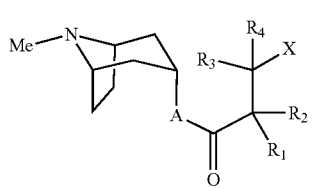

(I)

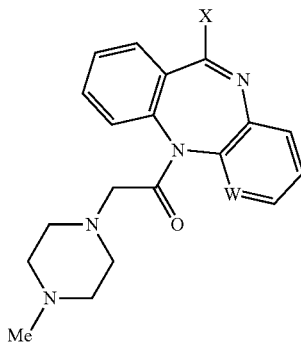

(II)

wherein
Me=$CH_3$;
A=O or $NR_5$;
W=N or CH;
X=—OH, —O—Y—Z, —S—Y—Z, or —$NR_5$—Y—Z;
$R_1$ and $R_2$ are independently substituted as H, D, hydroxyl, alkoxy, nitrile, halogen atoms, $C_1$-$C_{20}$ (preferably $C_1$-$C_{10}$) straight, branched or cyclo alkyl groups optionally substituted with halogen atoms; or
$R_1$ and $R_2$ are independently substituted as phenyl or benzyl groups being optionally substituted with one or more substituents selected from $C_1$-$C_{20}$ (preferably $C_1$-$C_{10}$) straight, branched or cyclo alkyl groups, halo alkyl groups, hydroxyl, alkoxy, nitrile, nitro, amino, amide, ester, sulfone, sulfoxide, sulfonamide, and halogen atoms; or
$R_1$ and $R_2$ are independently substituted with a heterocyclic saturated, unsaturated or aromatic 5- or 6-member ring containing one or more heteroatoms selected from nitrogen, oxygen and sulfur and being optionally substituted with one or more substituents selected from $C_1$-$C_{20}$ (preferably $C_1$-$C_{10}$) straight, branched or cyclo alkyl, halo alkyl groups, hydroxyl, alkoxy, nitrile, nitro, amino, amide, ester, sulfone, sulfoxide or halogen atoms;
$R_3$ and $R_4$ are independently substituted with hydrogen, $C_1$-$C_{10}$ straight or branched or cyclo alkyl or halo alkyl groups or
$R_3$ and $R_4$ can combine to form 3- to 6-membered rings;
$R_5$=H or $C_1$-$C_{20}$, preferably $C_1$-$C_{10}$, straight or branched alkyl groups, $C_1$-$C_{10}$ straight or branched haloalkyl groups;
Y is a bivalent radical having the following meaning:
a) Straight or branched $C_1$-$C_{20}$ (preferably $C_1$-$C_{10}$) alkyl, being optionally substituted with one or more of the substituents selected from the group consisting of: halogen atoms and hydroxyl;
b) —C(O)($C_1$-$C_{10}$ alkyl)- or —C(O)($CH_2$)$_n$C(O)O—($C_1$-$C_{10}$ alkyl)- or —($C_1$-$C_{10}$ alkyl)-;

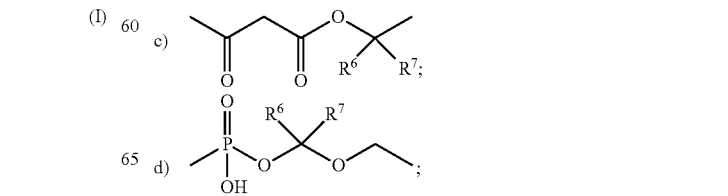

-continued

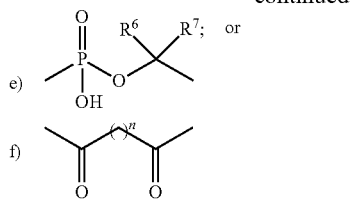

e)

f)

wherein n is an integer from 0 to 20;

$R^6$ and $R^7$ are independently H or $C_1$-$C_{10}$, straight or branched alkyl groups, $C_1$-$C_{10}$ straight or branched haloalkyl groups; or $R^6$ and $R^7$ can combine to form 3- to 6-membered rings; and Z is H, —OH, $C_{1-6}$ alkoxy, —COOH, —$NR^8R^9$;

$R^8$ and $R^9$ are independently substituted as $C_1$-$C_{20}$ alkyl, preferably $C_1$-$C_{10}$, being optionally substituted with one or more substituents selected from hydroxyl, amino, ester, carboxylic acid, and halogen atoms; or $R^8$ and $R^9$ can combine to form 3- to 6-membered rings containing one or more heteroatoms which are selected from the group consisting of:

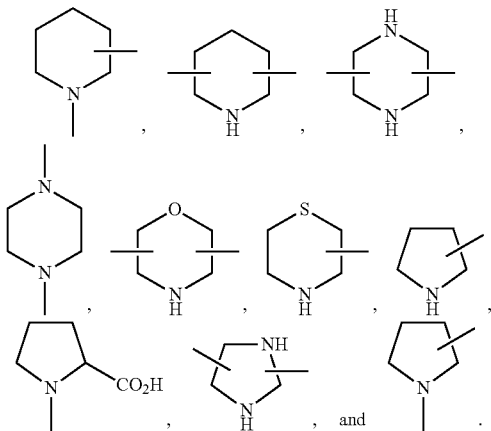

In another aspect, the invention provides a pharmaceutical composition comprising: (1) a therapeutically effective amount of (preferably from about 0.01 to about 10.0 weight percent of, more preferably from about 0.01 to about 5 weight/volume percent of or from about 0.1 to 5.0 weight percent of) (a) a compound of the present invention and/or (b) a pharmaceutically acceptable salt thereof; and (2) one or more pharmaceutically acceptable carriers. In yet another aspect, the invention provides a pharmaceutical composition comprising: (1) a compound of the present invention and/or a pharmaceutically acceptable salt thereof; and (2) one or more pharmaceutically acceptable carriers.

In another aspect, the invention provides a combination, in particular a pharmaceutical combination, comprising: (1) a therapeutically effective amount of (preferably from about 0.01 to about 10.0 weight percent, more preferably from about 0.01 to about 5 weight/volume percent of or from about 0.1 to 5.0 weight percent of) (a) a compound of the present invention and/or (b) a pharmaceutically acceptable salt thereof; and (2) one or more therapeutically active agents. In yet another aspect, the invention provides a combination, in particular a pharmaceutical combination, comprising: (1) a compound of the present invention and/or a pharmaceutically acceptable salt thereof; and (2) one or more therapeutically active agents.

Specific preferred embodiments of the invention will become evident from the following more detailed description of certain preferred embodiments and the claims.

DETAILED DESCRIPTION OF THE INVENTION

Figure 1:
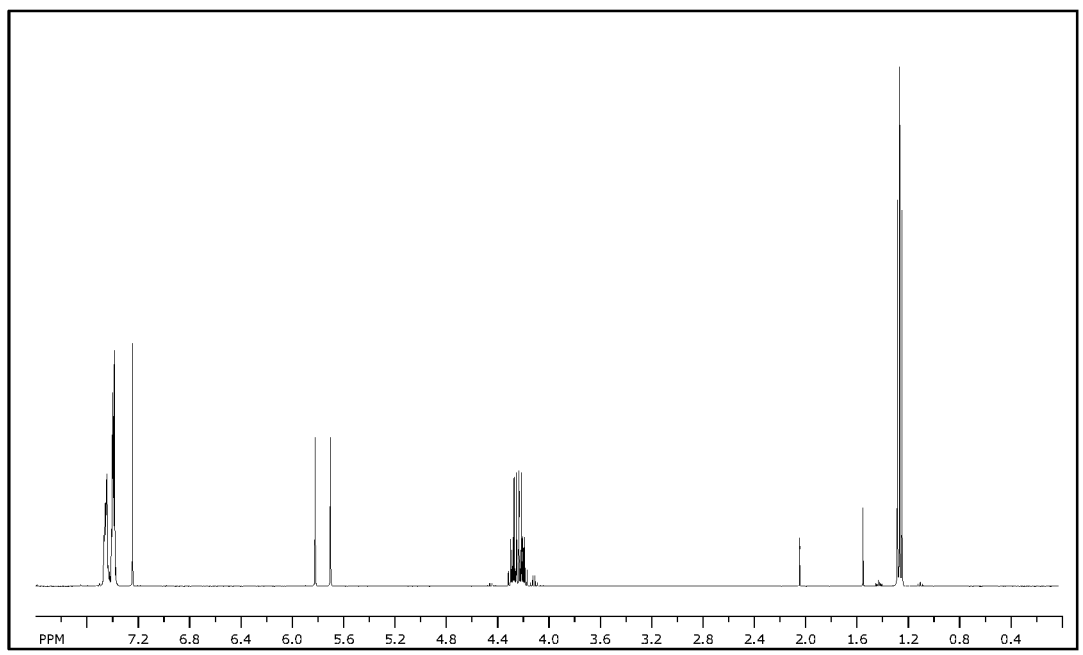
FIG. 1 is a $^1$H NMR spectrum of ethyl 2-fluoro-2-phenylacetate.

The invention relates to classes of compounds each having an atropine or pirenzepine residue and pharmaceutically acceptable salts thereof. In preferred embodiments, the invention provides a compound of formula (I) or (II) or a pharmaceutically acceptable salt thereof:

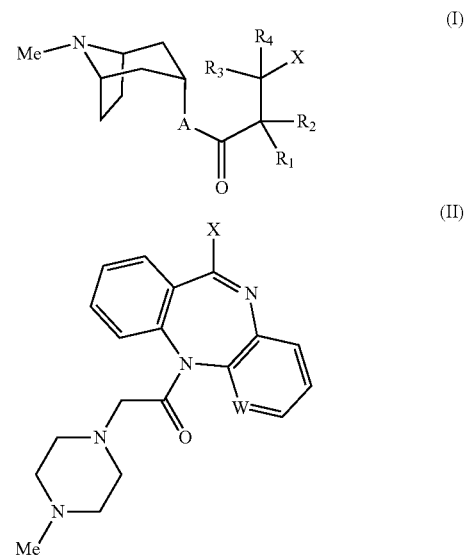

wherein
Me=CH₃;
A=O or NR₅;
W=N or CH;
X=—OH, —O—Y—Z, —S—Y—Z, or —NR₅—Y—Z;
R₁ and R₂ are independently substituted as H, D, hydroxyl, alkoxy, nitrile, halogen atoms, C₁-C₂₀ (preferably C₁-C₁₀) straight, branched or cyclo alkyl groups optionally substituted with halogen atoms; or
R₁ and R₂ are independently substituted as phenyl or benzyl groups being optionally substituted with one or more substituents selected from C₁-C₂₀ (preferably C₁-C₁₀) straight, branched or cyclo alkyl groups, halo alkyl groups, hydroxyl, alkoxy, nitrile, nitro, amino, amide, ester, sulfone, sulfoxide, sulfonamide, and halogen atoms; or
R₁ and R₂ are independently substituted with a heterocyclic saturated, unsaturated or aromatic 5- or 6-member ring containing one or more heteroatoms selected from nitrogen, oxygen and sulfur and being optionally substituted with one or more substituents selected from C₁-C₂₀ (preferably C₁-C₁₀) straight, branched or cyclo alkyl, halo alkyl groups, hydroxyl, alkoxy, nitrile, nitro, amino, amide, ester, sulfone, sulfoxide or halogen atoms;
R₃ and R₄ are independently substituted with hydrogen, C₁-C₁₀ straight or branched or cyclo alkyl or halo alkyl groups or $R_3$ and $R_4$ can combine to form 3- to 6-membered rings;

$R_5$=H or $C_1$-$C_{20}$, preferably $C_1$-$C_{10}$, straight or branched alkyl groups, $C_1$-$C_{10}$ straight or branched haloalkyl groups;

Y is a bivalent radical having the following meaning:

g) Straight or branched $C_1$-$C_{20}$ (preferably $C_1$-$C_{10}$) alkyl, being optionally substituted with one or more of the substituents selected from the group consisting of: halogen atoms and hydroxyl;

h) —C(O)($C_1$-$C_{10}$ alkyl)- or —C(O)($CH_2$)$_n$C(O)O—($C_1$-$C_{10}$ alkyl)- or —($C_1$-$C_{10}$ alkyl)-;

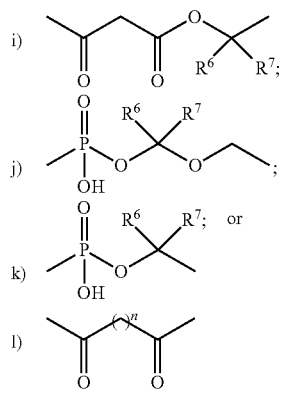

wherein n is an integer from 0 to 20;

$R^6$ and $R^7$ are independently H or $C_1$-$C_{10}$, straight or branched alkyl groups, $C_1$-$C_{10}$ straight or branched haloalkyl groups; or $R^6$ and $R^7$ can combine to form 3- to 6-membered rings; and Z is H, —OH, $C_{1-6}$ alkoxy, —COOH, —$NR^8R^9$;

$R^8$ and $R^9$ are independently substituted as $C_1$-$C_{20}$ alkyl, preferably $C_1$-$C_{10}$, being optionally substituted with one or more substituents selected from hydroxyl, amino, ester, carboxylic acid, and halogen atoms; or $R^8$ and $R^9$ can combine to form 3- to 6-membered rings containing one or more heteroatoms which are selected from the group consisting of:

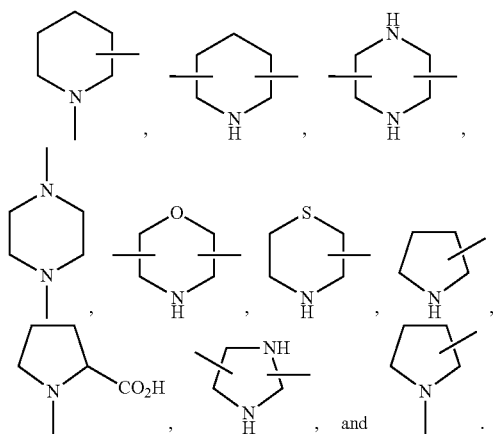

In some embodiments, a compound of formula (I) is an atropine of formula (IA),

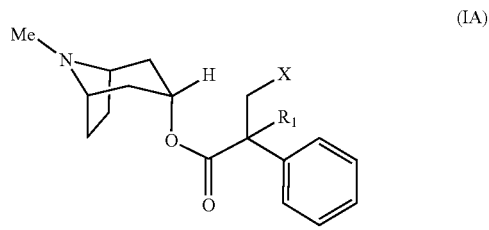

wherein Me, $R_1$ and X are as described above.

Definitions

Unless specified otherwise, the term "compounds of the present invention" or "compound of the present invention" refers to compounds of formula (I), subformulae thereof, and exemplified compounds, and salts thereof, as well as all stereoisomers (including diastereoisomers and enantiomers), rotamers, tautomers and isotopically labeled compounds (including deuterium substitutions), as well as inherently formed moieties.

The language "effective amount" of the compounds of the invention, described infra, refers to that amount of a therapeutic compound necessary or sufficient to perform its intended function within a mammal, e.g., treat a muscarinic receptor associated disorder, or a disease state in a mammal. An effective amount of the therapeutic compound can vary according to factors such as the amount of the causative agent already present in the mammal, the age, sex, and weight of the mammal, and the ability of the therapeutic compounds of the present invention to affect the muscarinic receptor associated disorder in the mammal. One of ordinary skill in the art would be able to study the aforementioned factors and make a determination regarding the effective amount of the therapeutic compound without undue experimentation. An in vitro or in vivo assay also can be used to determine an "effective amount" of the therapeutic compounds described infra. The ordinarily skilled artisan would select an appropriate amount of the therapeutic compound for use in the aforementioned assay or as a therapeutic treatment.

The phrase "ophthalmically compatible" is art-recognized and refers to formulations, polymers and other materials and/or dosage forms which are suitable for use in contact with the ocular tissues of human beings and animals without excessive toxicity, irritation, allergic response, or other problem or complication, commensurate with a reasonable benefit/risk ratio as determined by one of ordinary skill in the art.

As used herein, a pharmaceutical composition is a composition suitable for pharmaceutical use. A composition suitable for pharmaceutical use may be sterile, homogeneous and/or isotonic. Pharmaceutical compositions may be prepared in certain embodiments in an aqueous form, for example in a pre-filled syringe or other single- or multi-dose container. In certain embodiments, the pharmaceutical compositions of the invention are ophthalmically compatible and suitable for ophthalmic administration to a human subject by, for example, topical or other known methods of delivery. In another embodiment, the pharmaceutical compositions of the invention are suitable for intravitreal administration. In yet another embodiment, the pharmaceutical compositions of the invention are suitable for administration by intravitreal infusion. In yet another embodiment, the pharmaceutical compositions are administered orally.

As used herein, the term "alkyl" is intended to include branched, straight chain and cyclic, substituted or unsubstituted saturated aliphatic hydrocarbon groups. Alkyl groups can comprise about 1 to about 24 carbon atoms ("$C_1$-$C_{24}$"), about 7 to about 24 carbon atoms ("$C_7$-$C_{24}$"), about 8 to about 24 carbon atoms ("$C_1$-$C_{24}$"), or about 9 to about 24 carbon atoms ("$C_9$-$C_{24}$"). Alkyl groups can also comprise about 1 to about 8 carbon atoms ("$C_1$-$C_3$"), about 1 to about 6 carbon atoms ("$C_1$-$C_6$"), or about 1 to about 3 carbon atoms ("$C_1$-$C_3$"). Examples of $C_1$-$C_6$ alkyl groups include, but are not limited to, methyl, ethyl, propyl, isopropyl, n-butyl, isobutyl, tert-butyl, n-pentyl, neopentyl and n-hexyl radicals.

As used herein, the term "$C_{2-6}$ alkenyl" refers to a straight or branched hydrocarbon chain radical group consisting solely of carbon and hydrogen atoms, containing at least one double bond, having from two to six carbon atoms, which is attached to the rest of the molecule by a single bond. The terms "$C_2$-$C_{20}$ alkenyl" and "$C_2$-$C_{10}$ alkenyl" are to be construed accordingly. Examples of $C_{2-6}$ alkenyl include, but are not limited to, ethenyl, prop-1-enyl, but-1-enyl, pent-1-enyl, pent-4-enyl and penta-1,4-dienyl.

As used herein, the term "$C_{2-6}$ alkynyl" refers to a straight or branched hydrocarbon chain radical group consisting solely of carbon and hydrogen atoms, containing at least one triple bond, having from two to six carbon atoms, and which is attached to the rest of the molecule by a single bond. The term "$C_{2-4}$ alkynyl" is to be construed accordingly. Examples of $C_{2-6}$ alkynyl include, but are not limited to, ethynyl, prop-1-ynyl, but-1-ynyl, pent-1-ynyl, pent-4-ynyl and penta-1,4-diynyl.

As used herein, the term "$C_{1-6}$ alkoxy" refers to a radical of the formula —$OR_a$ where $R_a$ is a $C_{1-6}$ alkyl radical as generally defined above. Examples of $C_{1-6}$ alkoxy include, but are not limited to, methoxy, ethoxy, propoxy, isopropoxy, butoxy, isobutoxy, pentoxy, and hexoxy.

"Halogen" refers to bromo, chloro, fluoro or iodo.

As used herein, the term "heterocyclyl" or "heterocyclic" refers to a stable 5- or 6-membered non-aromatic monocyclic ring radical which comprises 1, 2, or 3, heteroatoms individually selected from nitrogen, oxygen and sulfur. The heterocyclyl radical may be bonded via a carbon atom or heteroatom. Examples of heterocyclyl include, but are not limited to, azetidinyl, oxetanyl, pyrrolinyl, pyrrolidyl, tetrahydrofuryl, tetrahydrothienyl, piperidyl, piperazinyl, tetrahydropyranyl, morpholinyl or perhydroazepinyl.

As used herein, the term "heteroaryl" refers to a 5- or 6-membered aromatic monocyclic ring radical which comprises 1, 2, 3 or 4 heteroatoms individually selected from nitrogen, oxygen and sulfur. The heteroaryl radical may be bonded via a carbon atom or heteroatom. Examples of heteroaryl include, but are not limited to, furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl.

The present invention provides in certain embodiments novel pharmaceutical formulations, in particular novel pharmaceutical formulations in which the active ingredient comprises a muscarinic modulator of the general formula (I) or (II) and/or a pharmaceutically acceptable salts thereof:

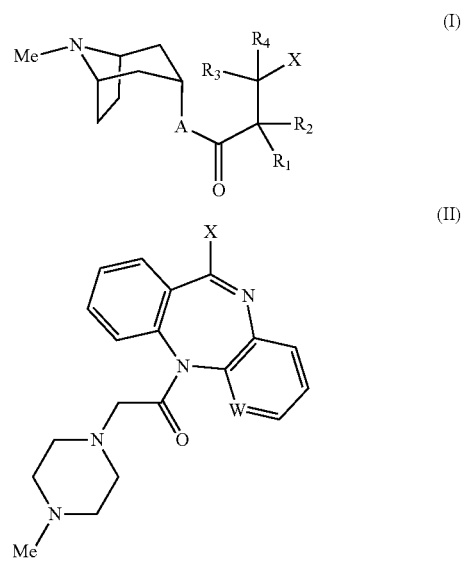

wherein
Me=$CH_3$;
A=O or $NR_5$;
W=N or CH;
X=—OH, —O—Y—Z, —S—Y—Z, or —$NR_5$—Y—Z;
$R_1$ and $R_2$ are independently substituted as H, D, hydroxyl, alkoxy, nitrile, halogen atoms, $C_1$-$C_{20}$ (preferably $C_1$-$C_{10}$) straight, branched or cyclo alkyl groups optionally substituted with halogen atoms; or
$R_1$ and $R_2$ are independently substituted as phenyl or benzyl groups being optionally substituted with one or more substituents selected from $C_1$-$C_{20}$ (preferably $C_1$-$C_{10}$) straight, branched or cyclo alkyl groups, halo alkyl groups, hydroxyl, alkoxy, nitrile, nitro, amino, amide, ester, sulfone, sulfoxide, sulfonamide, and halogen atoms; or
$R_1$ and $R_2$ are independently substituted with a heterocyclic saturated, unsaturated or aromatic 5- or 6-member ring containing one or more heteroatoms selected from nitrogen, oxygen and sulfur and being optionally substituted with one or more substituents selected from $C_1$-$C_{20}$ (preferably $C_1$-$C_{10}$) straight, branched or cyclo alkyl, halo alkyl groups, hydroxyl, alkoxy, nitrile, nitro, amino, amide, ester, sulfone, sulfoxide or halogen atoms;
$R_3$ and $R_4$ are independently substituted with hydrogen, $C_1$-$C_{10}$ straight or branched or cyclo alkyl or halo alkyl groups or
$R_3$ and $R_4$ can combine to form 3- to 6-membered rings;
$R_5$=H or $C_1$-$C_{20}$, preferably $C_1$-$C_{10}$, straight or branched alkyl groups, $C_1$-$C_{10}$ straight or branched haloalkyl groups;
Y is a bivalent radical having the following meaning:
  a) Straight or branched $C_1$-$C_{20}$ (preferably $C_1$-$C_{10}$) alkyl, being optionally substituted with one or more of the substituents selected from the group consisting of: halogen atoms and hydroxyl;
  b) —C(O)($C_1$-$C_{10}$ alkyl)- or —C(O)($CH_2$)$_n$C(O)O—($C_1$-$C_{10}$ alkyl)- or —($C_1$-$C_{10}$ alkyl)-;
  c) 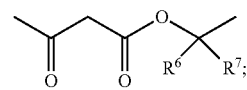

-continued

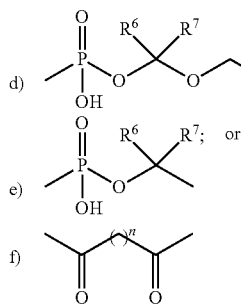

wherein n is an integer from 0 to 20;

$R^6$ and $R^7$ are independently H or $C_1$-$C_{10}$, straight or branched alkyl groups, $C_1$-$C_{10}$ straight or branched haloalkyl groups; or $R^6$ and $R^7$ can combine to form 3- to 6-membered rings; and Z is H, —OH, $C_{1-6}$ alkoxy, —COOH, —$NR^8R^9$;

$R^8$ and $R^9$ are independently substituted as $C_1$-$C_{20}$ alkyl, preferably $C_1$-$C_{10}$, being optionally substituted with one or more substituents selected from hydroxyl, amino, ester, carboxylic acid, and halogen atoms; or $R^8$ and $R^9$ can combine to form 3- to 6-membered rings containing one or more heteroatoms which are selected from the group consisting of:

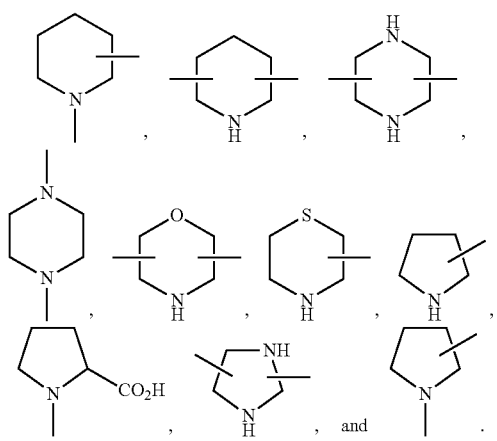

In some embodiments, a compound of formula (I) is an atropine of formula (IA),

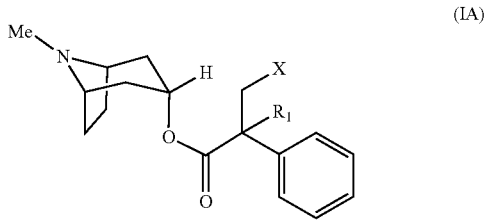

wherein Me, $R_1$ and X are as described above.

In some embodiments, compounds of formula (I) and formula (II) are selected from the group consisting of:
(1R,3r,5S)-8-methyl-8-azabicyclo[3.2.1]octan-3-yl 2-fluoro-3-hydroxy-2-phenylpropanoate,
(1R,3r,5S)-8-methyl-8-azabicyclo[3.2.1]octan-3-yl 2-methyl-3-hydroxy-2-phenylpropanoate,
(1R,3r,5S)-8-methyl-8-azabicyclo[3.2.1]octan-3-yl 2-benzyl-3-hydroxy-2-phenylpropanoate,
(1R,3r,5S)-8-Methyl-8-azabicyclo[3.2.1]octan-3-yl 3-hydroxy-2-methyl-2-(thiophen-2-yl) propanoate,
(1R,3r,5S)-8-Methyl-8-azabicyclo[3.2.1]octan-3-yl3-hydroxy-2-(hydroxymethyl)-2-phenylpropanoate,
(1R,3r,5S)-8-Methyl-8-azabicyclo[3.2.1]octan-3-yl 2-(hydroxymethyl)-2-phenylbutanoate,
(1R,3r,5S)-8-Methyl-8-azabicyclo[3.2.1]octan-3-yl 3-cyclopropyl-2-(hydroxymethyl)-2-phenylpropanoate,
(1R,3r,5S)-8-Methyl-8-azabicyclo[3.2.1]octan-3-yl 3-fluoro-2-methyl-2-phenylpropanoate,
(1R,3r,5S)-8-Methyl-8-azabicyclo[3.2.1]octan-3-yl 4,4,4-trifluoro-2-(hydroxymethyl)-2-phenyl butanoate,
(1R,3r,5S)-8-Methyl-8-azabicyclo[3.2.1]octan-3-yl2,3-dihydroxy-2-phenylpropanoate,
(1R,3r,5S)-8-Methyl-8-azabicyclo[3.2.1]octan-3-yl 3-methoxy-2-methyl-2-phenylpropanoate,
(1R,3r,5S)-8-Methyl-8-azabicyclo[3.2.1]octan-3-yl3-hydroxy-2-(4-methoxybenzyl)-2-phenylpropanoate,
(1R,3r,5S)-8-Methyl-8-azabicyclo[3.2.1]octan-3-yl 3-hydroxy-2-(4-chlorobenzyl)-2-phenyl propanoate,
(1R,3r,5S)-8-Methyl-8-azabicyclo[3.2.1]octan-3-yl 3-hydroxy-2-(2-chlorobenzyl)-2-phenyl propanoate,
(1R,3r,5S)-8-Methyl-8-azabicyclo[3.2.1]octan-3-yl 3-hydroxy-2-(4-hydroxybenzyl)-2-phenyl propanoate formic acid salt,
2-Fluoro-3-hydroxy-N-((1R,3r,5S)-8-methyl-8-azabicyclo[3.2.1]octan-3-yl)-2-phenylpropanamide,
(1R,3r,5S)-8-Methyl-8-azabicyclo[3.2.1]octan-3-yl 2-(4-fluorobenzyl)-3-hydroxy-2-phenyl propanoate,
(1R,3r,5S)-8-Methyl-8-azabicyclo[3.2.1]octan-3-yl 3-hydroxy-2-(4-methylbenzyl)-2-phenyl propanoate,
(1R,3r,5S)-8-methyl-8-azabicyclo[3.2.1]octan-3-yl 2-(3-chlorobenzyl)-3-hydroxy-2-phenyl propanoate,
(1R,3r,5S)-8-Methyl-8-azabicyclo[3.2.1]octan-3-yl 3-hydroxy-2-(4-methoxybenzyl)-2-phenyl propanoate,
(1R,3r,5S)-8-Methyl-8-azabicyclo[3.2.1]octan-3-yl 3-hydroxy-2-(4-methoxybenzyl)-2-phenyl propanoate,
(1R,3r,5S)-8-Methyl-8-azabicyclo[3.2.1]octan-3-yl 2-(4-(benzyloxy)phenyl)propanoate, and 6-((11-(2-(4-Methylpiperazin-1-yl)acetyl)-11H-benzo[e]pyrido[3,2-b][1,4]diazepin-6-yl)oxy)hexyl nitrate.

Additional compounds of the present invention include the following:

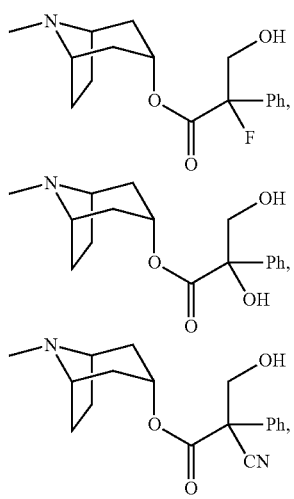

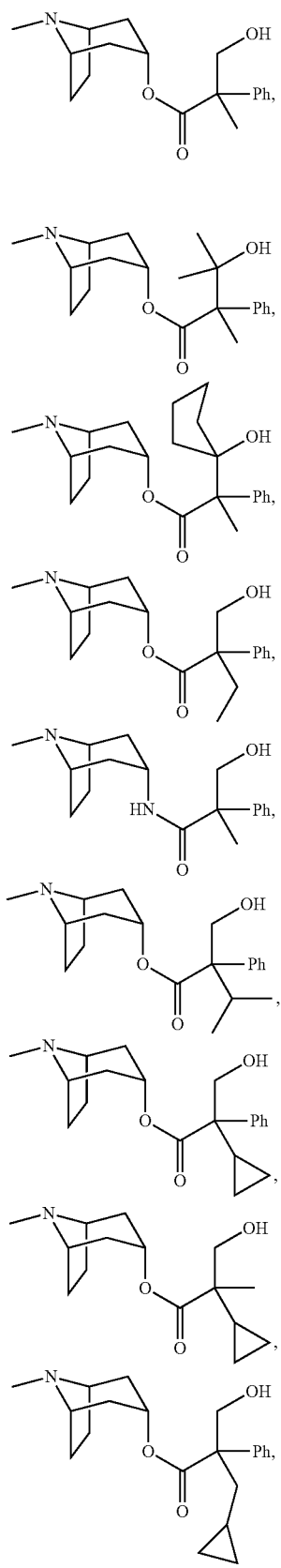

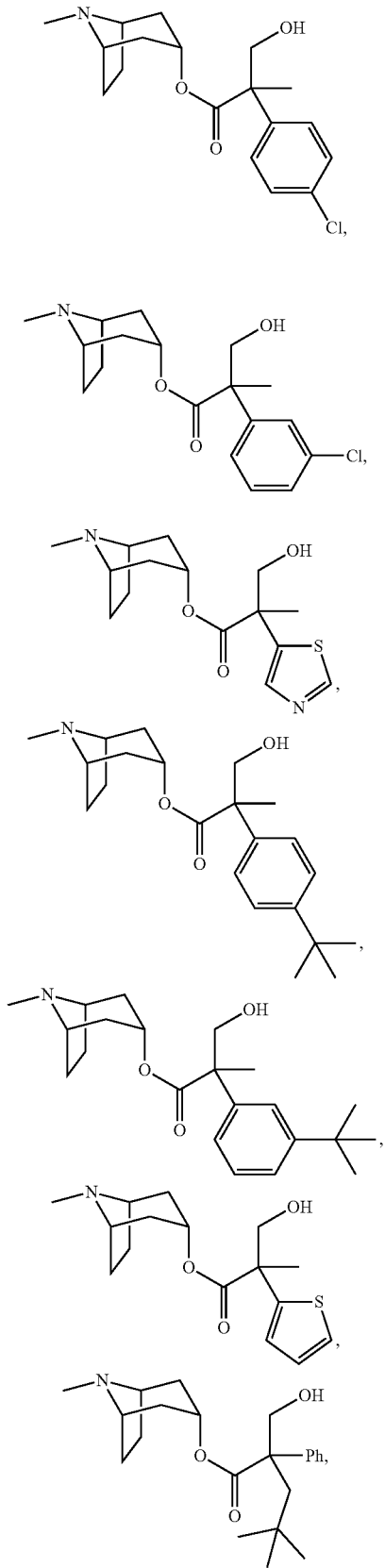
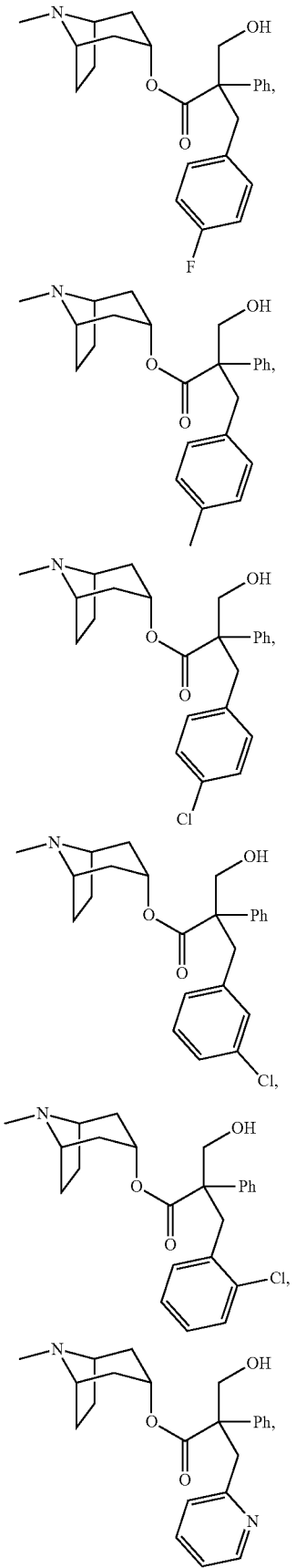

-continued
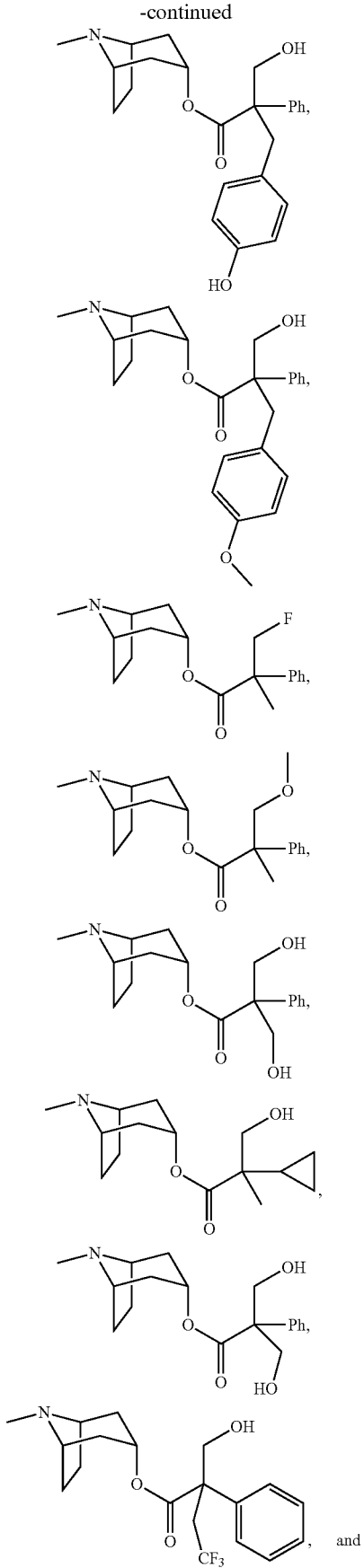
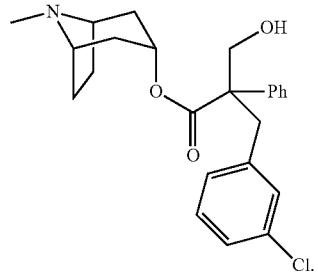
The following paragraphs provide examples of compounds according to the present invention:
EXAMPLES
Examples 1-3
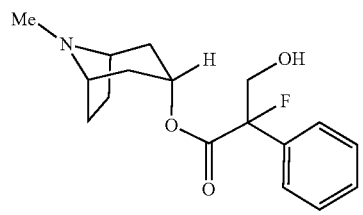
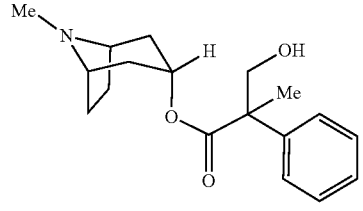
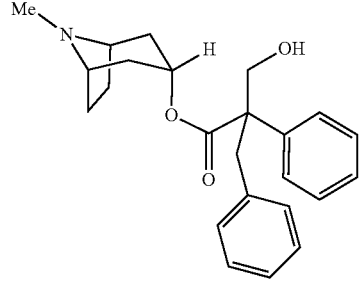
NMR spectra were taken on a Bruker 400 MHz spectrometer or a Bruker 300 MHz spectrometer.

LCMS methods are detailed below (unless otherwise stated):

Standard LCMS Method:

| | |
|---|---|
| Instrumentation | Acquity H-Class (quaternary pump/PDA detector) + QDa Mass Spectrometer |
| Column | Acquity UPLC CSH C18 1.7 μm, 50 × 2.1 mm at 40° C. |
| Mobile Phase A | 0.1% Aqueous formic acid (v/v) |
| Mobile Phase B | 0.1% Formic acid in acetonitrile (v/v) |
| Flow | 1.0 mL/min |

| Gradient Program | Time (min) | % A | % B |
|---|---|---|---|
| | 0.0 | 97 | 03 |
| | 1.5 | 01 | 99 |
| | 1.9 | 01 | 99 |
| | 2.0 | 97 | 03 |
| | 2.5 | 97 | 03 |

| | |
|---|---|
| Sample | 1 μL injection (Open Access) |
| Detectors | UV, diode array 190-400 nm |
| | MS, mass 160-800 (or 60-800 for LM or 300-1200 for HM method) in ES+ & ES− |

| | |
|---|---|
| Instrumentation | Acquity UPLC (binary pump/PDA detector) + ZQ Mass Spectrometer |
| Column | ACQUITY UPLC BEH $C_{18}$ 1.7 μm, 100 × 2.1 mm, maintained at 40° C. |
| Mobile Phase A | 0.1% Aqueous formic acid (v/v) |
| Mobile Phase B | 0.1% Formic acid in acetonitrile (v/v) |
| Flow | 0.4 mL/min |

| Gradient Program | Time (mins) | % A | % B |
|---|---|---|---|
| | 0.0 | 95 | 05 |
| | 0.4 | 95 | 05 |
| | 6.0 | 05 | 95 |
| | 6.8 | 05 | 95 |
| | 7.0 | 95 | 05 |
| | 8.0 | 95 | 05 |

| | |
|---|---|
| Sample | 1 μL injection of a 0.2-0.5 mg/ml solution in an appropriate solvent at 20° C. |
| Detectors | UV, diode array 200-500 nm |
| | MS, mass 100-800 (or −1500 for HM method) in ES+ & ES− (no split to MS) |
| Data Analysis | Peak area percentage (APCT) with an integration threshold of 0.2% (relative) |

Abbreviations:
DAST Diethylaminosulfur trifluoride
DCM Dichloromethane
DMF Dimethylformamide
RT Room Temperature Synthetic Scheme of Example 1: (1R,3r,5S)-8-methyl-8-azabicyclo[3.2.1]octan-3-yl 2-fluoro-3-hydroxy-2-phenylpropanoate

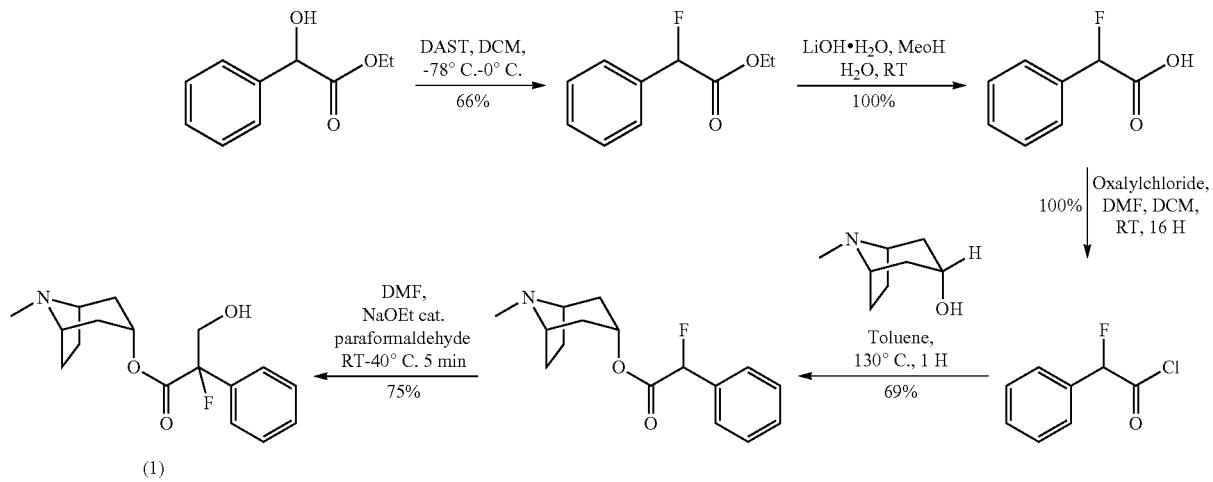

(1)

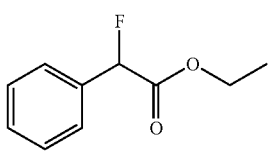

ethyl 2-fluoro-2-phenylacetate

To a solution of ethyl mandelate (93 g, 0.52 mol) in DCM (1.5 L) at −78° C. was added DAST (81.8 mL, 0.62 mol) at such a rate that T≤−60° C. The reaction mixture was stirred whilst allowed to warm to 0° C. After 1 h. the reaction was slowly made basic with 1N NaOH until pH ~7. The mixture was extracted with DCM. The combined organic fractions were washed with brine, dried (MgSO₄) and concentrated in vacuo to give the title compound as a straw coloured oil (62.4 g, 66%). The material was used without purification.

$^1$H NMR (400 MHz, CDCl$_3$) δ 7.54-7.36 (5H, m), 5.77 (1H, d, J=47.3 Hz), 4.32-4.16 (2H, m), 1.26 (3H, t, J=7.2 Hz). The $^1$H NMR spectrum is shown in FIG. 1.

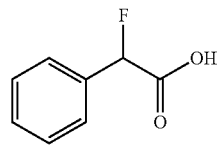 [SMILES: O=C(O)C(F)c1ccccc1]

2-fluoro-2-phenylacetic acid

To a solution of ethyl 2-fluoro-2-phenylacetate (32.4 g, 0.18 mol) in MeOH (100 mL) was added LiOH.H₂O (11.2 g, 0.27 mol) in water (15 mL) and the reaction stirred at RT for 1 h. (a slight exotherm was noted). The reaction mixture was diluted with ethyl acetate and acidified to ~pH 3 with 1N HCl. The product was extracted with ethyl acetate and the combined organic fractions were washed with brine, dried (MgSO₄) and concentrated in vacuo to give the title compound as a white solid (27.4 g, 100%). The material was used without purification.

Figure 2:
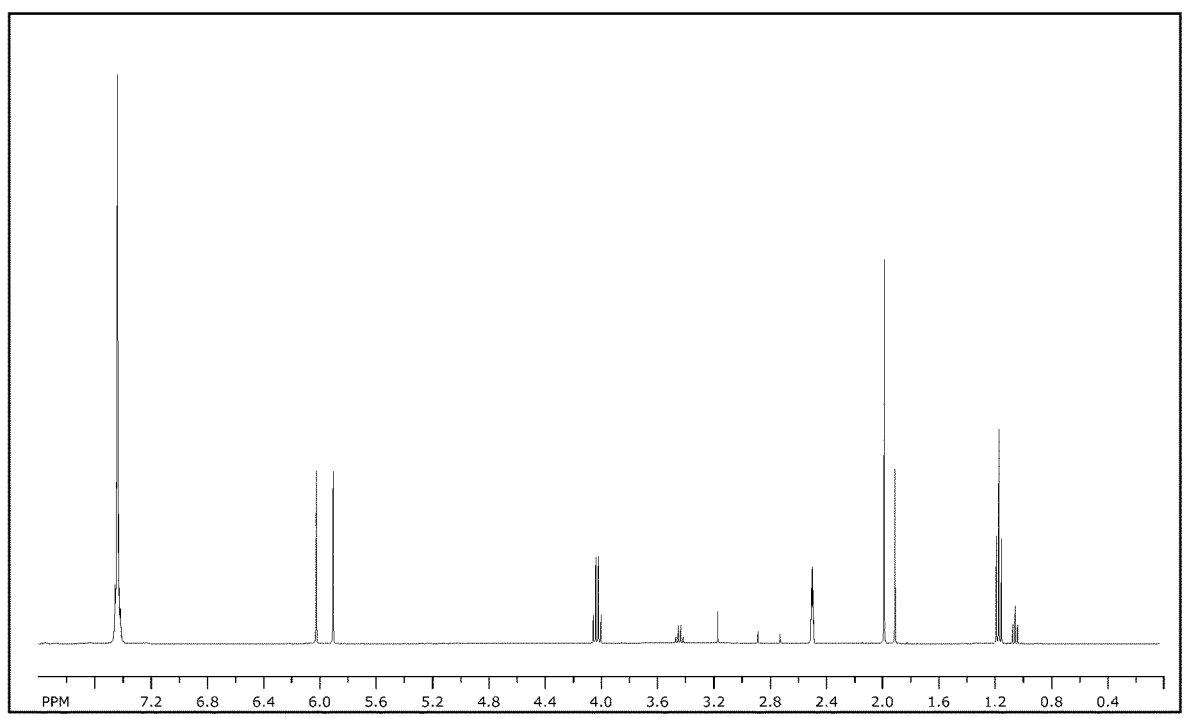
FIG. 2 is a $^1$H NMR spectrum of 2-fluoro-2-phenylacetic acid.

$^1$H NMR (400 MHz, d₆-DMSO) δ 13.47 (1H, br s), 7.48-7.37 (5H, m), 5.95 (1H, d, J=47.6 Hz). The $^1$H NMR spectrum is shown in FIG. 2.

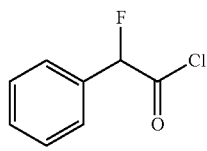 [SMILES: O=C(Cl)C(F)c1ccccc1]

2-fluoro-2-phenylacetyl chloride

To a solution of 2-fluoro-2-phenylacetic acid (27.4 g, 0.18 mol) in DCM (250 mL) at RT was added 1 drop of DMF. Oxalyl chloride (23.3 mL, 0.27 mol) was added causing effervescence. The reaction mixture was stirred at RT for 16 h. The reaction mixture was concentrated in vacuo to give the title compound as a straw coloured oil (30.1 g, 100%). Material used without purification.

Figure 3:
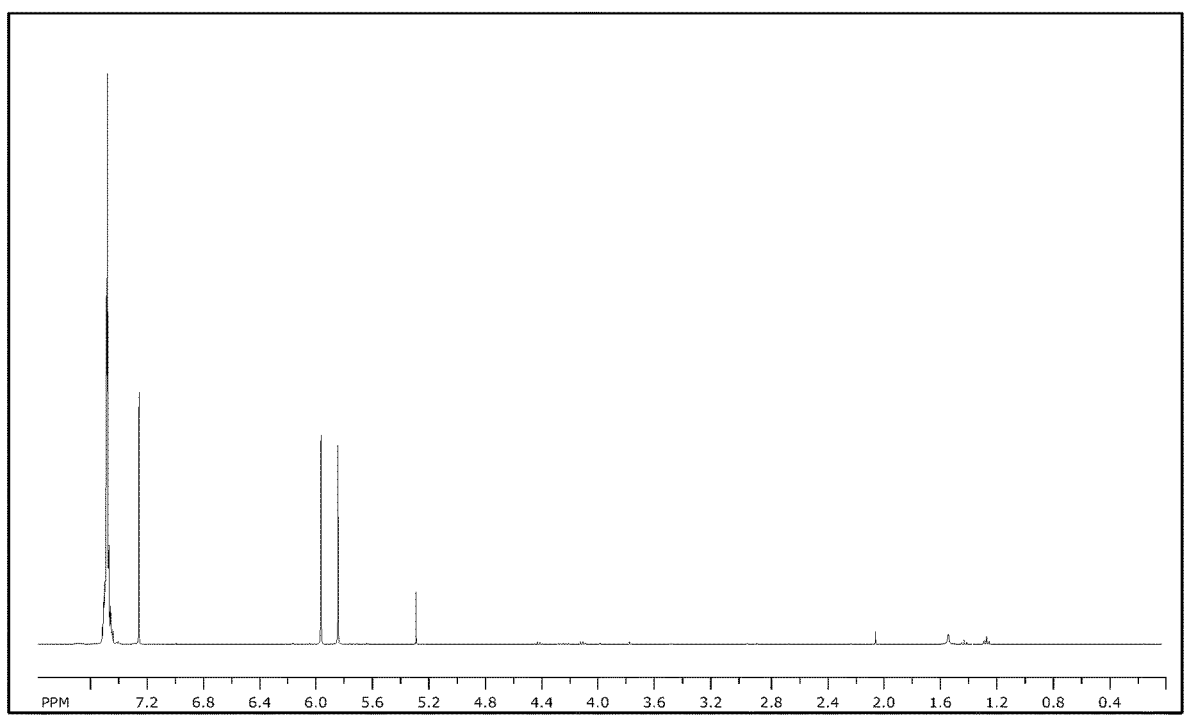
FIG. 3 is a $^1$H NMR spectrum of 2-fluoro-2-phenylacetyl chloride.

$^1$H NMR (400 MHz, CDCl$_3$) δ 7.54-7.43 (5H, m), 5.90 (1H, d, 47.6 Hz). The $^1$H NMR spectrum is shown in FIG. 3.

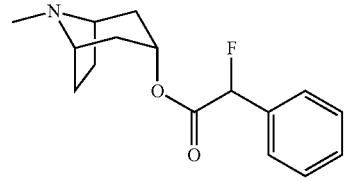

(1R,3r,5S)-8-methyl-8-azabicyclo[3.2.1]octan-3-yl 2-fluoro-2-phenylacetate

To a solution of tropine (27.1 g, 0.19 mol) in toluene (450 mL) was added 2-fluoro-2-phenylacetyl chloride (30.1 g, 0.17 mol) causing a precipitate to form. The reaction mixture was stirred at reflux for 1.5 h. The reaction mixture was diluted with ethyl acetate and extracted with 1N HCl. The combined aqueous fractions were basified to ~pH 13 with 1N NaOH and extracted with ethyl acetate. The combined organic fractions were washed with brine, dried (MgSO₄) and concentrated in vacuo to give the title compound as a straw coloured oil which solidified on standing (33.5 g, 69%).

Figure 4:
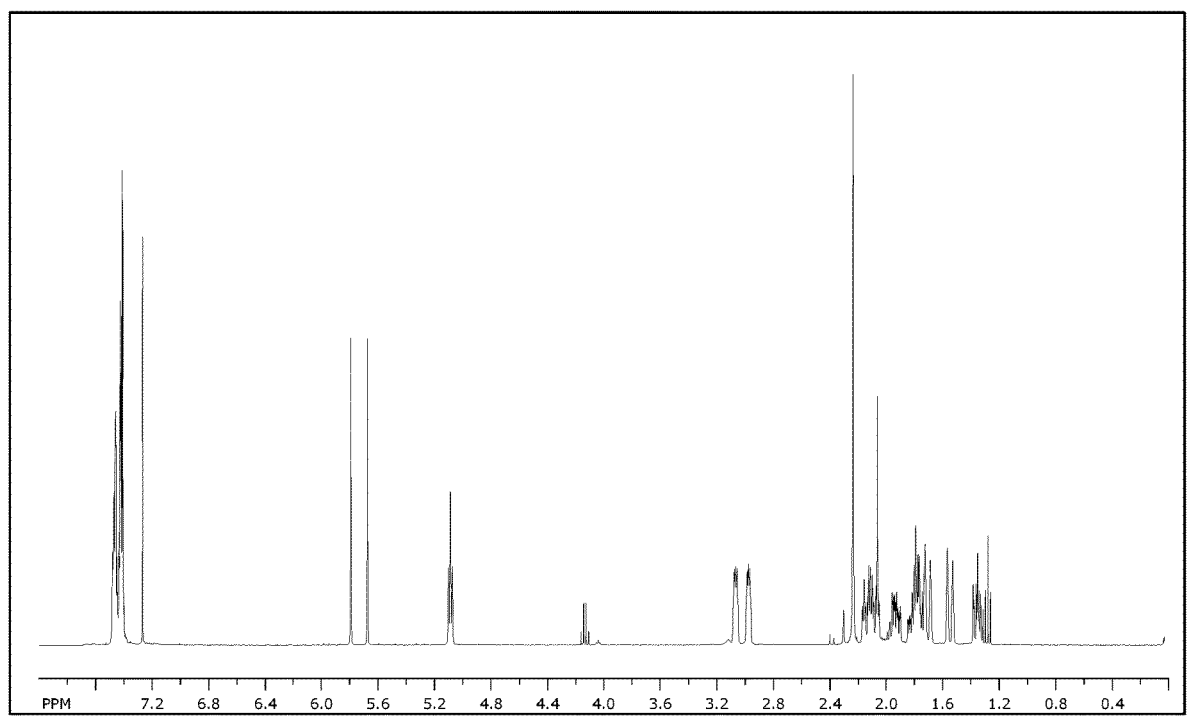
FIG. 4 is a $^1$H NMR spectrum of (1R,3r,5S)-8-methyl-8-azabicyclo[3.2.1]octan-3-yl 2-fluoro-2-phenylacetate.

$^1$H NMR (400 MHz, CDCl$_3$) δ 7.51-7.37 (5H, m), 5.73 (1H, d, J=47.9 Hz), 5.08 (1H, t, J=5.3 Hz), 3.07-2.93 (2H, m), 2.22 (3H, s), 2.16-2.01 (2H, m), 1.97-1.85 (1H, m), 1.84-1.64 (3H, m), 1.56-1.48 (1H, m), 1.37-1.29 (1H, m). The $^1$H NMR spectrum is shown in FIG. 4.

LCMS (ESI) [M+H]⁺ 278, R$_t$=0.70 min.

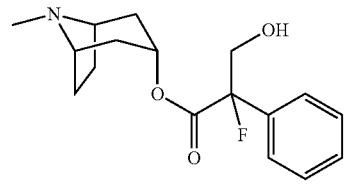 [SMILES: CN1C2CCC1CC(OC(=O)C(F)(CO)c1ccccc1)C2]

(1R,3r,5S)-8-methyl-8-azabicyclo[3.2.1]octan-3-yl 2-fluoro-3-hydroxy-2-phenylpropanoate To a solution of (1R,3r,5S)-8-methyl-8-azabicyclo[3.2.1]octan-3-yl 2-fluoro-2-phenylacetate (33.5 g, 0.12 mol) in DMF (120 mL) was added paraformaldehyde (5.45 g, 0.18 mol). To this suspension was added freshly prepared sodium ethoxide (140 mg sodium in 3.6 mL ethanol) causing the solids to dissolve. The reaction mixture was stirred at 40° C. for 5 min. The reaction mixture was diluted with ethyl acetate and extracted with 1N HCl and the combined aqueous fractions were basified to ~pH 13 with 1N NaOH and extracted with ethyl acetate. The combined organic fractions were washed with brine, dried (MgSO₄) and concentrated in vacuo to ~ ⅕ volume at which point the product crystallized. The solid was collected by filtration and dried in vacuo to give the title compound as a white solid (25.0 g, 67%). The mother liquors were concentrated in vacuo and triturated with ethyl acetate to give a second crop of similar purity to the first (2.92 g, 8%).

Figure 5:
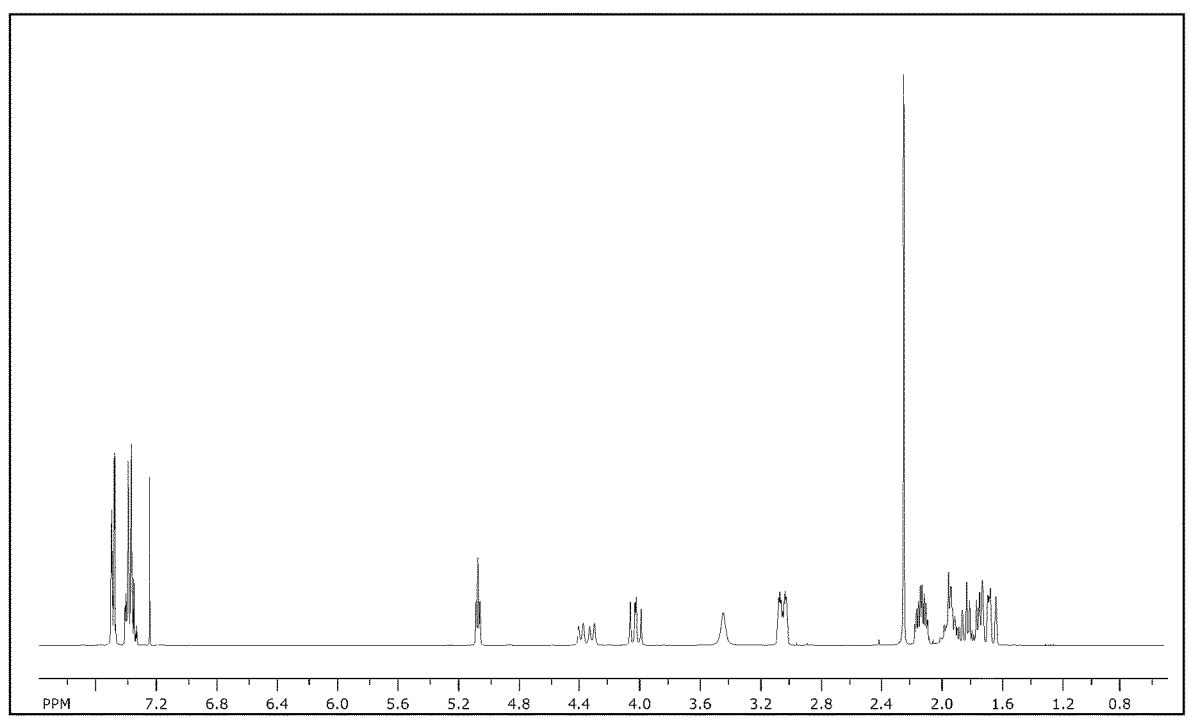
FIG. 5 is a $^1$H NMR spectrum of (1R,3r,5S)-8-methyl-8-azabicyclo[3.2.1]octan-3-yl 2-fluoro-3-hydroxy-2-phenylpropanoate.

$^1$H NMR (400 MHz, CDCl$_3$) δ 7.54-7.48 (2H, m), 7.45-7.35 (3H, m), 5.09 (1H, t, J=5.2 Hz), 4.36 (1H, dd, J=29.2, 13.2 Hz), 4.04 (1H, dd, J=15.3, 12.9 Hz), 3.10-2.99 (2H, m), 2.46 (1H, br s), 2.24 (3H, s), 2.18-2.06 (2H, m), 2.01-1.58 (6H, m). The ¹H NMR spectrum is shown in FIG. 5.

Figure 6:
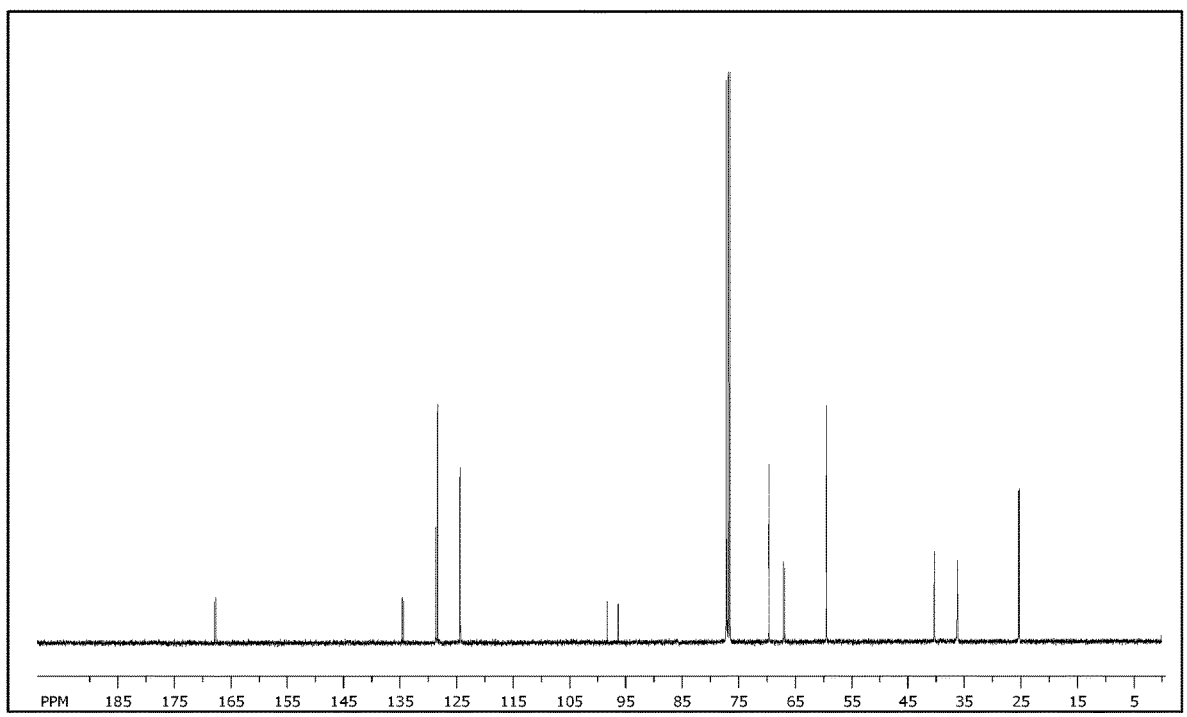
FIG. 6 is a $^{13}$C NMR spectrum of (1R,3r,5S)-8-methyl-8-azabicyclo[3.2.1]octan-3-yl 2-fluoro-3-hydroxy-2-phenylpropanoate

¹³C NMR (400 MHz, CDCl₃) δ 168.4, 134.8, 129.0, 128.7, 124.7, 97.5 (d, J=189 Hz), 69.8, 67.1, 59.6, 40.4, 36.3, 25.3. The ¹³C NMR spectrum is shown in FIG. 6.

LCMS (ESI) [M+H]⁺ 308, R$_t$=0.66 min.

QC LCMS (ESI) [M+H]⁺ 308.2, R$_t$=2.28 min. (94.2%), >99% purity by NMR.

Synthetic Scheme of Example 2: (1R,3r,5S)-8-methyl-8-azabicyclo[3.2.1]octan-3-yl 2-methyl-3-hydroxy-2-phenylpropanoate

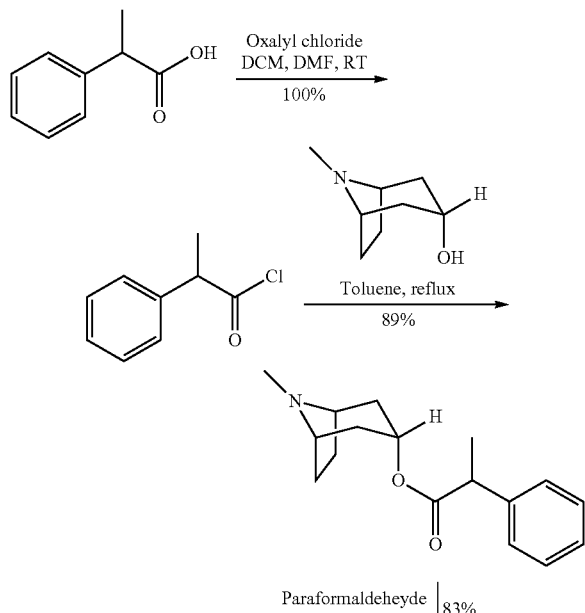

(2)

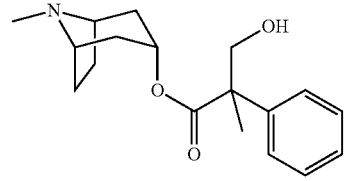

2-methyl-2-phenylacetyl chloride

To a solution of 2-methyl-2-phenylacetic acid (7.65 g, 50.94 mmol) in DCM (60 mL) at RT was added 1 drop of DMF. Oxalyl chloride (8.9 mL, 0.102 mol) was added causing effervescence. The reaction mixture was stirred at RT for 18 h. then concentrated in vacuo to give the title compound as a straw coloured oil (8.6 g, 100%). Material used without purification.

Figure 7:
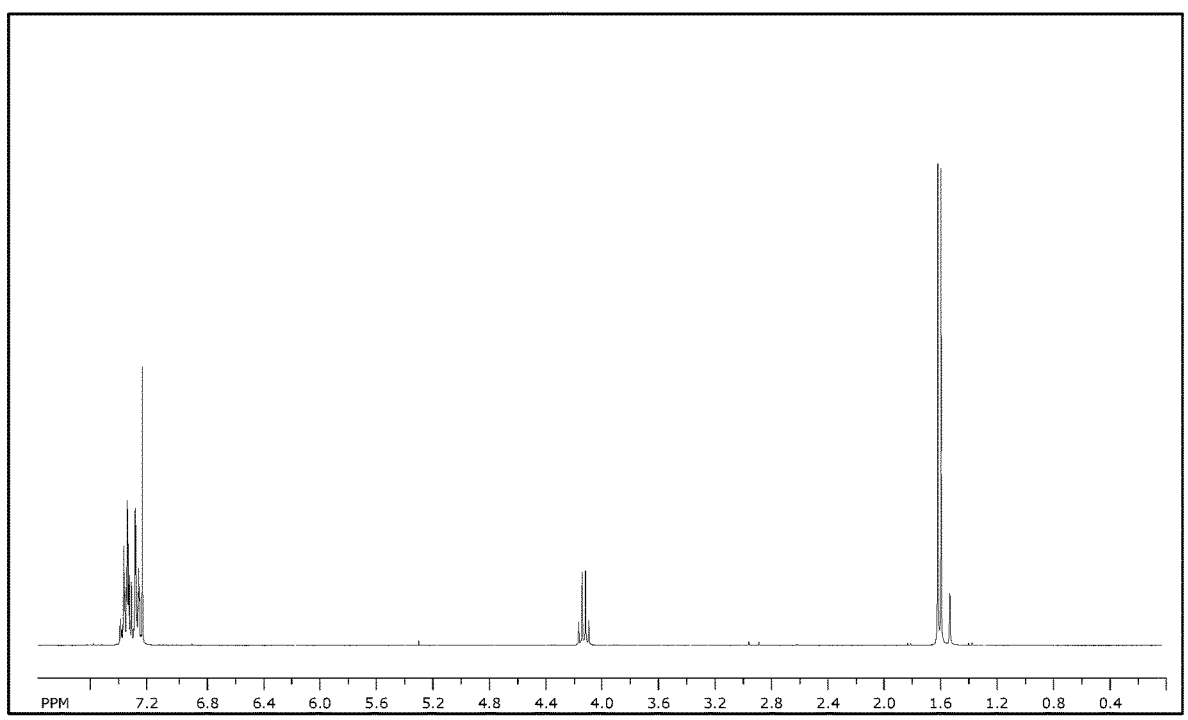
FIG. 7 is a $^1$H NMR spectrum of 2-methyl-2-phenylacetyl chloride.

¹H NMR (300 MHz, CDCl₃) δ 7.43-7.26 (5H, m), 4.12 (1H, quartet, J=7.1 Hz), 1.60 (3H, d, J=7.1 Hz). The ¹H NMR spectrum is shown in FIG. 7.

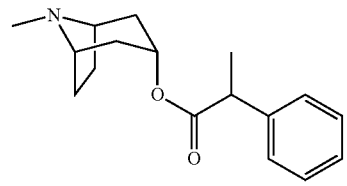 [SMILES: CC(C(=O)OC1CC2CCC(C1)N2C)c1ccccc1]

(1R,3r,5S)-8-methyl-8-azabicyclo[3.2.1]octan-3-yl 2-methyl-2-phenylacetate

To a solution of tropine (6.5 g, 45.9 mmol) in toluene (40 mL) was added 2-methyl-2-phenylacetyl chloride (8.6 g, 51.0 mmol) causing a precipitate to form. The reaction mixture was stirred at reflux for 2 h. The reaction mixture was concentrated in vacuo and the residue triturated with diethyl ether then solids filtered off to give a white solid. This solid was partitioned between H₂O and DCM, then basified to pH>10 using 1N NaOH and the product extracted into DCM. The combined DCM extracts were washed with H₂O and brine then passed through a phase separation cartridge and concentrated in vacuo to give the title compound as a straw coloured oil (11.43 g, 81%).

Figure 8:
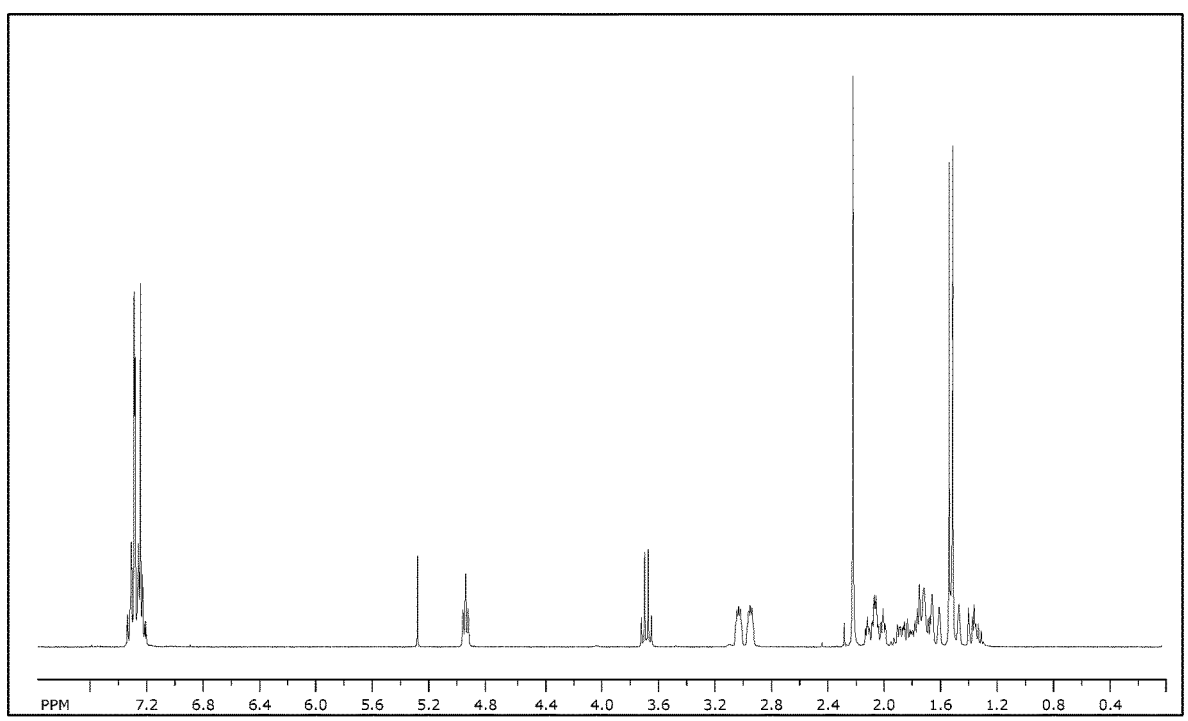
FIG. 8 is a $^1$H NMR spectrum of (1R,3r,5S)-8-methyl-8-azabicyclo[3.2.1]octan-3-yl 2-methyl-2-phenylacetate.

¹H NMR (300 MHz, CDCl₃) δ 7.36-7.21 (5H, m), 4.96 (1H, t, J=5.4 Hz), 3.67 (1H, quartet, J=7.2 Hz), 3.06-2.90 (2H, m), 2.21 (3H, s), 2.13-1.96 (2H, m), 1.95-1.57 (4H, m), 1.54-1.44 (1H, m), 1.51 (3H, d, J=7.2 Hz), 1.40-1.28 (1H, m). The ¹H NMR spectrum is shown in FIG. 8.

LCMS (ESI) [M+H]⁺ 274, R$_t$=0.79 min.

(1R,3r,5S)-8-methyl-8-azabicyclo[3.2.1]octan-3-yl 2-methyl-3-hydroxy-2-phenylpropanoate To a solution of (1R,3r,5S)-8-methyl-8-azabicyclo[3.2.1]octan-3-yl 2-methyl-2-phenylacetate (12.4 g, 45.36 mmol) in DMF (15 mL) was added paraformaldehyde (2.04 g, 68.04 mmol). To this suspension was added freshly prepared sodium ethoxide (52 mg sodium in 1.0 mL ethanol) causing the solids to dissolve. The reaction mixture was stirred at RT for 4 h. and then partitioned between H₂O and DCM. The combined DCM extracts were washed with H₂O and brine, passed through a phase separation cartridge and concentrated in vacuo. The resultant oil was triturated with diethyl ether at which point the product crystallized. The solid was collected by filtration and dried in vacuo to give the title compound as a white solid (10.5 g, 76%).

¹H NMR (400 MHz, CDCl₃) δ 7.38-7.25 (5H, m), 5.06 (1H, t, J=4.1 Hz), 4.12 (1H, dd, J=8.5, 4.2 Hz), 3.62 (1H, dd,

J=8.7, 6.0 Hz), 3.04-2.89 (2H, m), 2.55 (1H, t, J=5.2 Hz), 2.19 (3H, s), 2.15-2.00 (2H, m), 1.90-1.78 (1H, m), 1.74-1.57 (6H, m), 1.50-1.43 (1H, m), 1.23-1.11 (1H, m).

Figure 9:
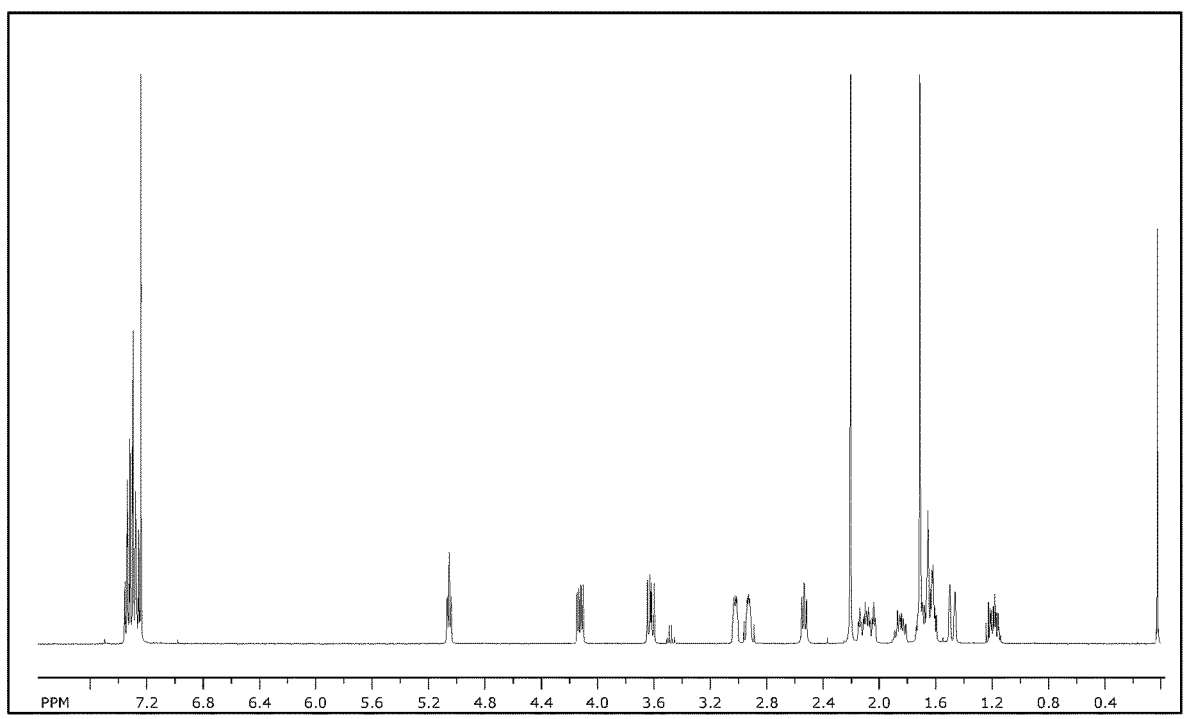
FIG. 9 is a $^1$H NMR spectrum of (1R,3r,5S)-8-methyl-8-azabicyclo[3.2.1]octan-3-yl 2-methyl-3-hydroxy-2-phenylpropanoate.

The $^1$H NMR spectrum is shown in FIG. 9.

Figure 10:
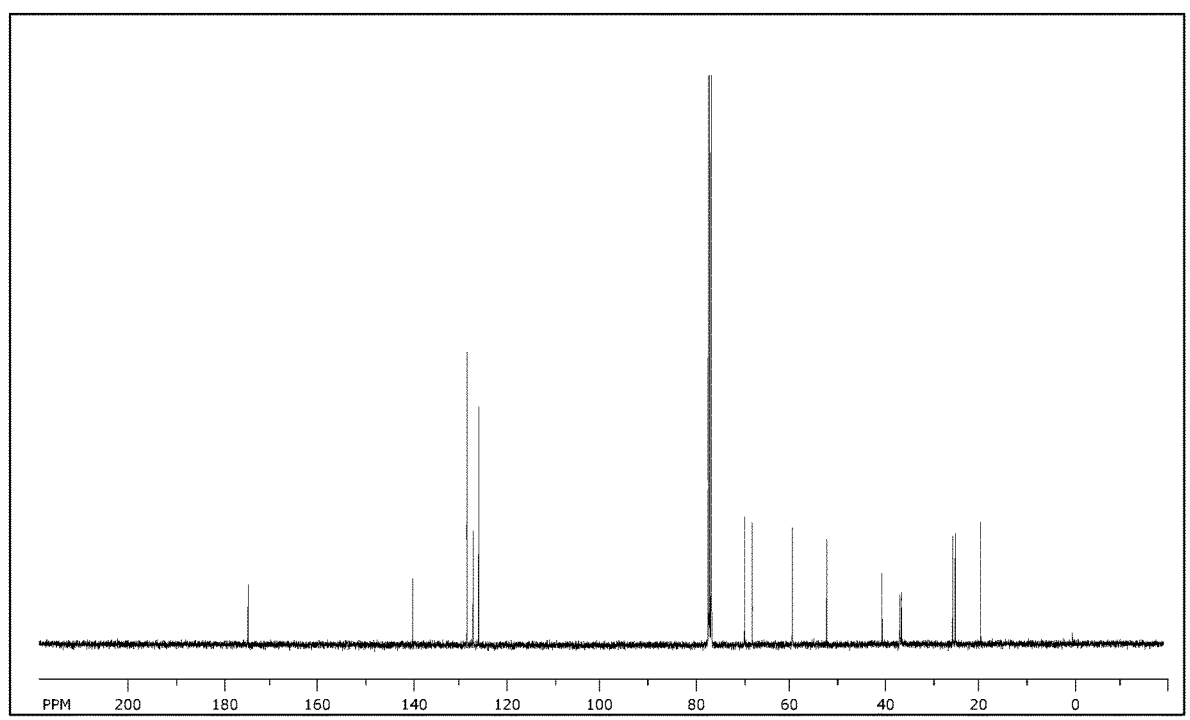
FIG. 10 is a $^{13}$C NMR spectrum of (1R,3r,5S)-8-methyl-8-azabicyclo[3.2.1]octan-3-yl 2-methyl-3-hydroxy-2-phenylpropanoate.

$^{13}$C NMR (400 MHz, CDCl$_3$) δ 175.2, 140.2, 128.6, 127.3, 126.2, 69.7, 68.0, 59.6, 59.5, 52.2, 40.4, 36.6, 36.3, 25.4, 24.9, 19.5 (The chiral centre leads to non-equivalence of the tropane ring carbon atoms, hence 16 signals, not 13 are observed). The $^{13}$C NMR spectrum is shown in FIG. 10.

LCMS (ESI) [M+H]$^+$ 304, R$_t$=0.69 min.

QC LCMS (ESI [M+H]$^+$ 304.2, R$_t$=2.38 min. (98.9%)

Synthetic Scheme of Example 3: (1R,3r,5S)-8-methyl-8-azabicyclo[3.2.1]octan-3-yl 2-benzyl-3-hydroxy-2-phenylpropanoate

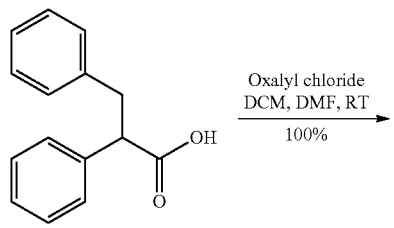

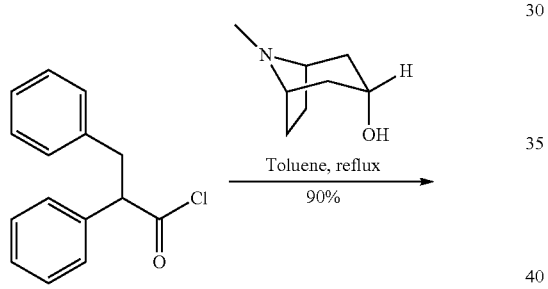

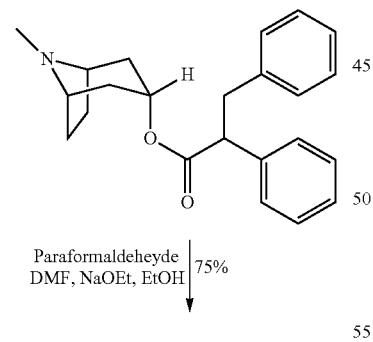

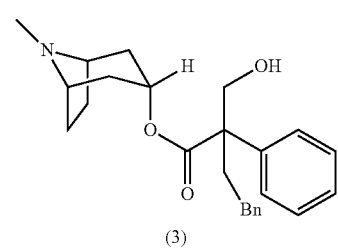

(3)

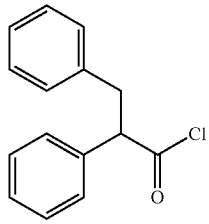 [SMILES: O=C(Cl)C(Cc1ccccc1)c1ccccc1]

2,3-diphenylpropanoyl chloride

To a solution of 2,3-diphenylpropanoic acid (16.0 g, 70.71 mmol) in DCM (80 mL) at RT was added DMF (0.10 mL) and the mixture cooled in an ice-water bath. Oxalyl chloride (12.3 mL, 141.42 mmol) was added causing effervescence and the cooling bath was removed. The reaction mixture was stirred at RT for 18 h. then concentrated in vacuo to give the title compound as a straw coloured oil (17.3 g, 100%). Material used without purification.

Figure 11:
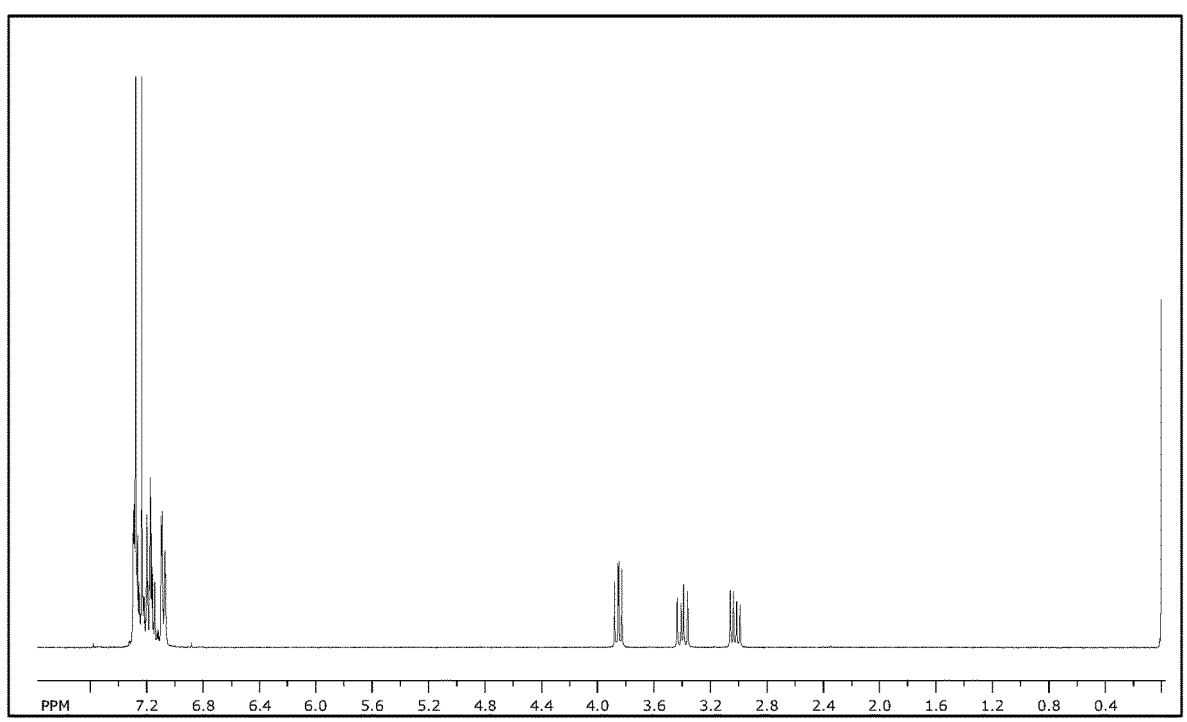
FIG. 11 is a $^1$H NMR spectrum of 2,3-diphenylpropanoyl chloride.

$^1$H NMR (300 MHz, CDCl$_3$) δ 7.33-7.07 (10H, m), 3.86 (1H, dd, J=7.0, 8.4 Hz), 3.41 (1H, dd, J=13.8, 8.4 Hz), 3.03 (1H, dd, J=13.8, 7.0 Hz). The $^1$H NMR spectrum is shown in FIG. 11.

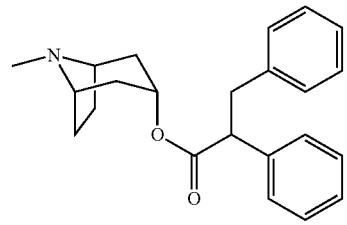 [SMILES: CN1C2CCC1CC(OC(=O)C(Cc1ccccc1)c1ccccc1)C2]

(1R,3r,5S)-8-methyl-8-azabicyclo[3.2.1]octan-3-yl 2,3-diphenylpropanoate

To a solution of tropine (9.49 g, 70.71 mmol) in toluene (70 mL) was added 2,3-diphenylpropanoyl chloride (17.30 g, 70.71 mmol) causing a precipitate to form. The reaction mixture was stirred at reflux for 2 h. then concentrated in vacuo. The residue was triturated with diethyl ether and solids filtered off to give a white solid. This solid was partitioned between H$_2$O and DCM, basified to pH>10 using 1N NaOH solution and product extracted into DCM. The DCM extracts were washed with H$_2$O and brine then passed through a phase separation cartridge and concentrated in vacuuo to give the title compound as a straw coloured oil (22.4 g, 90%).

Figure 12:
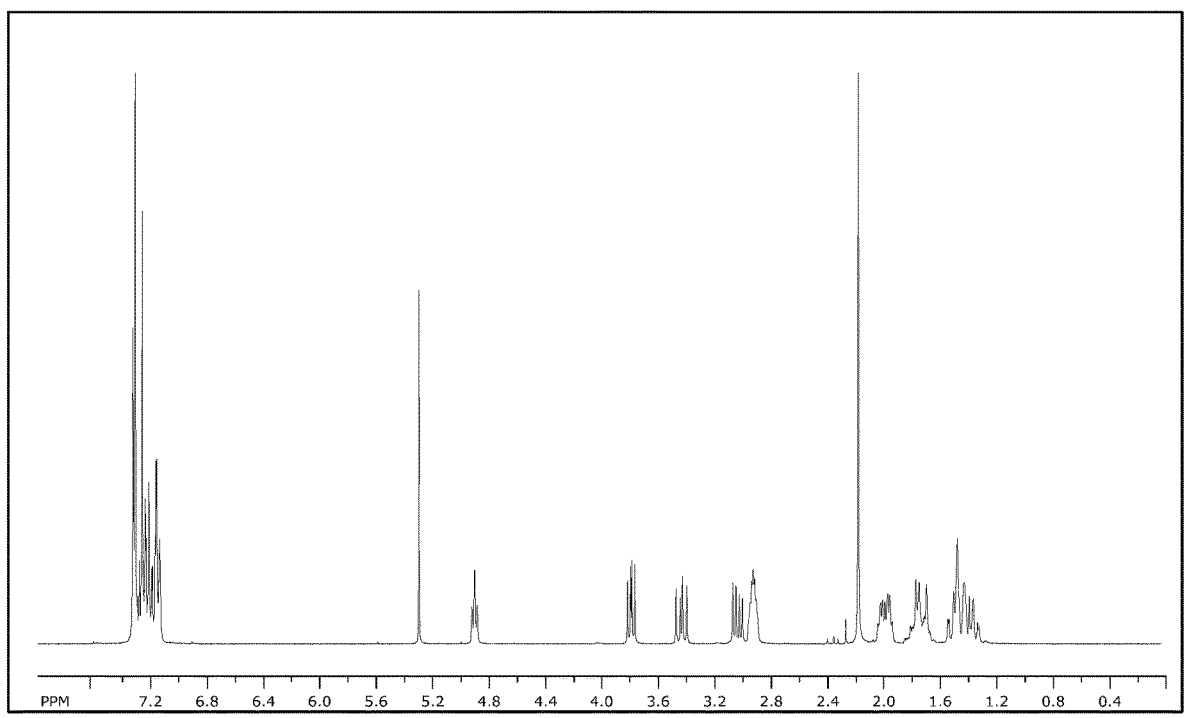
FIG. 12 is a $^1$H NMR spectrum of (1R,3r,5S)-8-methyl-8-azabicyclo[3.2.1]octan-3-yl 2,3-diphenylpropanoate.

$^1$H NMR (300 MHz, CDCl$_3$) δ 7.35-7.11 (10H, m), 4.90 (1H, t, J=5.4 Hz), 3.79 (1H, dd, J=6.5, 9.0 Hz), 3.43 (1H, dd, J=13.5, 9.0 Hz), 3.03 (1H, dd, J=13.5, 6.5 Hz), 2.97-2.87 (2H, m), 2.18 (3H, s), 2.05-1.92 (2H, m), 1.85-1.65 (2H, m), 1.56-1.30 (4H, m). The $^1$H NMR spectrum is shown in FIG. 12.

LCMS (ESI) [M+H]$^+$ 350, R$_t$=0.98 min.

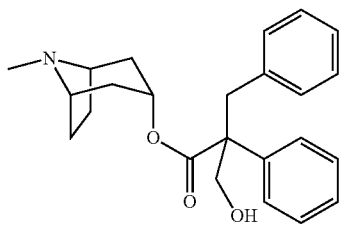 [SMILES: CN1C2CCC1CC(OC(=O)C(CO)(Cc1ccccc1)c1ccccc1)C2]

(1R,3r,5S)-8-methyl-8-azabicyclo[3.2.1]octan-3-yl 2-benzyl-3-hydroxy-2-phenylpropanoate To a solution of (1R,3r,5S)-8-methyl-8-azabicyclo[3.2.1]octan-3-yl 2,3-diphenylpropanoate (22.40 g, 64.10 mmol) in DMF (30 mL) was added paraformaldehyde (3.27 g, 108.96 mmol). To this suspension was added freshly prepared sodium ethoxide (74 mg sodium in 1.3 mL ethanol) causing the solids to dissolve. The reaction mixture was stirred at RT for 3 h. before H$_2$O was added. The precipitate was filtered off, washed with H$_2$O and dried in vacuo to remove most of the H$_2$O. The resultant "wet" solid was partitioned between MeOH and DCM and the phases separated. The DCM extract was dried (MgSO$_4$), filtered and concentrated in vacuo, which caused crystallization of the product to occur. The precipitate was filtered off and dried in vacuo to give the title compound as a white solid (18.18 g, 75%).

Figure 13:
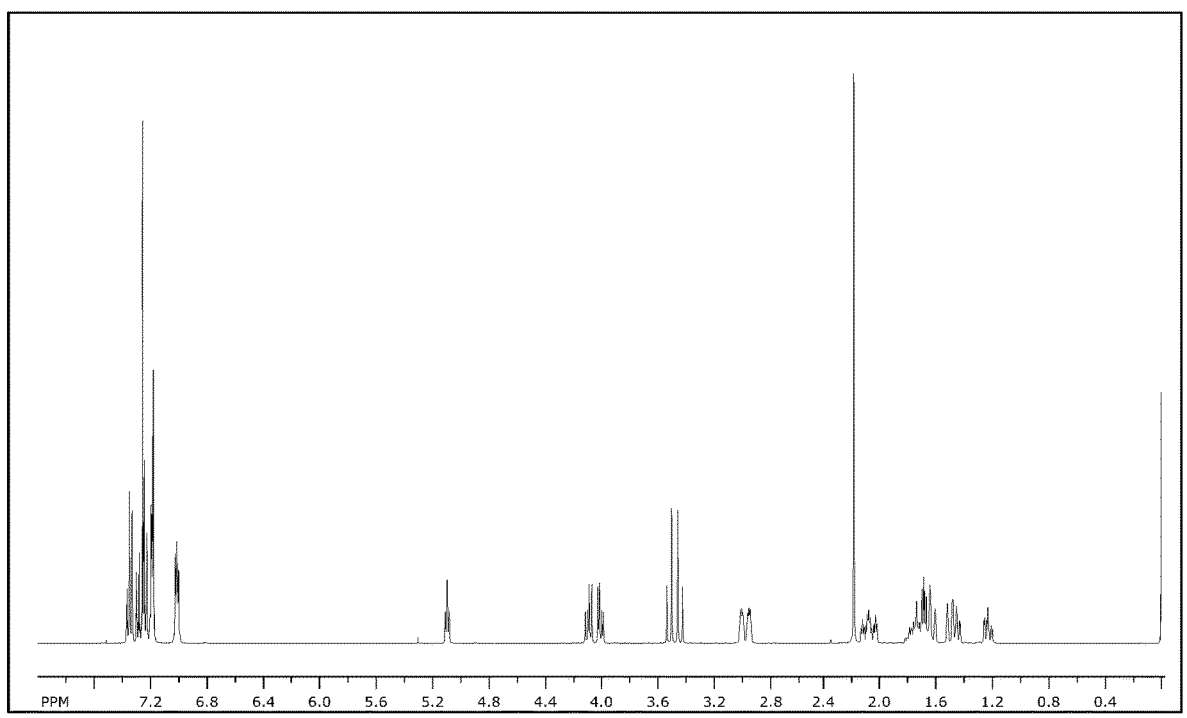
FIG. 13 is a $^1$H NMR spectrum of (1R,3r,5S)-8-Methyl-8-azabicyclo[3.2.1]octan-3-yl 2-benzyl-3-hydroxy-2-phenylpropanoate.

$^1$H NMR (400 MHz, CDCl$_3$) δ 7.39-7.16 (8H, m), 7.05-6.97 (2H, m), 5.09 (1H, t, J=5.3 Hz), 4.12-3.95 (2H, m), 3.54-3.42 (2H, m), 3.02-2.90 (2H, m), 2.19 (3H, s), 2.15-2.00 (2H, m), 1.84-1.58 (4H, m), 1.54-1.41 (2H, m), 1.28-1.19 (1H, m). The $^1$H NMR spectrum is shown in FIG. 13.

Figure 14:
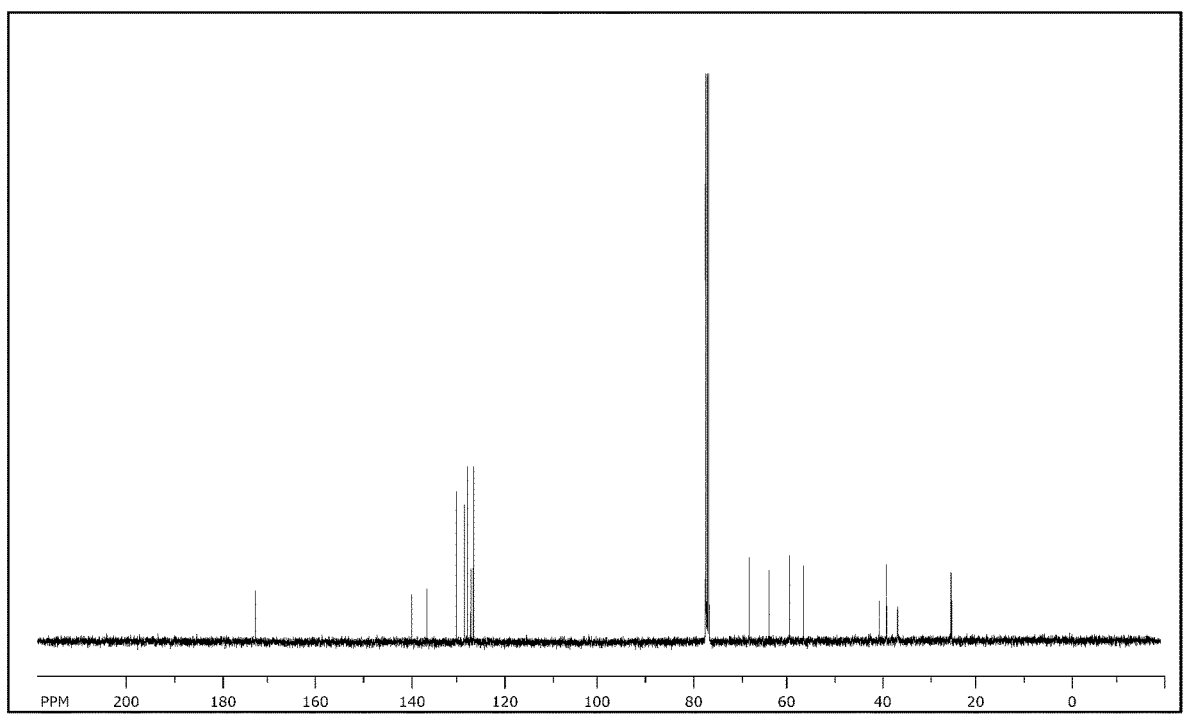
FIG. 14 is a $^{13}$C NMR spectrum of (1R,3r,5S)-8-Methyl-8-azabicyclo[3.2.1]octan-3-yl 2-benzyl-3-hydroxy-2-phenylpropanoate.

$^{13}$C NMR (400 MHz, CDCl$_3$) δ 173.3, 139.9, 136.7, 130.5, 128.7, 128.1, 127.4, 126.8, 126.7, 68.1, 63.9, 59.5 (×2 signals), 56.5, 40.4, 38.9, 36.5, 36.4, 25.2, 25.0 (The chiral centre leads to non-equivalence of the tropane ring carbon atoms, hence 20 signals, not 17 are observed). The $^{13}$C NMR spectrum is shown in FIG. 14.

LCMS (ESI) [M+H]$^+$ 380, R$_t$=0.90 min.
QC LCMS (ESI) [M+H]$^+$ 380.3, R$_t$=3.19 min. (99.2%)

Synthetic Scheme of Example 4: (1R,3r,5S)-8-Methyl-8-azabicyclo[3.2.1]octan-3-yl 3-hydroxy-2-methyl-2-(thiophen-2-yl) propanoate

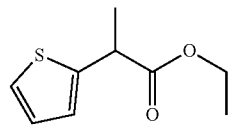

Ethyl 2-(thiophen-2-yl)propanoate

To a solution of diisopropylamine (4.5 mL, 32.3 mmol) in THF (100 mL) at −40° C. was added, dropwise, n-BuLi (12.9 mL, 2.5 M, 32.3 mmol). The reaction mixture was stirred at −40° C. for 20 min then cooled to −78° C. Ethyl 2-(thiophen-2-yl)acetate (5 g, 29.4 mmol) was added dropwise at such a rate that T<−60° C. The reaction mixture was stirred at −78° C. for 30 min then warmed to 0° C. Methyl iodide (2.2 mL, 35.3 mmol) was added and the reaction mixture stirred at 0° C. for 2 H. The reaction mixture was diluted with water and extracted with EtOAc. The combined organic fractions were washed with brine, dried (MgSO$_4$) and concentrated in vacuo. The resulting residue was purified on silica (80 g, 0-50% ethylacetate in cyclo-hexane) to yield the title compound as a pale brown oil (3.3 g, 62%). $^1$H NMR (400 MHz, CDCl$_3$) δ 7.20 (1H, t, J=3.4 Hz), 6.95 (2H, d, J=3.4 Hz), 4.22-4.12 (2H, m), 3.99 (1H, q, J=7.2 Hz), 1.58 (3H, d, J=7.1 Hz), 1.30-1.19 (3H, m).

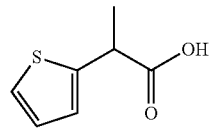

2-(Thiophen-2-yl)propanoic acid

To a solution of ethyl 2-(thiophen-2-yl)propanoate (5.9 g, 32.39 mmol) in methanol (40 mL) and water (15 mL) was added lithium hydroxide monohydrate (2.0 g, 48.4 mmol) and the reaction mixture stirred at RT for 3 H. The reaction mixture was concentrated in vacuo to approximately % volume and the residue extracted with EtOAc. The organic fractions were discarded and the aqueous layer was acidified to ~pH 3 with 1N HCl and extracted with EtOAc. The

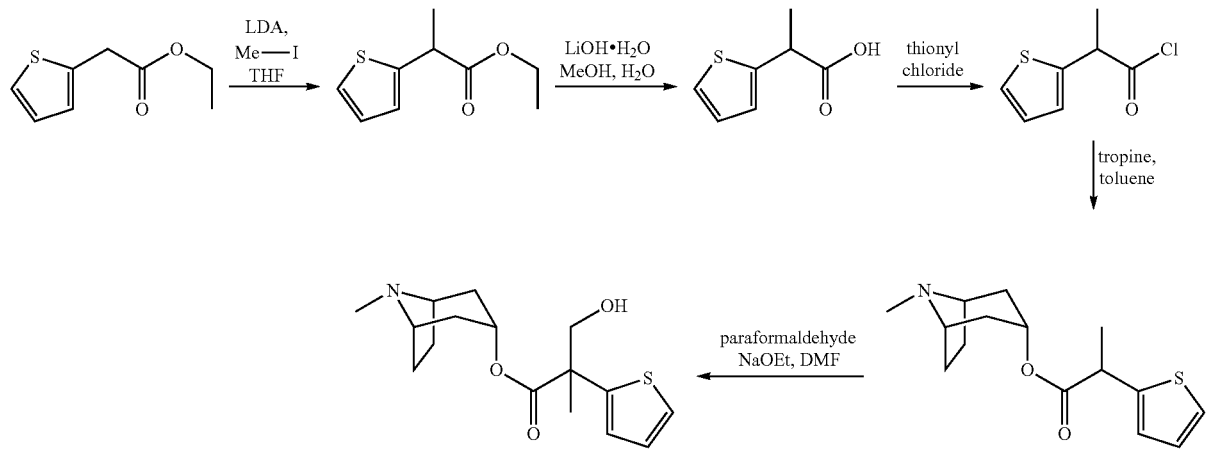

combined organic fractions were washed with brine, dried (MgSO$_4$) and concentrated in vacuo to yield the title compound as a yellow oil (5.0 g, 100%). $^1$H NMR (400 MHz, d$_6$-DMSO) δ 7.26 (1H, dd, J=5.2, 1.6 Hz), 6.89 (1H, dd, J=5.1, 3.5 Hz), 6.87-6.80 (1H, m), 3.74 (1H, q, J=7.0 Hz), 1.35 (3H, d, J=7.0 Hz).

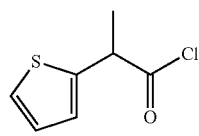

2-(Thiophen-2-yl)propanoyl chloride 2-(Thiophen-2-yl)propanoic acid (2.0 g, 12.8 mmol) was dissolved in thionyl chloride (10.0 mL, 137.1 mmol) and the reaction mixture heated at reflux for 2 H. The reaction mixture was concentrated in vacuo to give the title compound as a brown oil (2.24 g, 100%). $^1$H NMR (400 MHz, CDCl$_3$) δ 7.30 (1H, dd, J=5.1, 1.2 Hz), 7.06-6.99 (2H, m), 4.39 (1H, q, J=7.1 Hz), 1.70 (3H, d, J=7.1 Hz).

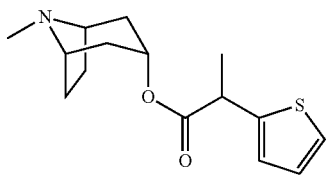 [SMILES: CC(C(=O)OC1CC2CCC(C1)N2C)c1cccs1]

(1R,3r,5S)-8-Methyl-8-azabicyclo[3.2.1]octan-3-yl 2-(thiophen-2-yl)propanoate

To a solution of 2-(thiophen-2-yl)propanoyl chloride (2.2 g, 12.6 mmol) in toluene (20 mL) was added tropine (1.62 g, 11.5 mmol) and the reaction mixture heated at 100° C. for 2 H. The reaction mixture was diluted with EtOAc and extracted with 1N HCl and the organic fraction discarded. The aqueous phase was made basic ~pH 12 with 6N NaOH and was extracted with EtOAc. The combined organic fractions were washed with brine, dried (MgSO$_4$) and concentrated in vacuo to give the title compound as a brown oil, which was used crude in the next reaction (2.29 g, 71%). LCMS (ESI) [M+H]$^+$ 280 R$_t$=0.72 min.

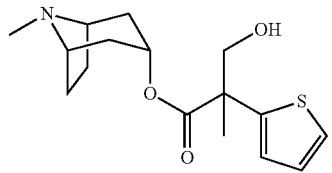 [SMILES: CN1C2CCC1CC(OC(=O)C(C)(CO)c1cccs1)C2]

Figure 15A:
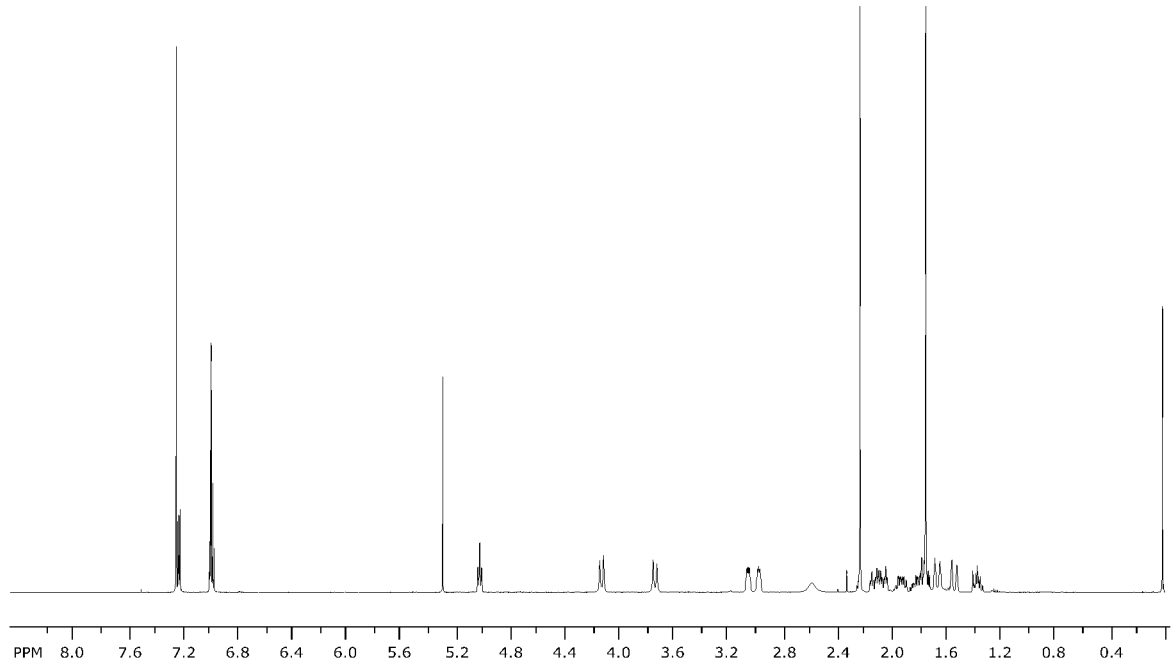
FIG. 15A is a $^1$H NMR spectrum of (1R,3r,5S)-8-Methyl-8-azabicyclo[3.2.1]octan-3-yl 3-hydroxy-2-methyl-2-(thiophen-2-yl) propanoate.
Figure 15B:
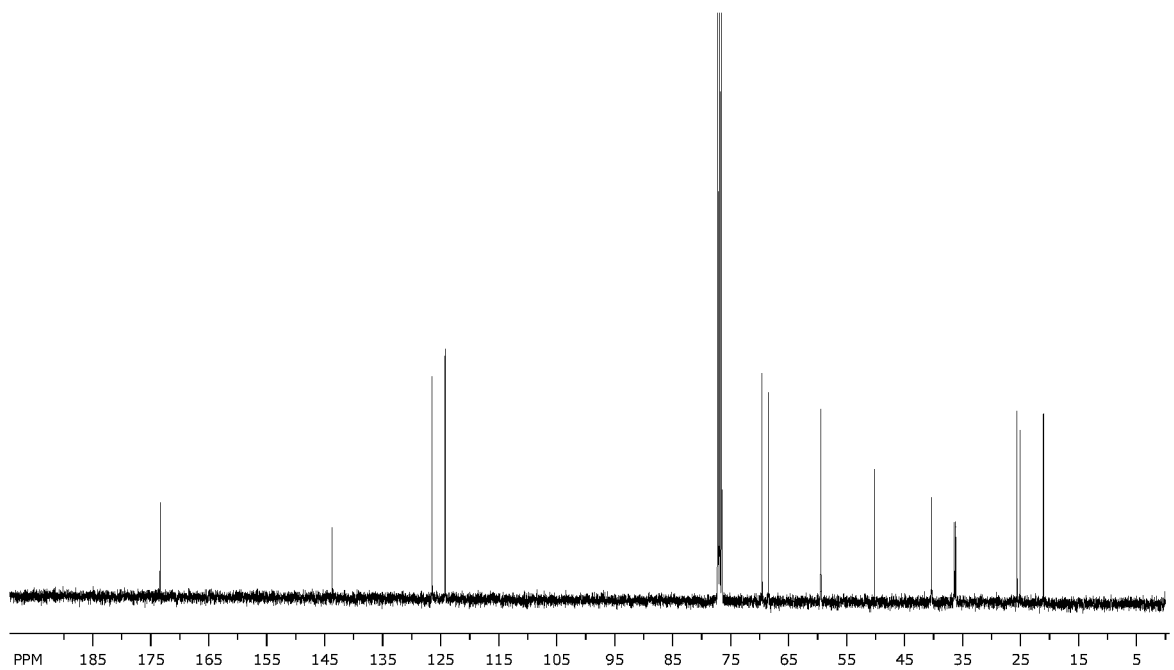
FIG. 15B is a $^{13}$C NMR spectrum of (1R,3r,5S)-8-Methyl-8-azabicyclo[3.2.1]octan-3-yl 3-hydroxy-2-methyl-2-(thiophen-2-yl) propanoate.

(1R,3r,5S)-8-Methyl-8-azabicyclo[3.2.1]octan-3-yl 3-hydroxy-2-methyl-2-(thiophen-2-yl) propanoate To a suspension of (1R,3r,5S)-8-methyl-8-azabicyclo[3.2.1]octan-3-yl 2-(thiophen-2-yl)propanoate (1.3 g, 4.7 mmol) and paraformaldehyde (0.21 g, 6.9 mmol) in DMF (10 mL) was added a solution of sodium ethoxide in ethanol (0.11 mL, 21%, 0.2 mmol) and the reaction mixture stirred at RT for 10 min. The reaction mixture was diluted with EtOAc and extracted with 1N HCl. The organic fractions were discarded. The aqueous fraction was made basic ~pH 12 with 1N NaOH and extracted with EtOAc. The combined organic fractions were washed with brine, dried (MgSO$_4$) and concentrated in vacuo to give the title compound as an off-white solid (760 mg, 52%). $^1$H NMR (400 MHz, CDCl$_3$) δ 7.24 (1H, dd, J=4.6, 1.4 Hz), 7.02-6.98 (2H, m), 5.03 (1H, t, J=5.54 Hz), 4.13 (1H, d, J=11.3 Hz), 3.74 (1H, d, J=11.3 Hz), 3.08-2.94 (2H, m), 2.58 (1H, br s), 2.22 (3H, s), 2.16-2.01 (1H, m), 1.98-1.87 (1H, m), 1.86-1.70 (5H, m), 1.69-1.62 (1H, m), 1.57-1.50 (1H, m), 1.41-1.31 (1H, m). The $^1$H NMR and $^{13}$C NMR spectra for the title compound are shown in FIG. 15A and FIG. 15B respectively.
LCMS (ESI) [M+H]$^+$ 310 R$_t$=2.40 min.

Synthetic Scheme of Example 5: (1R,3r,5S)-8-Methyl-8-azabicyclo[3.2.1]octan-3-yl3-hydroxy-2-(hydroxymethyl)-2-phenylpropanoate

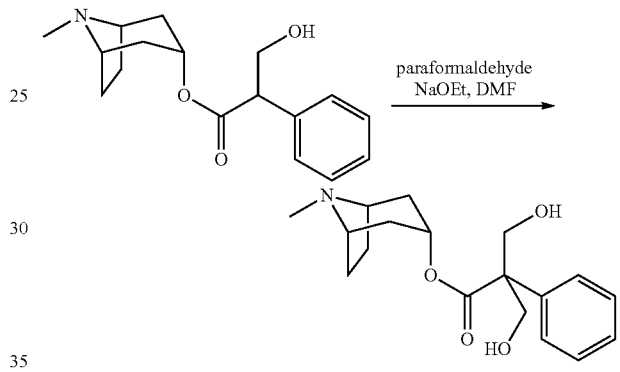

Figure 16A:
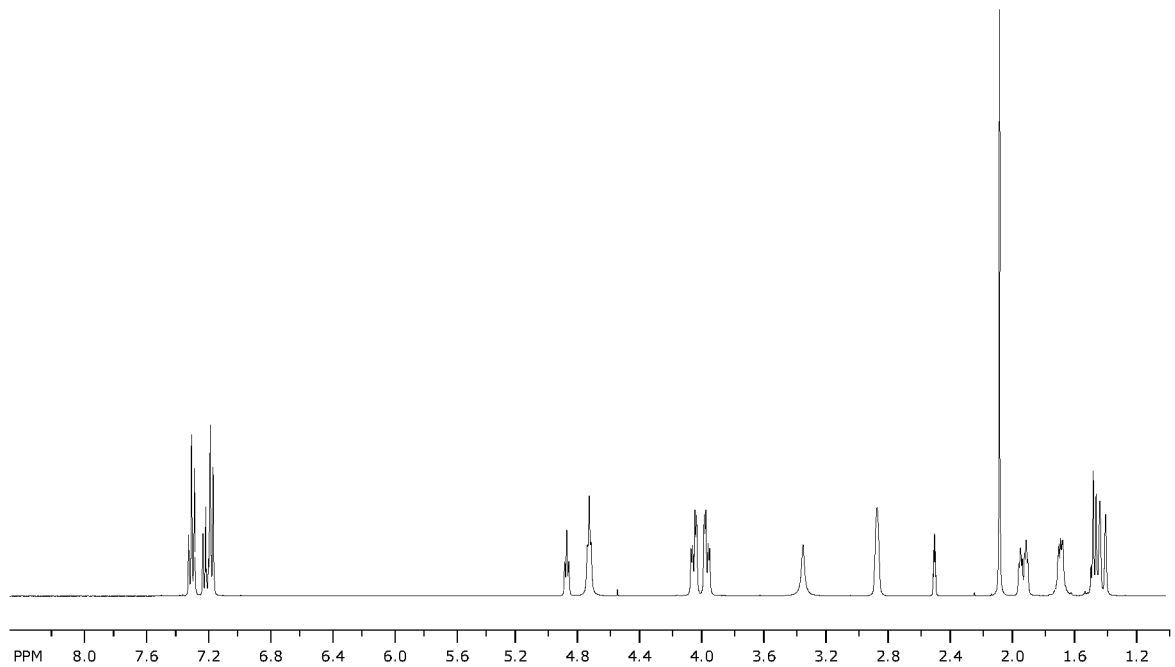
FIG. 16A is a $^1$H NMR spectrum of (1R,3r,5S)-8-Methyl-8-azabicyclo[3.2.1]octan-3-yl3-hydroxy-2-(hydroxymethyl)-2-phenylpropanoate.
Figure 16B:
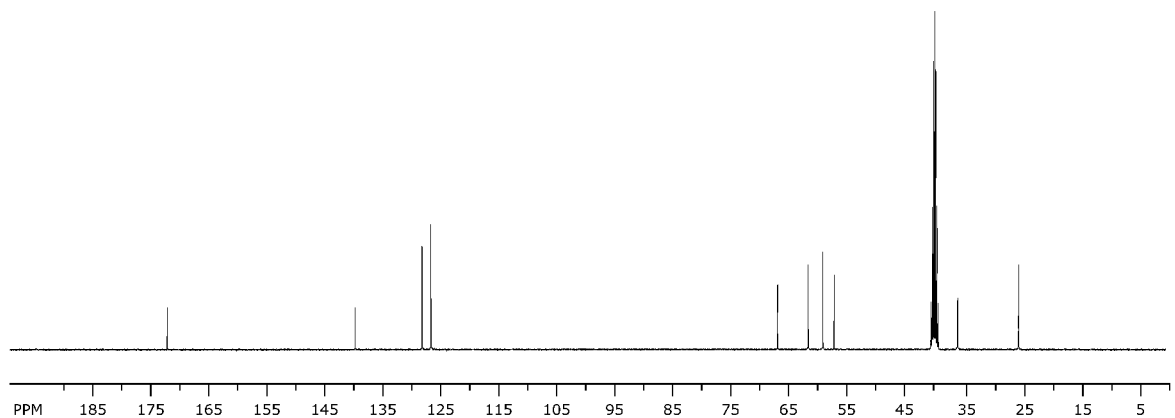
FIG. 16B is a $^{13}$C spectrum of (1R,3r,5S)-8-Methyl-8-azabicyclo[3.2.1]octan-3-yl3-hydroxy-2-(hydroxymethyl)-2-phenylpropanoate.

To a solution of atropine (3.1 g, 10.8 mmol) and paraformaldehyde (1.6 g, 54.1 mmol) in DMF (5 mL) at 0° C. was added sodium ethoxide in ethanol (0.08 mL, 21%, 0.22 mmol) and the reaction stirred at 0° C. for 5 min then at RT for 1 H. The reaction mixture was filtered through Celite and the filtrate purified on silica (24 g, 0-40% (2N NH$_3$ in MeOH) in DCM). Half of the material obtained was re-purified on C18 silica (50 g, 0-50% 0.02M NH$_3$ in MeCN) to give the title compound as an off-white solid (1.19 g, 67%). $^1$H NMR (400 MHz, d$_6$-DMSO) δ 7.35-7.27 (2H, m), 7.26-7.14 (3H, m), 4.88 (1H, t, J=5.1 Hz), 4.74 (1H, t, J=4.62 Hz), 4.06 (2H, dd, J=10.2, 4.9 Hz), 3.97 (2H, dd, J=10.2, 4.7 Hz), 3.35 (1H, s), 2.92-2.83 (2H, m), 2.07 (3H, s), 1.92 (2H, dt, J=14.4, 4.1 Hz), 1.75-1.60 (2H, m), 1.50-1.36 (4H, m). LCMS (ESI) [M+H]$^+$ 320 R$_t$=1.96 min. The $^1$H NMR and $^{13}$C NMR spectra for the title compound are shown in FIGS. 16A and 16B respectively Synthetic Scheme of Example 6: (1R,3r,5S)-8-Methyl-8-azabicyclo[3.2.1]octan-3-yl 2-(hydroxymethyl)-2-phenylbutanoate

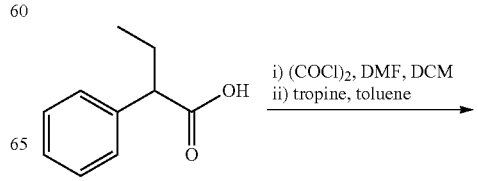

-continued

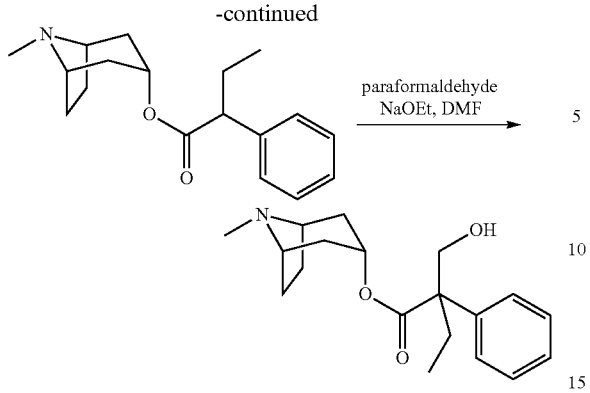

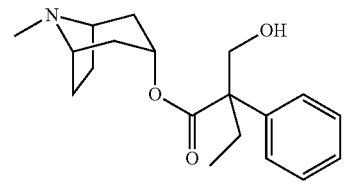

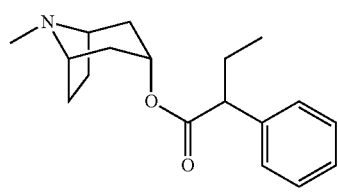 [SMILES: CCC(C(=O)OC1CC2CCC(C1)N2C)c1ccccc1]

(1R,3r,5S)-8-Methyl-8-azabicyclo[3.2.1]octan-3-yl 2-phenylbutanoate

To a solution of 2-phenylbutyric acid (2.0 g, 12.2 mmol) in DCM (20 mL) at 0° C. was added oxalyl chloride (2.1 mL, 24.4 mmol) and DMF (0.06 mL, 0.7 mmol). The reaction mixture was stirred at 0° C. for 30 min then at RT for 16 H. The reaction mixture was concentrated in vacuo and the residue dissolved in toluene (10 mL). This solution was added to a solution of tropine (1.7 g, 12.18 mmol) in toluene (20 mL) and the reaction mixture stirred at RT for 10 min then at reflux for 2 H. The reaction mixture was concentrated in vacuo and the residue collected by filtration and washed with diethyl ether. The solid was dissolved in 1N NaOH and extracted with DCM. The combined organic fractions were washed with brine, dried (MgSO$_4$) and concentrated in vacuo to give the title compound as a colourless oil (1.76 g, 50%). $^1$H NMR (400 MHz, CDCl$_3$) δ 7.35-7.21 (5H, m), 4.96 (1H, t, J=5.1 Hz), 3.41, (1H, t, J=7.8 Hz), 3.06-2.91 (2H, m), 2.21 (3H, s), 2.18-1.97 (3H, m), 1.94-1.70 (4H, m), 1.67-1.59 (1H, m), 1.52-1.36 (2H, m), 0.91 (3H, t, J=7.4 Hz). LCMS (ESI) [M+H]$^+$ 288 R$_t$=0.84 min.

Figure 17A:
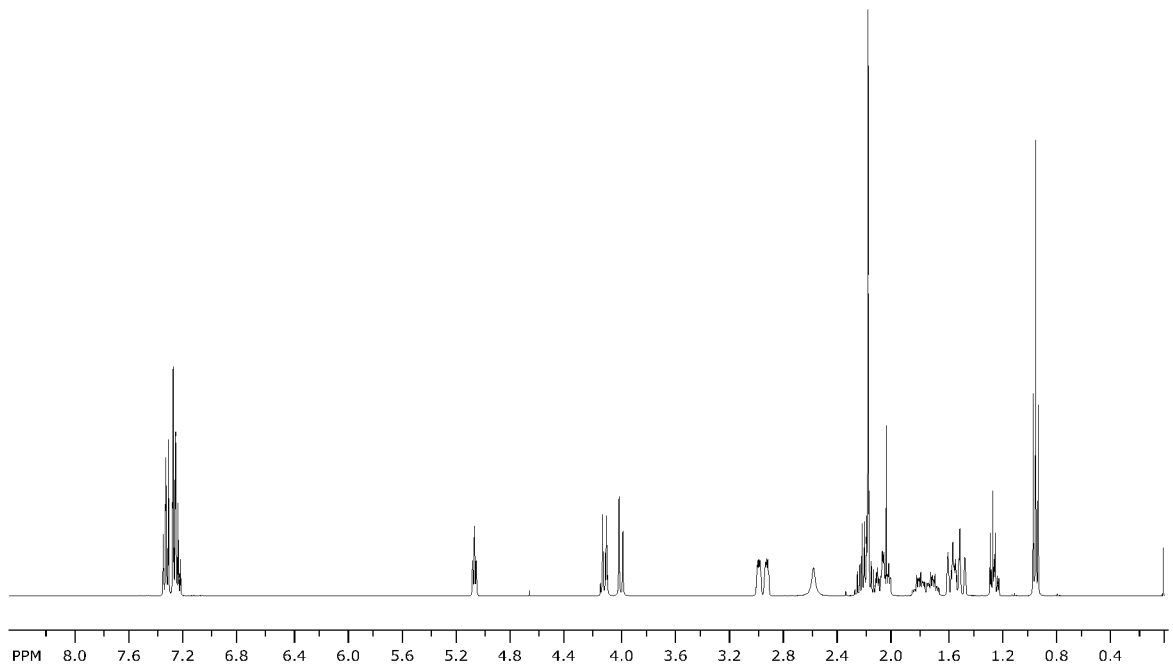
FIG. 17A is a $^1$H NMR spectrum of (1R,3r,5S)-8-Methyl-8-azabicyclo[3.2.1]octan-3-yl 2-(hydroxymethyl)-2-phenylbutanoate.
Figure 17B:
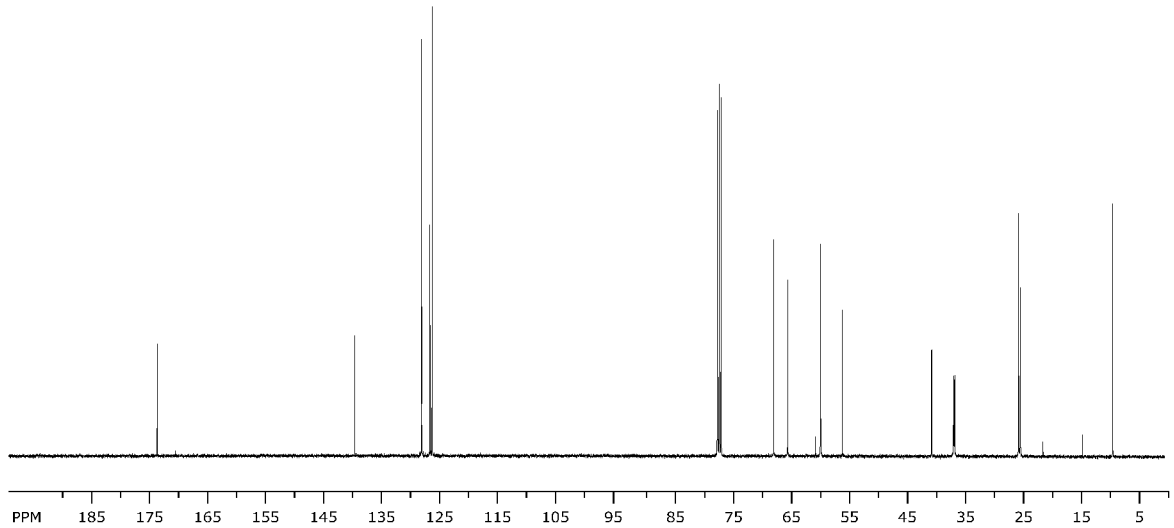
FIG. 17B is a $^{13}$C NMR spectrum of (1R,3r,5S)-8-Methyl-8-azabicyclo[3.2.1]octan-3-yl 2-(hydroxymethyl)-2-phenylbutanoate.

(1R,3r,5S)-8-Methyl-8-azabicyclo[3.2.1]octan-3-yl 2-(hydroxymethyl)-2-phenylbutanoate To a suspension of (1R,3r,5S)-8-methyl-8-azabicyclo[3.2.1]octan-3-yl 2-phenylbutanoate (1.8 g, 6.1 mmol) and paraformaldehyde (0.28 g, 9.2 mmol) in DMF (6 mL) was added a solution of sodium ethoxide in ethanol (0.11 mL, 21%, 0.2 mmol) and the reaction mixture stirred at RT for 4 H. The reaction mixture was diluted with EtOAc, extracted with 1N HCl and the organic fractions were discarded. The aqueous fraction was made basic ~pH 12 with 1N NaOH and extracted with EtOAc. The combined organic fractions were washed with brine, dried (MgSO$_4$) and concentrated in vacuo. The residue was purified on silica (50 g, 0-18% (2N NH$_3$ in MeOH in DCM) to give the title compound as an off-white solid (1.56 g, 80%). $^1$H NMR (400 MHz, CDCl$_3$) δ 7.38-7.21 (5H, m), 5.07 (1H, t, J=5.32 Hz), 4.12 (1H, d, J=11.1 Hz), 3.99 (1H, d, J=11.1 Hz), 3.02-2.88 (2H, m), 2.57 (1H, br s), 2.28-1.99 (7H, m), 1.86-1.64 (2H, m), 1.61-1.43 (3H, m), 1.29-1.20 (1H, m), 0.94 (3H, t, J=7.6 Hz). LCMS (ESI) [M+H]$^+$ 318 R$_t$=2.71 min. The $^1$H NMR and $^{13}$C NMR spectra for the title compound are shown in FIGS. 17A and 17B respectively.

Synthetic Scheme of Example 7: (1R,3r,5S)-8-Methyl-8-azabicyclo[3.2.1]octan-3-yl 3-cyclopropyl-2-(hydroxymethyl)-2-phenylpropanoate

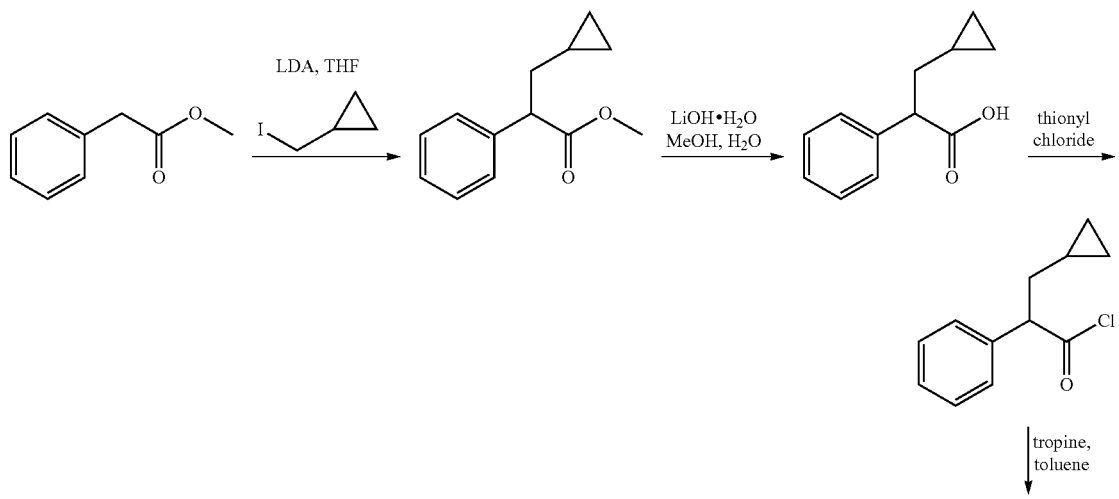

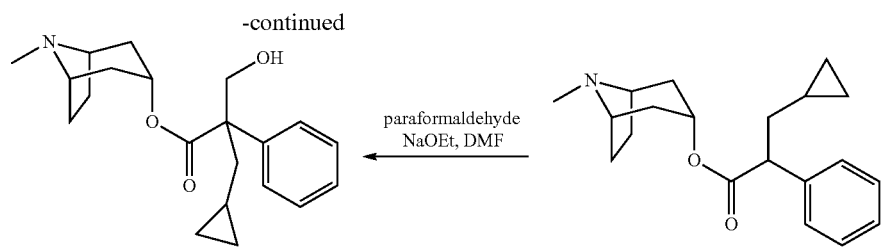

Methyl 3-cyclopropyl-2-phenylpropanoate

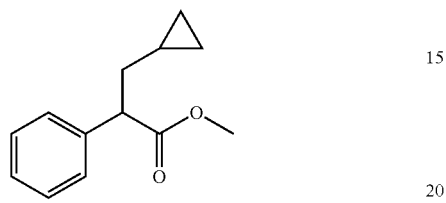

To a solution of methyl 2-phenylacetate (2 g, 13.3 mmol) in THF (50 mL) at −78° C. was added LDA (7.3 mL, 2M, 14.6 mmol) at such a rate that T<−60° C. The reaction mixture was stirred at −78° C. for 1 H. (Iodomethyl)cyclopropane (5 g, 27.5 mmol) in THF (10 mL) was added dropwise and the reaction mixture stirred at −78° C. for 30 min then warmed to RT and stirred for 3 H. The reaction mixture was diluted with water, extracted with EtOAc and the combined organic fractions were washed with brine, dried (MgSO₄) and concentrated in vacuo. The residue was purified on silica (40 g, 0-100% DCM in cyclo-hexane) to give the title compound as a yellow oil (2.6 g, 95%). ¹H NMR (400 MHz, CDCl₃) δ 7.35-7.20 (5H, m), 3.71-3.64 (4H, m), 1.94-1.84 (1H, m), 1.78-1.69 (1H, m), 0.67-0.56 (1H, m), 0.46-0.34 (2H, m), 0.13-0.00 (2H, m).

3-Cyclopropyl-2-phenylpropanoic acid

To a solution of methyl 3-cyclopropyl-2-phenylpropanoate (2.59 g, 12.7 mmol) in methanol (100 mL) and water (15 mL) was added lithium hydroxide monohydrate (1.33 g, 31.7 mmol) and the reaction mixture stirred at RT for 16 H. The reaction mixture was concentrated in vacuo to ~¼ volume, diluted with 1N HCl to ~pH 1 and the mixture extracted with EtOAc. The combined organic fractions were washed with brine, dried (MgSO₄) and concentrated in vacuo to give the title compound as a yellow oil (2.44 g, 100%). ¹H NMR (400 MHz, CDCl₃) δ 7.37-7.21 (5H, m), 3.67 (1H, t, J=8.0 Hz), 1.97-1.87 (1H, m), 1.79-1.69 (1H, m), 0.69-0.58 (1H, m), 0.47-0.38 (2H, m), 0.15-0.00 (2H, m).

3-Cyclopropyl-2-phenylpropanoyl chloride

To a solution of 3-cyclopropyl-2-phenylpropanoic acid (2.44 g, 12.8 mmol) in DCM (100 mL) was added DMF (0.01 mL) and oxalyl chloride (1.7 mL, 19.2 mmol) and the reaction mixture stirred at RT for 3 H. The reaction mixture was concentrated in vacuo to give the title compound as a pale yellow oil (2.68 g, 100%) used without purification. ¹H NMR (400 MHz, CDCl₃) δ 7.41-7.27 (5H, m), 4.10 (1H, t, J=7.3 Hz), 2.06-1.95 (1H, m), 1.86-1.77 (1H, m), 0.70-0.58 (1H, m), 0.52-0.38 (2H, m), 0.18-0.02 (2H, m).

(1R,3r,5S)-8-Methyl-8-azabicyclo[3.2.1]octan-3-yl 3-cyclopropyl-2-phenylpropanoate To a solution of tropine (2.68 g, 18.9 mmol) in toluene (20 mL) was added 3-cyclopropyl-2-phenylpropanoyl chloride (4.36 g, 20.8 mmol) and the reaction mixture was heated at reflux for 1.5 H. The reaction mixture was extracted with 1N HCl and the organic fraction discarded. The aqueous fraction was made basic ~pH 12 with 6N NaOH and extracted with ethylacatate. The combined organic fractions were washed with brine, dried (MgSO₄) and concentrated in vacuo to give the title compound as a yellow oil (1.76 g, 50%). ¹H NMR (400 MHz, CDCl₃) δ 7.35-7.20 (5H, m), 4.96 (1H, t, J=5.2 Hz), 3.63 (10H, t, J=7.4 Hz), 3.06-2.91 (2H, m), 2.22 (3H, s), 2.14-1.83 (4H, m), 1.82-1.70 (3H, m), 1.68-1.60 (1H, m), 1.52-1.38 (2H, m), 0.68-0.58 (1H, m), 0.47-0.35 (2H, m), 0.14-0.01 (2H, m).

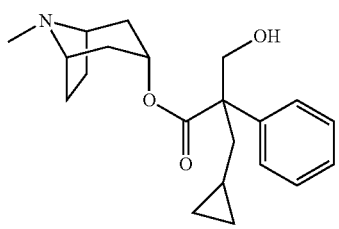 [SMILES: CN1C2CCC1CC(OC(=O)C(CO)(CC1CC1)c1ccccc1)C2]

Figure 18A:
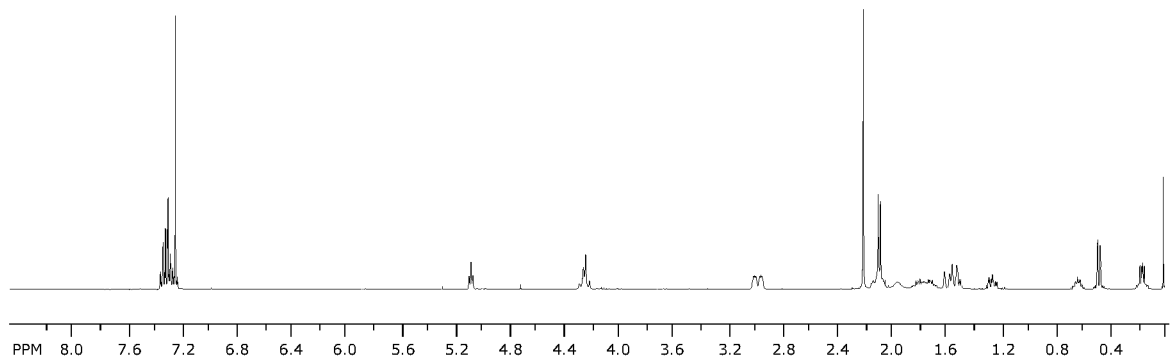
FIG. 18A is a $^1$H NMR spectrum of (1R,3r,5S)-8-methyl-8-azabicyclo[3.2.1]octan-3-yl 3-cyclopropyl-2-(hydroxymethyl)-2-phenylpropanoate.
Figure 18B:
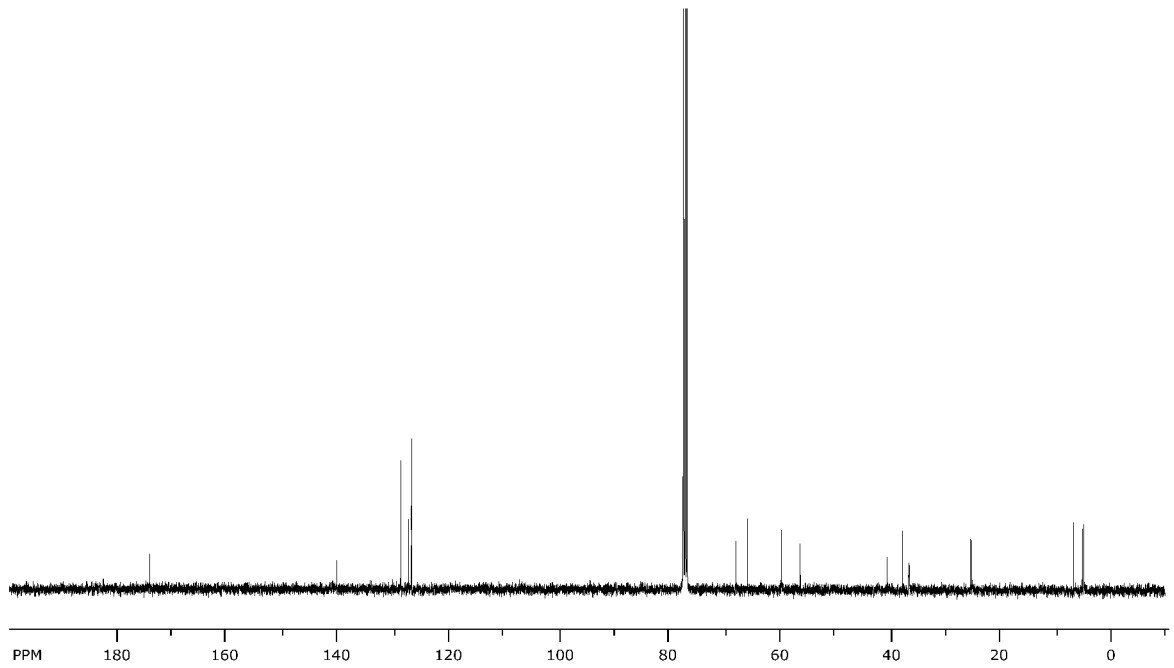
FIG. 18B is a $^{13}$C NMR spectrum of (1R,3r,5S)-8-methyl-8-azabicyclo[3.2.1]octan-3-yl 3-cyclopropyl-2-(hydroxymethyl)-2-phenylpropanoate.

(1R,3r,5S)-8-methyl-8-azabicyclo[3.2.1]octan-3-yl 3-cyclopropyl-2-(hydroxymethyl)-2-phenylpropanoate To a suspension of (1R,3r,5S)-8-methyl-8-azabicyclo[3.2.1]octan-3-yl 3-cyclopropyl-2-phenylpropanoate (1.76 g, 5.62 mmol) and paraformaldehyde (0.25 g, 8.42 mmol) in DMF was added sodium ethoxide in ethanol (0.07 mL, 4M, 1.12 mmol) and the reaction mixture stirred at 40° C. for 3 H. A further portion of sodium ethoxide (0.07 mL, 4M, 1.12 mmol) was added and the reaction mixture stirred at 40° C. for 16 H. The reaction mixture was diluted with EtOAc and extracted with 1N HCl. The organic fraction was discarded and the aqueous fraction made basic ~pH 12 with 6N NaOH. The mixture was extracted with EtOAc and the combined organic fractions washed with brine, dried (MgSO$_4$) and concentrated in vacuo. The resulting residue was purified on silica (40 g, 0-10% (7N NH$_3$ in MeOH) in DCM) to yield the title compound as an off-white solid (0.23 g, 12%). $^1$H NMR (400 MHz, CDCl$_3$) δ 7.39-7.22 (5H, m), 5.08 (1H, t, J=5.48 Hz), 4.31-4.19 (2H, m), 3.04-2.92 (2H, m), 2.20 (3H, s), 2.15-2.03 (3H, m), 1.87-1.65 (3H, m), 1.64-1.47 (4H, m), 1.31-1.20 (1H, m), 0.69-0.57 (1H, m), 0.52-0.39 (2H, m), 0.21-0.07 (2H, m). LCMS (ESI) [M+H]$^+$ 344 R$_t$=2.82 min. The $^1$H NMR and $^{13}$C NMR spectra for the title compound are shown in FIGS. 18A and 18B respectively.

Synthetic Scheme of Example 8: (1R,3r,5S)-8-Methyl-8-azabicyclo[3.2.1]octan-3-yl 3-fluoro-2-methyl-2-phenylpropanoate

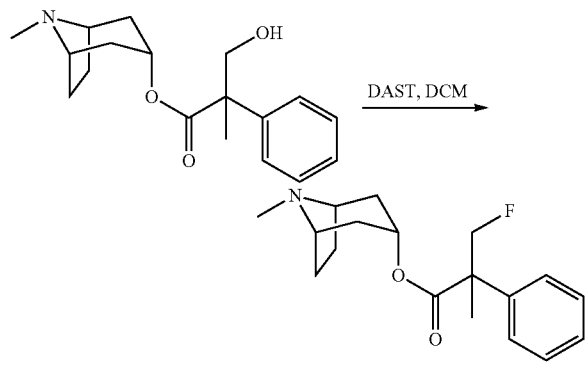

To a solution of (1R,3r,5S)-8-methyl-8-azabicyclo[3.2.1]octan-3-yl 3-hydroxy-2-methyl-2-phenyl propanoate (392 mg, 1.29 mmol) in DCM at 0° C. was added DAST (0.51 mL, 3.9 mmol) and the reaction mixture stirred at RT for 48 H. The reaction mixture was diluted with sat. aq. Na$_2$CO$_3$ solution and extracted with DCM. The combined organic fractions were dried (Na$_2$SO$_4$) and concentrated in vacuo.

Figure 19A:
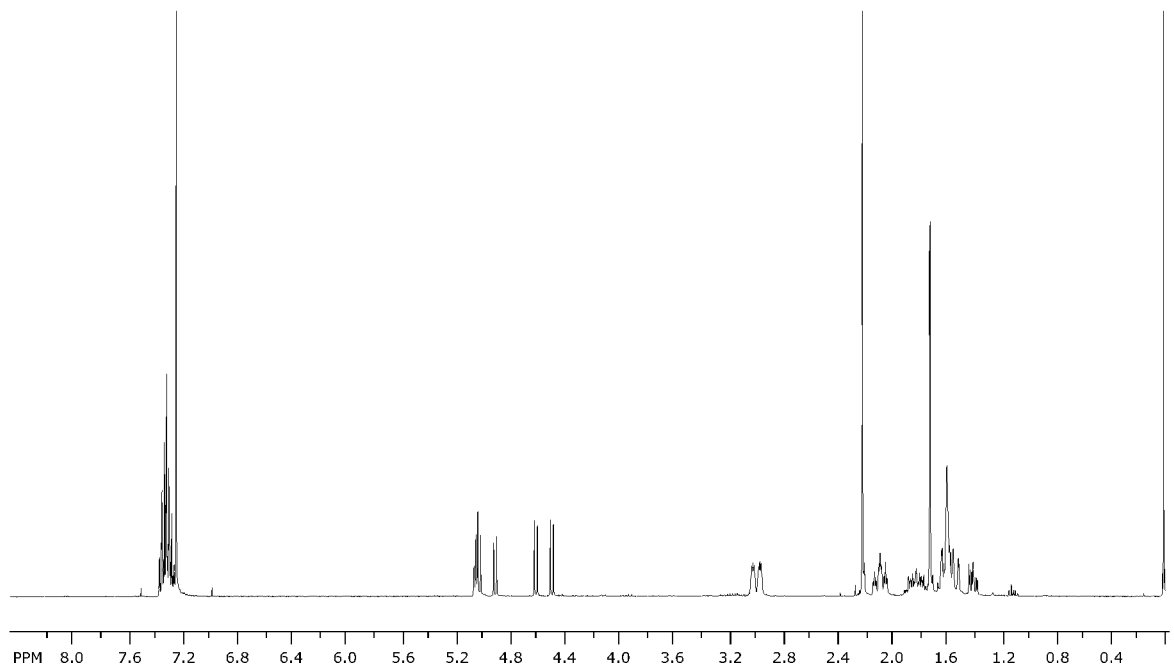
FIG. 19A is a $^1$H NMR spectrum of (1R,3r,5S)-8-Methyl-8-azabicyclo[3.2.1]octan-3-yl 3-fluoro-2-methyl-2-phenylpropanoate.
Figure 19B:
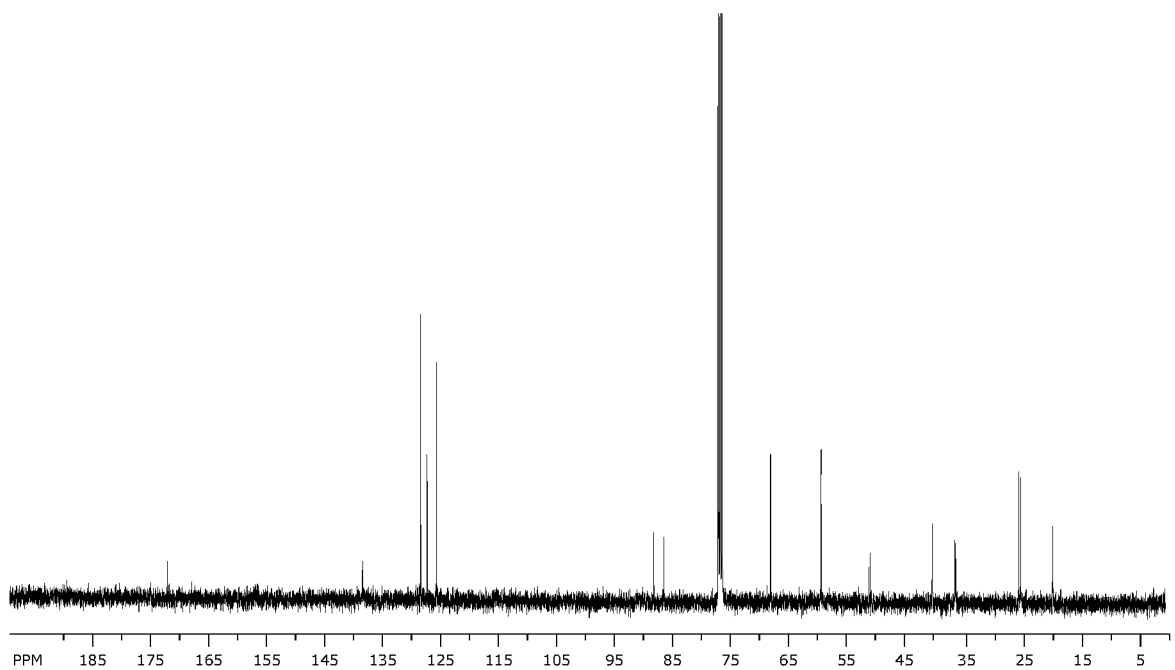
FIG. 19B is a $^{13}$C NMR spectrum of (1R,3r,5S)-8-Methyl-8-azabicyclo[3.2.1]octan-3-yl 3-fluoro-2-methyl-2-phenylpropanoate.

The resulting residue was purified on silica (4 g, 0-12% (2N NH$_3$ in MeOH) in DCM). The residue obtained was then purified by SFC (YMC Amylose-C, 15% MeOH+0.1% Et$_2$NH) to give the title compound as a pale yellow oil (26 mg, 6%). $^1$H NMR (400 MHz, CDCl$_3$) δ 7.39-7.27 (5H, m), 5.06 (1H, t, J=5.4 Hz), 4.97 (1H, dd, J=47.0, 8.7 Hz), 4.55 (1H, dd, J=47.0, 8.7 Hz), 3.05-2.94 (2H, m), 2.21 (3H, s), 2.14-2.01 (2H, m), 1.91-1.73 (2H, m), 1.72 (3H, d, J=2.1 Hz), 1.66-1.49 (4H, m). LCMS (ESI) [M+H]$^+$ 306 R$_t$=3.10 min. The $^1$H NMR and $^{13}$C NMR spectra for the title compound are shown in FIGS. 19A and 19B respectively.

Synthetic Scheme of Example 9: (1R,3r,5S)-8-Methyl-8-azabicyclo[3.2.1]octan-3-yl 4,4,4-trifluoro-2-(hydroxymethyl)-2-phenyl butanoate

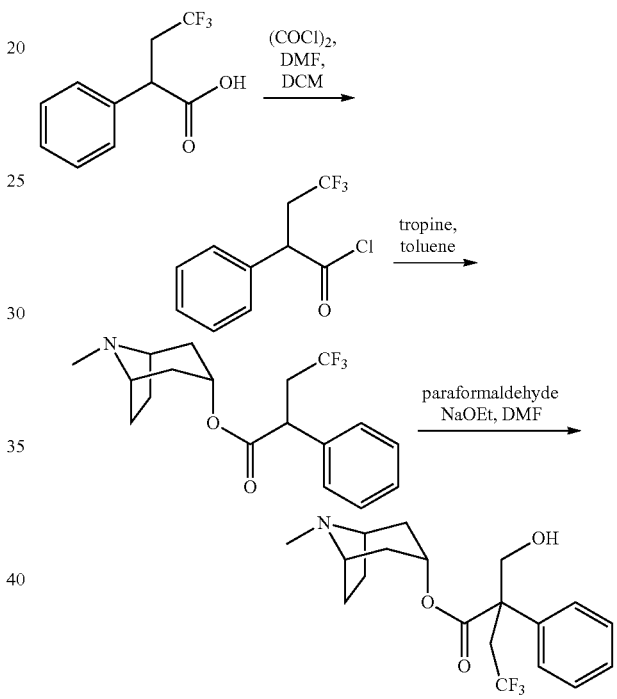

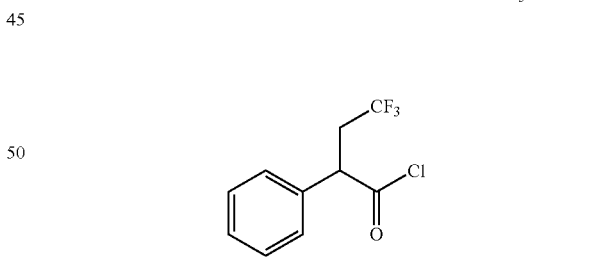

4,4,4-trifluoro-2-phenylbutanoyl chloride

To a solution of 4,4,4-trifluoro-2-phenylbutanoic acid (410 mg, 1.9 mmol) and DMF (0.1 mL) in DCM (25 mL) at 0° C. was added oxalyl chloride (0.33 mL, 3.8 mmol) and the reaction stirred at 0° C. for 1 H before stirring at RT for 16 H. The reaction mixture was concentrated in vacuo to give the product as a yellow oil (445 mg, 100%). $^1$H NMR (400 MHz, CDCl$_3$) δ 7.47-7.36 (3H, m), 7.33-7.27 (2H, m), 4.29 (1H, dd, J=10.2, 7.3 Hz), 3.24-3.05 (1H, m), 2.65-2.46 (1H, m).

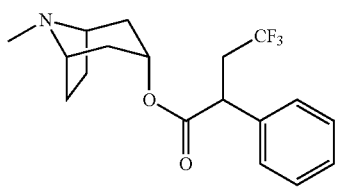 [SMILES: CN1C2CCC1CC(OC(=O)C(CC(F)(F)F)c1ccccc1)C2]

(1R,3r,5S)-8-Methyl-8-azabicyclo[3.2.1]octan-3-yl 4,4,4-trifluoro-2-phenylbutanoate To a solution of tropine (236 mg, 1.7 mmol) in toluene (7 mL) was added 4,4,4-trifluoro-2-phenylbutanoyl chloride (445 mg, 1.9 mmol) in toluene (3 mL) and the reaction mixture heated at reflux for 3 H. The reaction mixture was concentrated in vacuo and the residue triturated with diethyl ether. The solid was dissolved in 1N NaOH and extracted with DCM. The combined organic fractions were washed with brine, dried ($Na_2SO_4$) and concentrated in vacuo to give the title compound as a yellow solid (390 mg, 61%). $^1$H NMR (400 MHz, $CDCl_3$) δ 7.40-7.24 (5H, m), 4.97 (1H, t, J=5.5 Hz), 3.83 (1H, dd, J=8.7, 5.4 Hz), 3.21-3.07 (1H, m), 3.07-3.02 (1H, m), 2.95-2.89 (1H, m), 2.57-2.42 (1H, m), 2.21 (3H, s), 2.14-2.05 (1H, m), 2.05-1.85 (2H, m), 1.81-1.57 (3H, m), 1.46-1.39 (1H, m), 1.30-1.20 (1H, m). LCMS (ESI) [M+H]$^+$ 342 $R_t$=0.88 min.

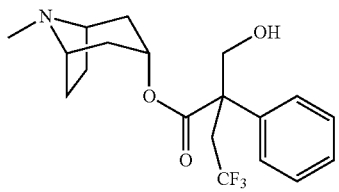 [SMILES: CN1C2CCC1CC(OC(=O)C(CO)(CC(F)(F)F)c1ccccc1)C2]

Figure 20A:
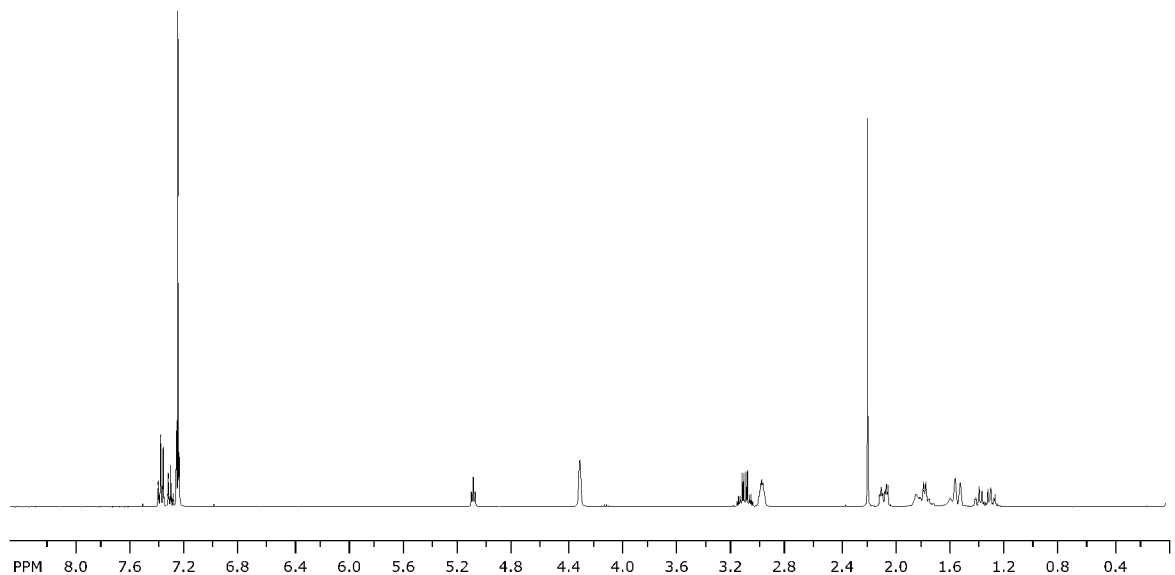
FIG. 20A is a ¹H NMR spectrum of (1R,3r,5S)-8-Methyl-8-azabicyclo[3.2.1]octan-3-yl 4,4,4-trifluoro-2-(hydroxymethyl)-2-phenylbutanoate.
Figure 20B:
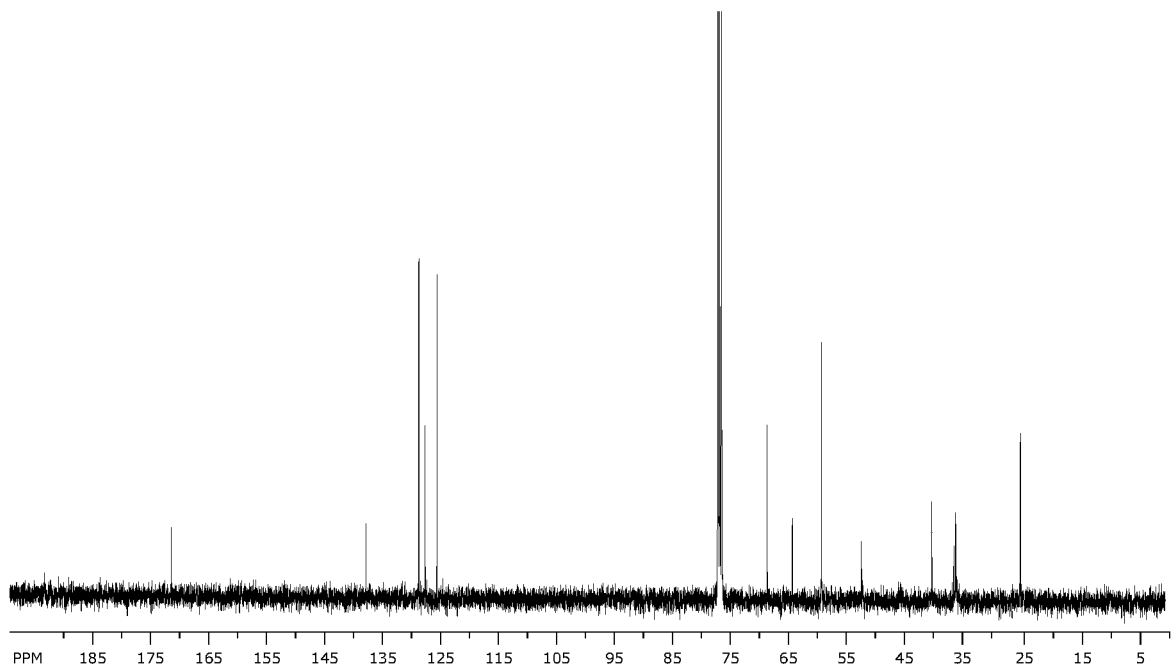
FIG. 20B is a ¹³C NMR spectrum of (1R,3r,5S)-8-Methyl-8-azabicyclo[3.2.1]octan-3-yl 4,4,4-trifluoro-2-(hydroxymethyl)-2-phenylbutanoate.

(1R,3r,5S)-8-Methyl-8-azabicyclo[3.2.1]octan-3-yl 4,4,4-trifluoro-2-(hydroxymethyl)-2-phenylbutanoate To a suspension of (1R,3r,5S)-8-methyl-8-azabicyclo[3.2.1]octan-3-yl 4,4,4-trifluoro-2-phenylbutanoate (390 mg, 1.1 mmol) and paraformaldehyde (51 mg, 1.7 mmol) in DMF (3 mL) was added sodium ethoxide in ethanol (0.3 mL, 0.2 M, 0.06 mmol) and the reaction stirred at RT for 2 H. More paraformaldehyde (40 mg, 1.3 mmol) and sodium ethoxide in ethanol (0.15 mL, 1.5 M, 0.2 mmol) were added and the reaction stirred at RT for 16 H. The reaction mixture was diluted with water, extracted with DCM and the combined organic fractions were washed with brine, dried ($Na_2SO_4$) and concentrated in vacuo. The resulting residue was purified on silica (12 g, 0-10% (2N $NH_3$ in MeOH) in DCM) to give the title compound as a white solid (105 mg, 24%). $^1$H NMR (400 MHz, $CDCl_3$) δ 7.44-7.23 (5H, m), 5.09 (1H, t, J=5.4 Hz), 4.31 (2H, br s), 3.17-3.03 (2H, m), 3.02-2.93 (2H, m), 2.19 (3H, s), 2.12-2.03 (2H, m), 1.88-1.69 (3H, m), 1.64-1.48 (2H, m), 1.42-1.23 (2H, m). LCMS (ESI) [M+H]$^+$ 372 $R_t$=2.95 min. The $^1$H NMR and $^{13}$C NMR spectra for the title compound are shown in FIGS. 20A and 20B respectively.

Synthetic Scheme of Example 10: (1R,3r,5S)-8-Methyl-8-azabicyclo[3.2.1]octan-3-yl 2,3-dihydroxy-2-phenylpropanoate

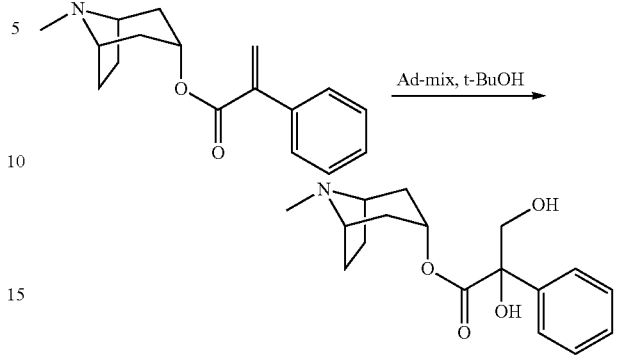

A solution of AD-mix-alpha (1.3 g) in a mixture of water (5.0 mL) and tert-butanol (5 mL) was stirred at room temperature for 15 min to give a clear yellow solution that was cooled with an ice-water bath to approximately 0° C. A solution of (1R,3r,5S)-8-methyl-8-azabicyclo[3.2.1]octan-3-yl 2-phenylacrylate (250 mg, 0.921 mmol) in tert-butanol (1.0 mL) was added, and the resulting solution stirred at 0° C. for 3 H, then allowed to warm to RT overnight. The reaction mixture was treated with excess $Na_2SO_3$ then partitioned between water and DCM. The aqueous layer was separated and further extracted with DCM and the combined organic extracts washed with brine, dried ($Na_2SO_4$) and concentrated in vacuo. The resulting residue was purified on silica (12 g, 0-10% (2N $NH_3$ in MeOH) in DCM) to give enantiomerically enriched (1R,3r,5S)-8-methyl-8-azabicyclo[3.2.1]octan-3-yl 2,3-dihydroxy-2-phenylpropanoate as a gum (110 mg, 39%).

In a separate procedure, a solution of AD-mix-beta (1.3 g) in a mixture of water (5.0 mL) and tert-butanol (5 mL) was stirred at room temperature for 15 min to give a clear yellow solution that was cooled with an ice-water bath to approximately 0° C. A solution of (1R,3r,5S)-8-methyl-8-azabicyclo[3.2.1]octan-3-yl 2-phenylacrylate (250 mg, 0.921 mmol) in tert-butanol (1.0 mL) was added, and the resulting solution stirred at 0° C. for 3 H, then allowed to warm to RT overnight. The reaction mixture was treated with excess $Na_2SO_3$ then partitioned between water and DCM. The aqueous layer was separated and further extracted with DCM and the combined organic extracts washed with brine, dried ($Na_2SO_4$) and concentrated in vacuo. The resulting residue was purified on silica (12 g, 0-10% (2N $NH_3$ in MeOH) in DCM) to give enantiomerically enriched (1R,3r,5S)-8-methyl-8-azabicyclo[3.2.1]octan-3-yl 2,3-dihydroxy-2-phenylpropanoate of opposite enantiomeric enrichment as a gum (126 mg, 45%).

Figure 21A:
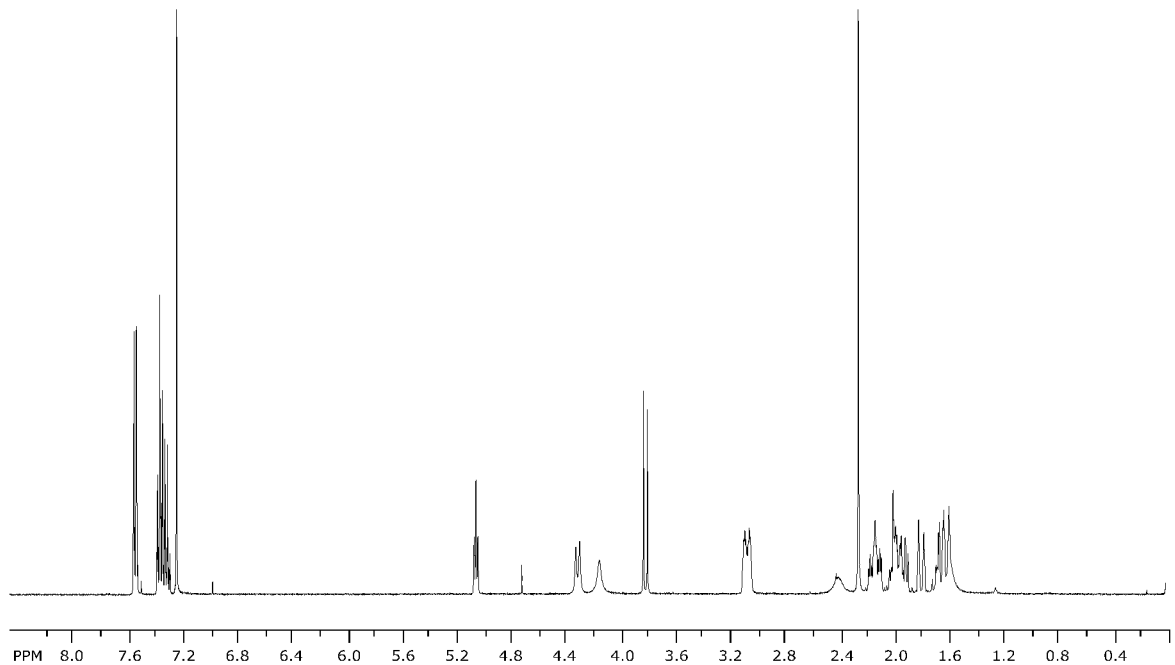
FIG. 21A is a ¹H NMR spectrum of (1R,3r,5S)-8-Methyl-8-azabicyclo[3.2.1]octan-3-yl 2,3-dihydroxy-2-phenylpropanoate.
Figure 21B:
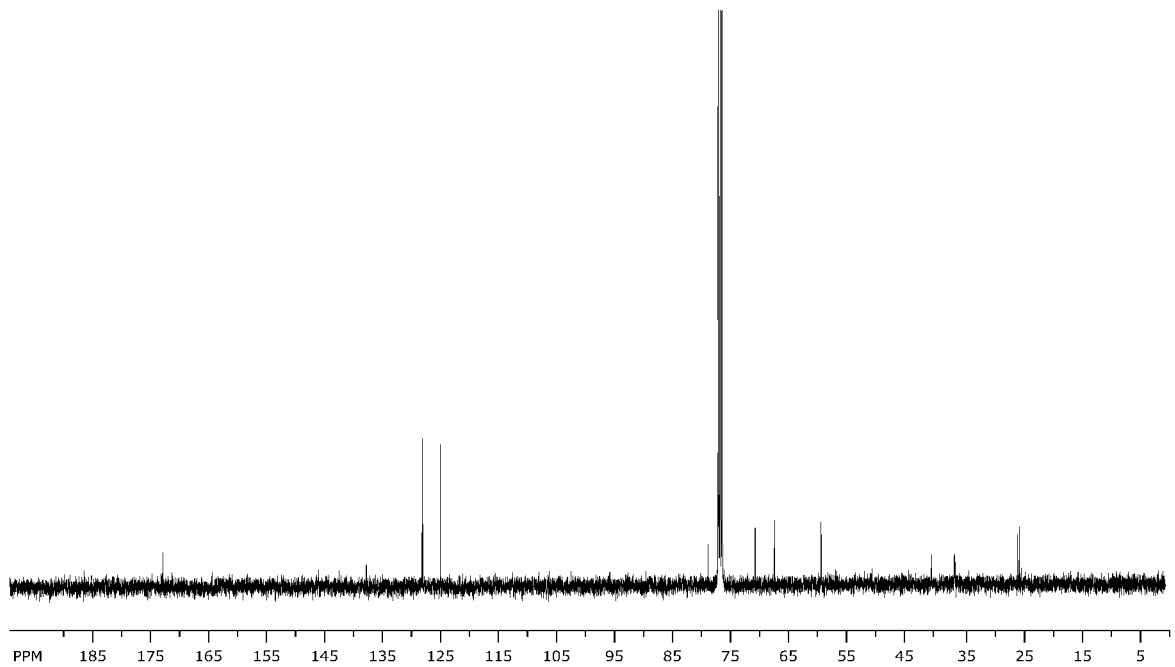
FIG. 21B is a ¹³C NMR spectrum of (1R,3r,5S)-8-Methyl-8-azabicyclo[3.2.1]octan-3-yl 2,3-dihydroxy-2-phenylpropanoate.

A portion of the AD-mix-alpha reaction product (95 mg, 0.311 mmol) was dissolved in acetonitrile (1 mL) to give a clear solution. Similarly, a portion of the AD-mix-beta reaction product (95 mg, 0.311 mmol) was separately dissolved in acetonitrile (1.0 mL) to also give a clear solution. The two solutions of opposite enantiomeric enrichment were then combined, diluted with water (2.0 mL) and freeze dried to give the racemic title compound as a white solid (190 mg). $^1$H NMR (400 MHz, $CDCl_3$) δ 7.60-7.53 (2H, m), 7.42-7.30 (3H, m), 5.06 (1H, t, J=5.5 Hz), 4.32 (1H, d, J=11.5 Hz), 4.16 (1H, br s), 3.82 (1H, d, J=11.5 Hz), 3.13-3.03 (2H, m), 2.41 (1H, br s), 2.26 (3H, s), 2.20-2.07 (2H, m), 2.06-1.88 (3H, m), 1.84-1.76 (1H, m), 1.71-1.1.53 (2H, m). LCMS (ESI) [M+H]$^+$ 306.2 $R_t$=1.97 min. The $^1$H NMR and $^{13}$C NMR spectra for the title compound are shown in FIGS. 21A and 21B respectively.

Synthetic Scheme of Example 11: (1R,3r,5S)-8-Methyl-8-azabicyclo[3.2.1]octan-3-yl 3-methoxy-2-methyl-2-phenylpropanoate

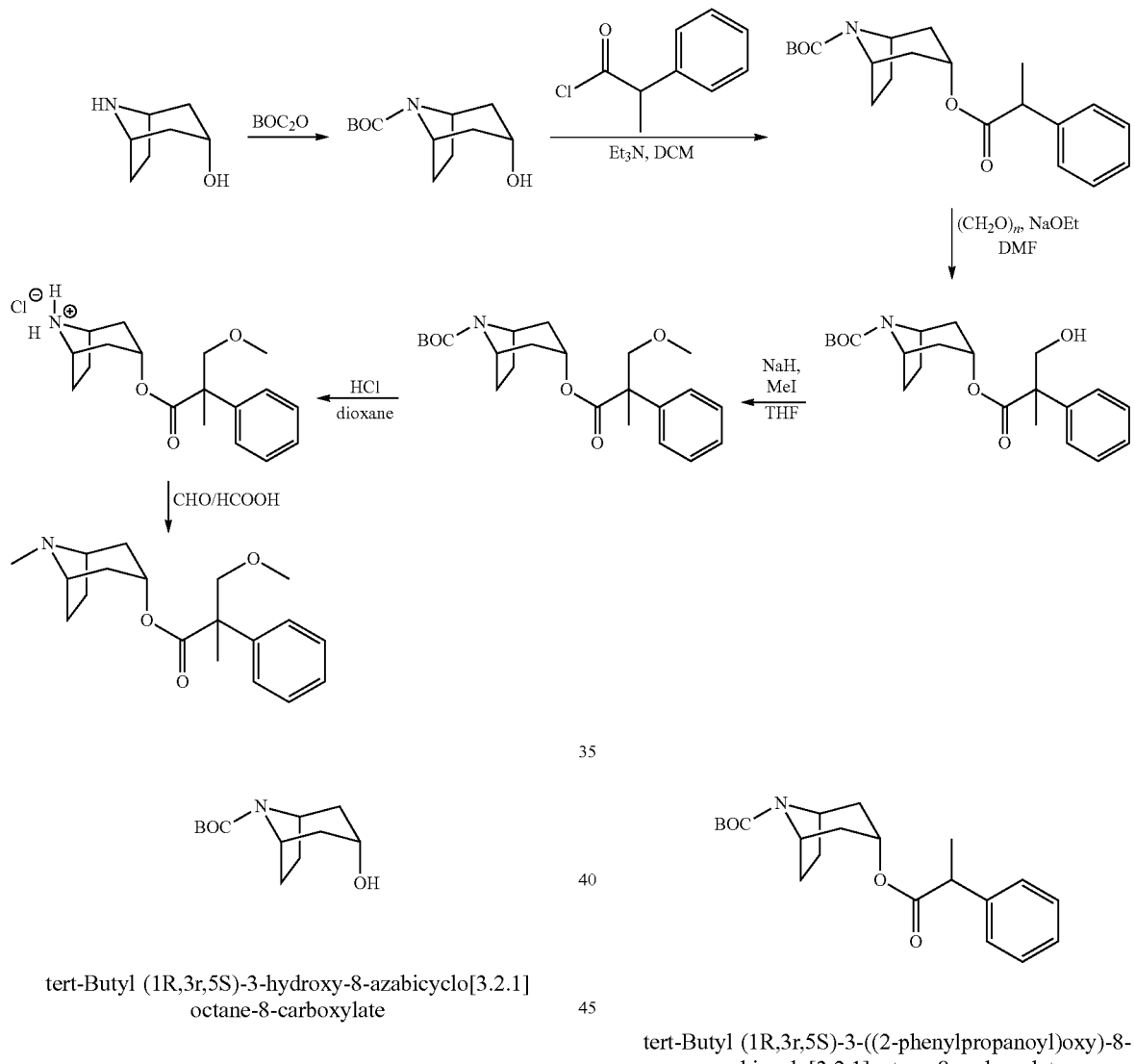

tert-Butyl (1R,3r,5S)-3-hydroxy-8-azabicyclo[3.2.1]octane-8-carboxylate tert-Butyl (1R,3r,5S)-3-((2-phenylpropanoyl)oxy)-8-azabicyclo[3.2.1]octane-8-carboxylate A stirred solution of nortropine (12.72 g, 100 mmol) in DCM (150 mL) was treated with triethylamine (27.9 mL, 20.24 g, 200 mmol) and cooled to in ice. Solid di-tert-butyl dicarbonate (32.74 g, 150.0 mmol) was then added over 10 min and the addition vessel washed DCM (50 mL). A vigorous gas evolution was observed, and the resulting mixture stirred for 2 H while warming to RT and then at RT for 16 H. The resulting mixture was diluted DCM (100 mL), washed 10% citric acid (aq) soln, brine (50 mL) and the layers separated. The combined organic fractions were dried (Na$_2$SO$_4$), filtered and conc. in vacuo to give a cream solid. The solid residue was triturated with diethyl ether (30 mL) and sonicated to give a free flowing solid collected by filtration, 19.67 g (86%). $^1$H NMR (400 MHz, CDCl$_3$) δ 4.29-4.06 (3H, m), 2.26-1.87 (6H, m), 1.75-1.65 (2H, m), 1.55 (1H, d, J=1.5 Hz), 1.45 (9H, s). LCMS (ESI) [M+H]$^+$ not observed R$_t$=1.21 min.

A solution 2-phenylpropionyl chloride (8.20 g, 48.63 mmol) in toluene (50 mL) was added to a stirred mixture of tert-butyl (1R,3r,5S)-3-hydroxy-8-azabicyclo[3.2.1]octane-8-carboxylate (10.05 g, 44.21 mmol) and triethylamine (12.3 ml, 8.95 g, 88.42 mmol) in toluene (50 mL). The resulting suspension was heated at reflux with vigorous stirring for 24 H giving the product as an off-white suspension. The reaction mixture was cooled to RT and diluted with EtOAc (100 mL) and H$_2$O (100 mL). The aqueous layer was separated and further extracted EtOAc (2×100 mL). The combined extracts were washed with 5% citric acid (aq) soln, sat. NaHCO$_3$ (aq) and brine, dried (Na$_2$SO$_4$), filtered and conc. in vacuo. To give the title compound (16.21 g, 102%). $^1$H NMR (400 MHz, CDCl$_3$) δ 7.37-7.22 (5H, m), 5.06 (1H, t, J=5 Hz), 4.24-3.90 (2H, m), 3.68 (1H, q, J=7 Hz), 2.23-1.90 (2H, m), 1.86-1.57 (5H, m), 1.54-1.46 (1H, m), 1.52 (3H, d, J=7 Hz), 1.43 (9H, s), 1.38-1.27 (1H, m). LCMS (ESI) [M+H]$^+$ not observed R$_t$=1.98 min.

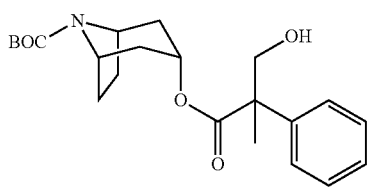 [SMILES: CC(C)(C)OC(=O)N1C2CCC1CC(OC(=O)C(C)(CO)c1ccccc1)C2]

tert-Butyl (1R,3r,5S)-3-((3-hydroxy-2-methyl-2-phenylpropanoyl)oxy)-8-azabicyclo[3.2.1]octane-8-carboxylate A stirred slurry of tert-butyl (1R,3r,5S)-3-((2-phenylpropanoyl)oxy)-8-azabicyclo[3.2.1]octane-8-carboxylate (7.19 g, 20.0 mmol) in DMF (15 mL) was treated paraformaldehyde (0.90 g, 30 mmol) followed by 21% sodium ethoxide solution, (0.37 mL, 1.00 mmol) and stirred at RT for 18 H. A second portion 21% sodium ethoxide solution, (0.37 ml, 1.00 mmol) was added and stirring continued for further 2 H. LCMS indicates shifted peak but no mass ion. The reaction mixture was diluted DCM (200 mL), washed with water and brine. The organic layer was separated, dried ($Na_2SO_4$), filtered and conc. in vacuo to give the crude product as yellow oil. The residue was purified on silica (120 g, 0-50% EtOAc in cyclo-hexane) to give the title compound as white solid, (5.29 g, 68%). $^1$H NMR (400 MHz, $CDCl_3$) δ 7.39-7.24 (5H, m), 5.16 (1H, t, J=5 Hz), 4.14 (1H, dd, J=6, 11 Hz), 4.19-3.89 (2H, m), 3.62 (1H, dd, J=8, 11 Hz), 2.43 (1H, dd, J=6, 8 Hz), 2.29-1.91 (2H, m), 1.84-1.70 (1H, m), 1.70 (3H, s), 1.70-1.46 (4H, m), 1.43 (9H, s), 1.25-1.08 (1H, m). LCMS (ESI) [M+H-Boc]$^+$ 290, $R_t$=1.60 min.

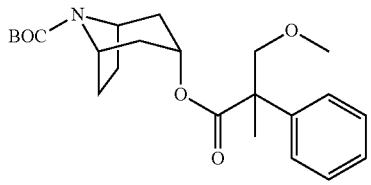 [SMILES: COCC(C)(C(=O)OC1CC2CCC(C1)N2C(=O)OC(C)(C)C)c1ccccc1]

tert-Butyl (1R,3r,5S)-3-((3-methoxy-2-methyl-2-phenylpropanoyl)oxy)-8-azabicyclo[3.2.1]octane-8-carboxylate A stirred suspension of sodium hydride (0.24 g, 60%, 6.01 mmol) in dry THF (10 ml) was cooled to 0° C. and a solution of tert-butyl (1R,3r,5S)-3-((3-hydroxy-2-methyl-2-phenylpropanoyl)oxy)-8-azabicyclo[3.2.1] octane-8-carboxylate (1.95 g, 5.01 mmol) in dry THF (10 mL) was added dropwise. The resulting mixture stirred for 1 H at 0° C. and then the reaction mixture was cooled to −6° C. and methyl iodide (0.34 mL, 5.5 mmol) was added. The mixture was allowed to warm slowly to RT over 3 H. The reaction mixture was quenched by addition of aq. $NH_4Cl$ (20 ml) and extracted with EtOAc. The combined organic extracts were washed with brine, dried ($Na_2SO_4$) and conc. in vacuo. The residue was purified on silica (80 g, 0-25% EtOAc in cyclo-hexane) to give the title compound as colourless syrup, (1.54 g, 76%). $^1$H NMR (400 MHz, $CDCl_3$) δ 7.37-7.21 (5H, m), 5.12 (1H, t, J=5.3 Hz), 4.19-3.94 (2H, m), 3.99 (1H, d, J=8.7 Hz), 3.62 (1H, d, J=8.7 Hz), 3.387 (3H, s), 2.23-1.93 (2H, m), 1.80-1.66 (2H, m), 1.65 (3H, s), 1.62-1.45 (4H, m), 1.43 (9H, s). LCMS (ESI) [M+H-Boc]$^+$ 304, $R_t$=1.81 min.

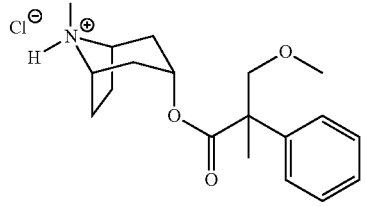

(1R,3r,5S)-8-Azabicyclo[3.2.1]octan-3-yl 3-methoxy-2-methyl-2-phenylpropanoate hydrochloride To a stirred solution of tert-butyl (1R,3r,5S)-3-((3-methoxy-2-methyl-2-phenylpropanoyl)oxy)-8-azabicyclo[3.2.1]octane-8-carboxylate (1.10 g, 2.73 mmol) in dioxane (2.0 mL) was added 4N HCl soln in dioxane (2.0 mL) and the reaction mixture stirred at RT for 20 H. The reaction mixture was concentrated in vacuo to give the crude product as colourless syrup (1.18 g, 100%), which was used without purification. $^1$H NMR (400 MHz, $CDCl_3$) δ 9.47 (2H, br s), 7.38-7.21 (5H, m), 5.10 (1H, t, J=4.5 Hz), 3.99 (1H, d, J=8.7 Hz), 3.93-3.83 (2H, m), 3.60 (1H, d, J=8.7 Hz), 3.37 (3H, s), 2.59-2.45 (2H, m), 2.04-1.54 (6H, m), 1.64 (3H, s). LCMS (ESI) [M+H]$^+$ 304, $R_t$=1.52 min.

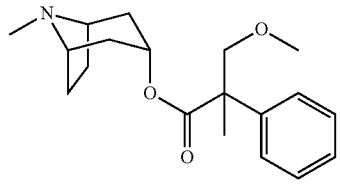 [SMILES: COCC(C)(C(=O)OC1CC2CCC(C1)N2C)c1ccccc1]

Figure 22A:
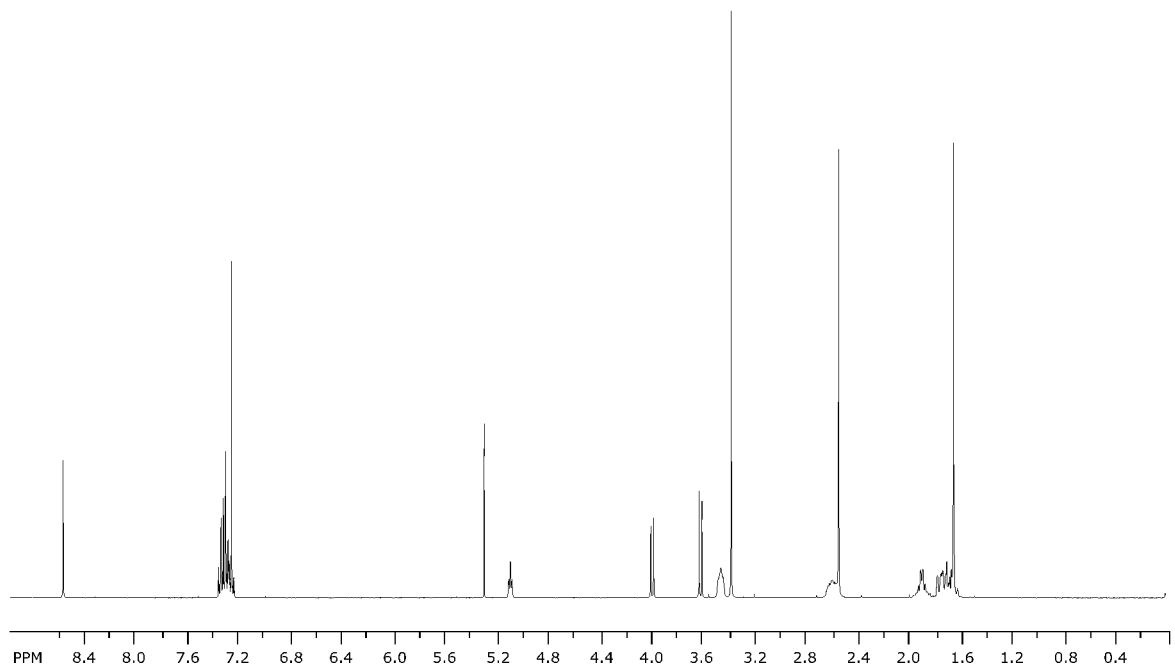
FIG. 22A is a ¹H NMR spectrum of (1R,3r,5S)-8-Methyl-8-azabicyclo[3.2.1]octan-3-yl 3-methoxy-2-methyl-2-phenylpropanoate.
Figure 22B:
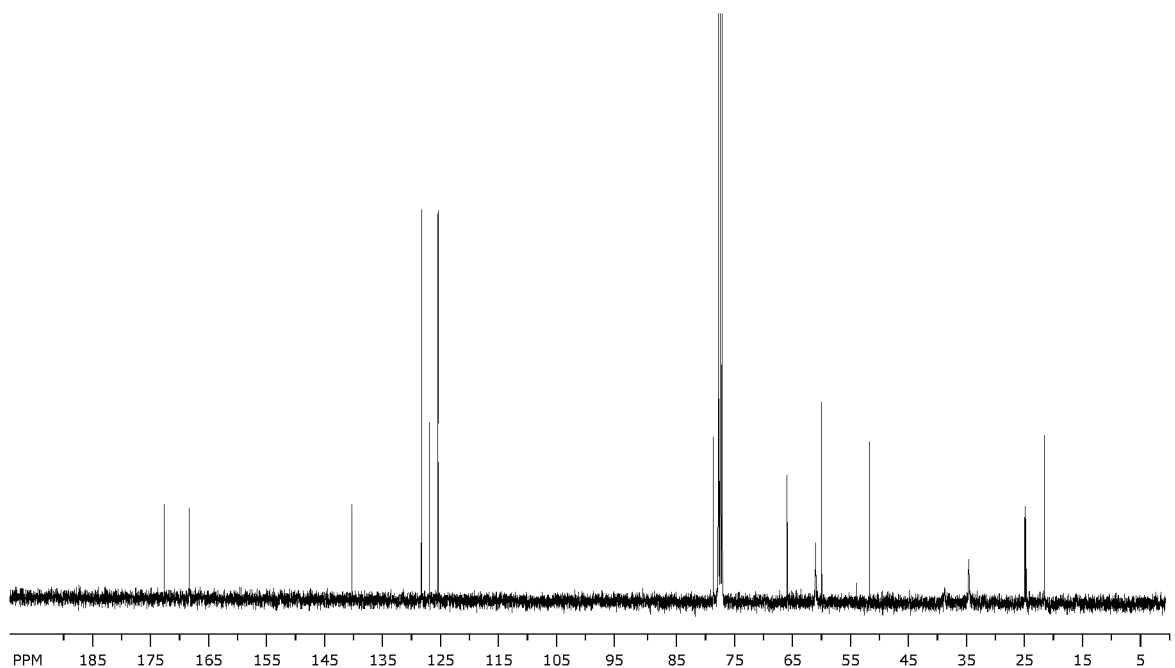
FIG. 22B is a ¹³C NMR spectrum of (1R,3r,5S)-8-Methyl-8-azabicyclo[3.2.1]octan-3-yl 3-methoxy-2-methyl-2-phenylpropanoate.

(1R,3r,5S)-8-Methyl-8-azabicyclo[3.2.1]octan-3-yl 3-methoxy-2-methyl-2-phenylpropanoate Crude (1R,3r,5S)-8-azabicyclo[3.2.1]octan-3-yl 3-methoxy-2-methyl-2-phenylpropanoate hydrochloride (1.18 g, 2.73 mmol) was dissolved in formic acid (4.0 mL) and treated with 37% formaldehyde soln. (0.81 mL, 10.9 mmol) and the reaction mixture was heated at reflux for 17 H. The reaction mixture was cooled to RT and charged to SCX-2 cartridge (50 g) pre-wetted with DCM. The cartridge was washed with DCM (400 mL), MeOH (200 mL) and product eluted with 2M $NH_3$ in MeOH (200 mL). The basic eluent was conc. in vacuo. And the residue purified by HPLC, Kinetix Axia C18 RP col. (long) using 5-50% $CH_3CN$ in $H_2O$ (0.1% HCOOH) @ 18 mL/min over 10 min Ramp, UV 194 nm. Relevant fractions were combined and freeze dried to give product as colourless syrup (415 mg, 48%), contains 0.75 eq Formate, 0.25 eq DCM. $^1$H NMR (400 MHz, $CDCl_3$) δ 7.37-7.24 (5H, m), 5.09 (1H, t, J=5.1 Hz), 3.99 (1H, d, J=8.7 Hz), 3.62 (1H, d, J=8.7 Hz), 3.49-3.42 (2H, m), 3.38 (3H, s), 2.65-2.50 (2H, m), 2.50 (3H, s), 1.93-1.84 (2H, m), 1.74-1.60 (4H, m), 1.64 (3H, s). LCMS (ESI) [M+H]$^+$ 318.3, $R_t$=3.05 min. The $^1$H NMR and $^{13}$C NMR spectra for the title compound are shown in FIGS. 22A and 22B respectively.

Synthetic Scheme of Example 12: (1R,3r,5S)-8-Methyl-8-azabicyclo[3.2.1]octan-3-yl 3-hydroxy-2-(4-methoxybenzyl)-2-phenylpropanoate

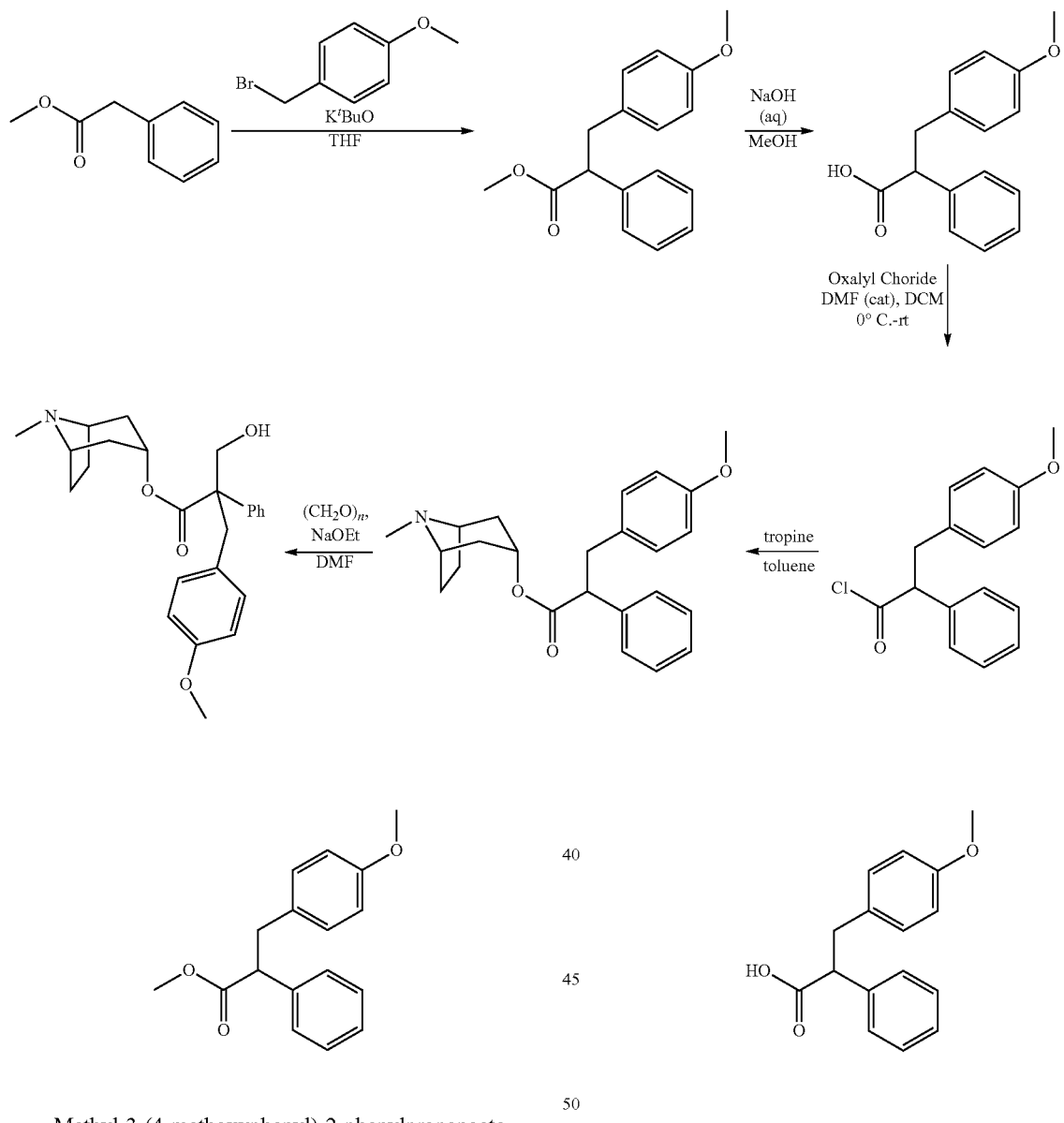

Methyl 3-(4-methoxyphenyl)-2-phenylpropanoate

Potassium tert butoxide (2.15 g, 19.16 mmol) was added to a stirred solution of methyl phenyl acetate (2.00 g, 13.32 mmol) in dry THF (20 mL) at 0° C. After stirring for 15 min, a solution of 4-methoxybenzyl bromide in dry THF (10 mL) was added dropwise maintaining T≤5° C. The resulting mixture was stirred for 10 min before allowed to warm to RT overnight. The resulting mixture was diluted EtOAc (150 mL) washed H$_2$O (50 mL) then brine (50 mL) and the layers separated. The organic layer was dried (Na$_2$SO$_4$) and conc. in vacuo. The residue was purified on silica (25 g 0-50% EtOAc in cyclo-hexane to give the title compound as pale yellow oil (1.0 g, 27%) impure but used without further purification. $^1$H NMR (400 MHz, CDCl$_3$) δ7.30 (4H, d, J=4.2 Hz), 7.26 (1H, m), 7.03 (2H, m), 6.77 (2H, m), 4.06 (1H, m), 3.76 (6H, s), 3.34 (1H, m), 2.96 (1H, m).

3-(4-Methoxyphenyl)-2-phenylpropanoic acid

Methyl 3-(4-methoxyphenyl)-2-phenylpropanoate (1.1 g, 4.07 mmol) in THF (20 mL) and MeOH (5 mL) at RT was treated with 2N NaOH (aq) (4 mL, 8.0 mmol) and stirred for 18 H. The reaction mixture was concentrated in vacuo and the residue diluted with H$_2$O (60 mL) and washed with EtOAc. The aqueous fraction was acidified with 1N HCl to pH 1.0 and extracted with EtOAc. The combined organic fractions were dried (MgSO$_4$) and concentrated in vacuo to give crude product as colourless oil that crystallised on standing. (881 mg 84%). LCMS R$_t$=1.28 min, 255.1 (M−H)$^−$. Used without purification. $^1$H NMR (400 MHz, CDCl$_3$) δ 7.32-7.26 (5H, d, m), 7.03 (2H, m), 6.77 (2H, m), 3.82 (1H, dd, J=6.9, 8.5 Hz), 3.76 (3H, s), 3.35 (1H, dd, J=6.96, 14.7 Hz).

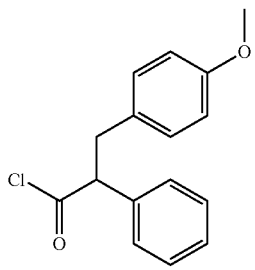

3-(4-Methoxyphenyl)-2-phenylpropanoyl chloride

A stirred solution of 3-(4-methoxyphenyl)-2-phenylpropanoic acid (450 mg, 1.76 mmol) in DCM (5.0 mL) containing DMF (10 μL) was treated dropwise at 0° C. with oxalyl chloride (200 μL, 2.29 mmol). The resulting mixture was stirred at 0° C. for 10 min and then allowed to warm to RT and stirred for 18 H. The reaction mixture was concentrated in vacuo, and the crude product was azeotroped with toluene (2×10 mL) to give the title crude compound (483 mg, 100%). Used immediately without purification.

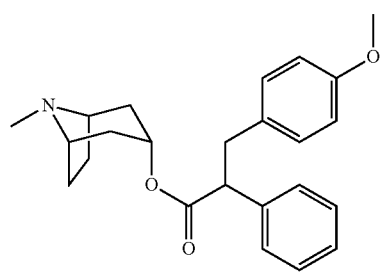

(1R,3r,5S)-8-Methyl-8-azabicyclo[3.2.1]octan-3-yl 3-(4-methoxyphenyl)-2-phenylpropanoate Crude 3-(4-methoxyphenyl)-2-phenylpropanoyl chloride (483 mg, 1.76 mmol) was stirred in dry toluene (5 mL) with tropine (248 mg, 1.76 mmol) at 100° C. for 3 H. The reaction mixture was concentrated in vacuo. The residue was treated with DCM (30 mL) and H₂O (20 mL) and basified to pH 10 with 1N NaOH (aq). The organic layer was separated, washed brine, dried (MgSO₄) and concentrated in vacuo. The resulting residue was purified on silica (12 g 0-10% MeOH in DCM) to the title compound as a light brown oil (277 mg, 41%). $^1$H NMR (400 MHz, CDCl$_3$) δ 7.31-7.26 (m, 5H), 7.07-7.04 (m, 2H), 6.80-6.75 (m, 2H), 4.91 (dd, J=5.2, 5.2 Hz, 1H), 3.77-3.76 (m, 3H), 3.37 (dd, J=9.0, 13.8 Hz, 1H), 3.06-2.94 (m, 3H), 2.25 (s, 3H), 2.16-2.10 (m, 2H), 1.84-1.72 (m, 2H), 1.60-1.48 (m, 4H), 1.42-1.35 (m, 1H). LCMS 0.99 min, 380.1 (M+H)$^+$.

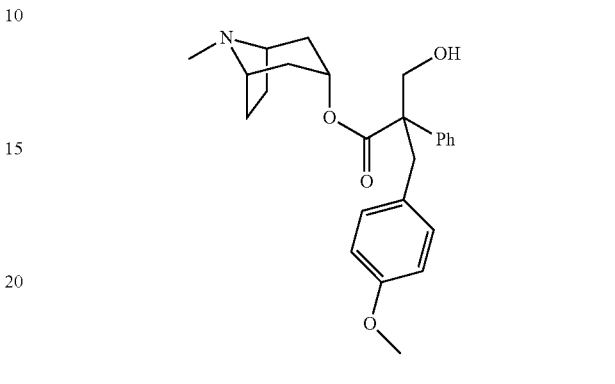

Figure 23A:
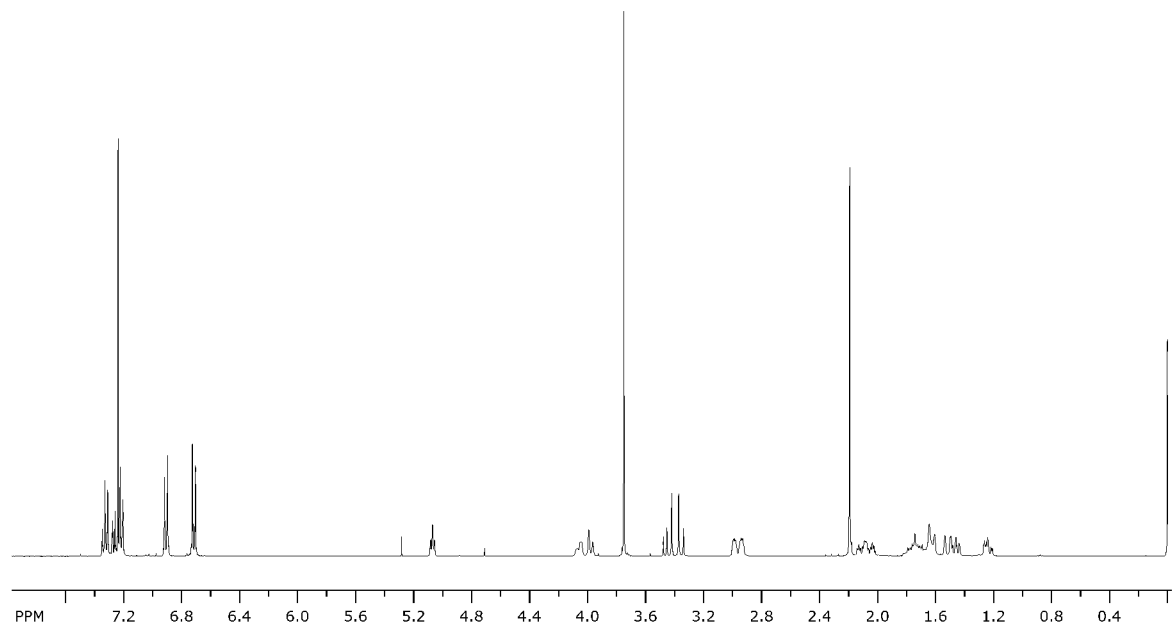
FIG. 23A is a ¹H NMR spectrum of (1R,3r,5S)-8-Methyl-8-azabicyclo[3.2.1]octan-3-yl 3-hydroxy-2-(4-methoxybenzyl)-2-phenylpropanoate.
Figure 23B:
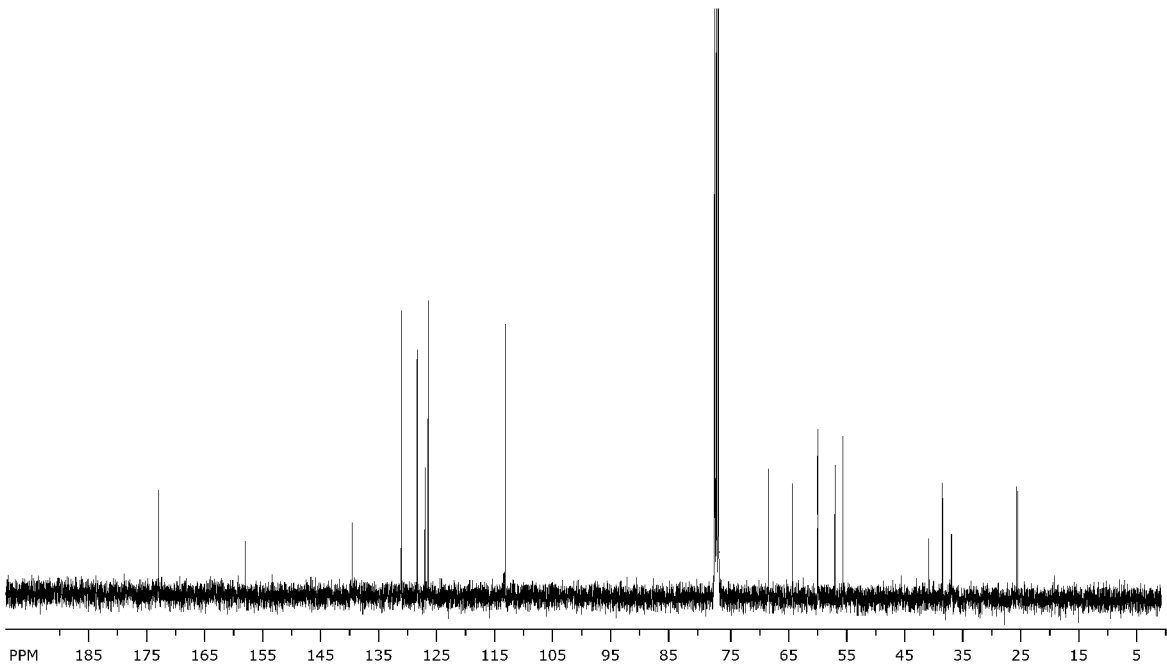
FIG. 23B is a ¹³C NMR spectrum of (1R,3r,5S)-8-Methyl-8-azabicyclo[3.2.1]octan-3-yl 3-hydroxy-2-(4-methoxybenzyl)-2-phenylpropanoate.

(1R,3r,5S)-8-Methyl-8-azabicyclo[3.2.1]octan-3-yl 3-hydroxy-2-(4-methoxybenzyl)-2-phenylpropanoate 1R,3r,5S)-8-Methyl-8-azabicyclo[3.2.1]octan-3-yl 3-(4-methoxyphenyl)-2-phenylpropanoate (200 mg, 0.53 mmol), in DMF (3 mL) was treated paraformaldehyde (160 mg, 5.33 mmol) followed by 21% sodium ethoxide solution, (4 μL, 0.05 mmol) and the reaction mixture stirred at 50° C. for 24 H. The reaction mixture was diluted with DCM (15 mL) and filtered through Celite. The filtrate was concentrated in vacuo to low volume and purified on silica (12 g, 0-10% MeOH in DCM) to give the title compound as a white solid (187 mg, 86%). $^1$H NMR (400 MHz, CDCl$_3$) 7.37-7.33 (2H, m), 7.26 (3H, s), 6.96-6.90 (2H, m), 6.76-6.71 (2H, m), 5.09 (1H, dd, J=5.3, 5.3 Hz), 4.08-3.96 (2H, m), 3.76-3.76 (3H, m), 3.49-3.34 (2H, m), 3.02-2.92 (2H, m), 2.20 (6H, s), 1.76-1.58 (3H, m), 1.56-1.44 (2H, m), 1.28-1.20 (1H, m). LCMS 3.30 min, 410.0 (M+H)$^+$. The $^1$H NMR and $^{13}$C NMR spectra for the title compound are shown in FIGS. 23A and 23B respectively.

Synthetic Scheme of Example 13: (1R,3r,5S)-8-Methyl-8-azabicyclo[3.2.1]octan-3-yl 3-hydroxy-2-(4-chlorobenzyl)-2-phenyl propanoate

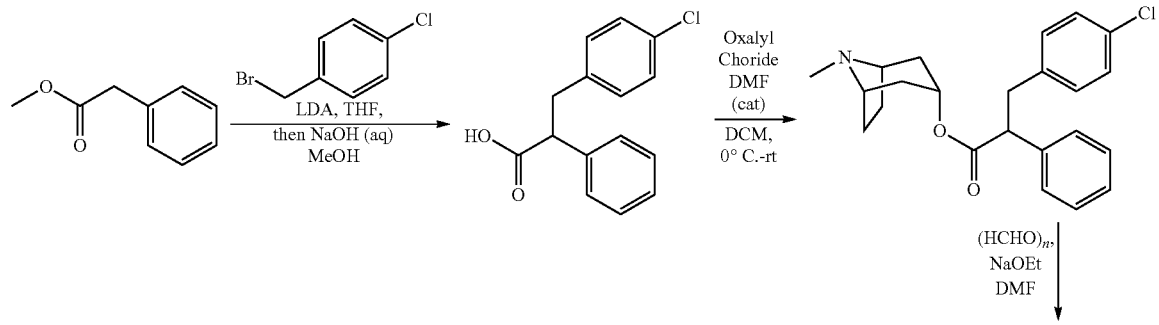

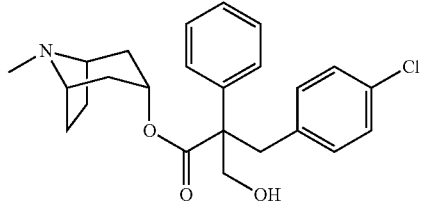

(1R,3r,5S)-8-Methyl-8-azabicyclo[3.2.1]octan-3-yl 3-(4-chlorophenyl)-2-phenylpropanoate A stirred solution of 3-(4-chlorophenyl)-2-phenylpropanoic acid (3.30 g, 12.7 mmol) in DCM (30 mL) containing DMF (45 µL) was treated dropwise at 0° C. with oxalyl chloride (2.2 mL, 25.3 mmol), and the resulting mixture stirred at 0° C. for 10 min then allowed to warm to RT and stirred for 18 H. The reaction mixture was concentrated in vacuo, and the crude product was azeotroped with toluene (20 mL) to give crude 3-(4-chlorophenyl)-2-phenylpropanoyl chloride, which was dissolved in dry toluene (50 mL). Tropine (1.62 g, 11.51 mmol) and triethylamine (4.8 mL, 34.52 mmol) were added, and the mixture stirred at 100° C. for 4 H, cooled to RT and stirred overnight. The reaction mixture was diluted with EtOAc and washed with saturated NaHCO₃, water, brine, dried (Na₂SO₄) and concentrated in vacuo. The residue was purified by chromatography on silica (80 g, 0-10% (2M NH₃ in MeOH) in DCM gradient) to give pure title compound as a viscous orange oil (2.24 g, 50%). A second crop of impure title compound (0.54 g, 12%) was also isolated as a brown oil. ¹H NMR (400 MHz, CDCl₃): δ 7.35-7.23 (5H, m), 7.22-7.16 (2H, m), 7.09-7.02 (2H, m), 4.90 (1H, t, J=5.4 Hz), 3.73 (1H, dd, J=6.9, 8.7 Hz), 3.39 (1H, dd, J=8.7, 13.8 Hz), 3.00 (1H, dd, J=6.9, 13.8 Hz), 2.99-2.94 (1H, m), 2.96-2.88 (1H, m), 2.18 (3H, s), 2.07-1.94 (2H, m), 1.86-1.64 (2H, m), 1.56-1.41 (3H, m), 1.34-1.25 (1H, m); LCMS (ESI) [M+H]⁺ 384.1.

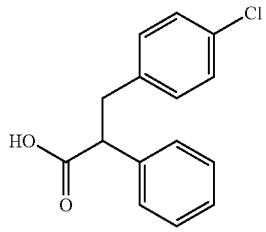 [SMILES: O=C(O)C(Cc1ccc(Cl)cc1)c1ccccc1]

3-(4-Chlorophenyl)-2-phenylpropanoic acid n-Butyllithium (2.5 M solution in hexanes, 15.3 mL, 38.3 mmol) was added dropwise, under a nitrogen atmosphere, to a chilled solution of N,N-diisopropylamine (5.6 mL, 40.0 mmol) in dry THF (20 mL) maintaining T≤0° C. The resulting LDA solution was stirred for 20 min then cooled with a dry-ice/acetone bath to −78° C. A solution of methyl phenylacetate (5.0 g, 33.3 mmol) in dry THF (20 mL) was added dropwise via syringe, maintaining T≤−55° C. After stirring for 2 H, a solution of 4-chlorobenzyl bromide (4.8 mL, 36.6 mmol) in dry THF (10 mL) was added, and the resulting mixture stirred overnight, warming to RT. The mixture was diluted with EtOAc (100 mL) and water (50 mL) and the aqueous layer was separated, and further extracted with EtOAc. The combined organic layers were washed with brine, dried (Na₂SO₄) and concentrated in vacuo, and the residue was dissolved in a mixture of methanol (20 mL) and THF (100 mL) and aqueous sodium hydroxide (2 M, 35 mL, 70 mmol) added. The resulting cloudy solution was stirred for 22 H, then concentrated in vacuo. The residue was partitioned between hydrochloric acid (1N, 50 mL) and EtOAc (100 mL). The aqueous layer was separated and further extracted with EtOAc. The combined organic layers were washed with brine, dried (Na₂SO₄) and concentrated in vacuo to give the title compound as an off-white solid (8.62 g, 99%). ¹H NMR (400 MHz, CDCl₃): 7.35-7.24 (5H, m), 7.21-7.15 (2H, m), 7.04-6.98 (2H, m), 3.80 (1H, dd, J=7.5, 8 Hz), 3.36 (1H, dd, J=8, 13.9 Hz), 3.0 (1H, dd, J=7, 13.9 Hz).

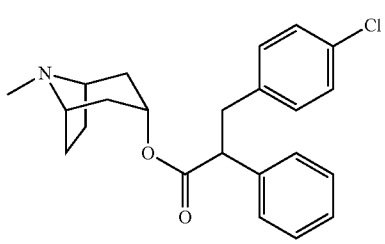 [SMILES: CN1C2CCC1CC(OC(=O)C(Cc1ccc(Cl)cc1)c1ccccc1)C2]

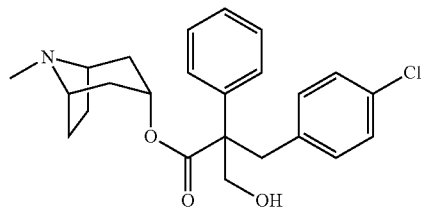 [SMILES: CN1C2CCC1CC(OC(=O)C(CO)(Cc1ccc(Cl)cc1)c1ccccc1)C2]

Figure 24A:
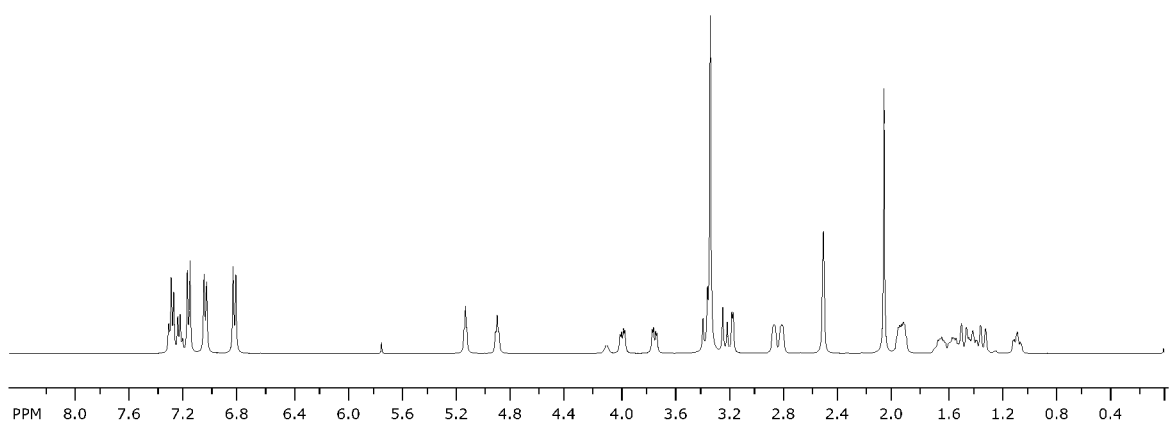
FIG. 24A is a ¹H NMR spectrum of (1R,3r,5S)-8-Methyl-8-azabicyclo[3.2.1]octan-3-yl 3-hydroxy-2-(4-chlorobenzyl)-2-phenyl propanoate.
Figure 24B:
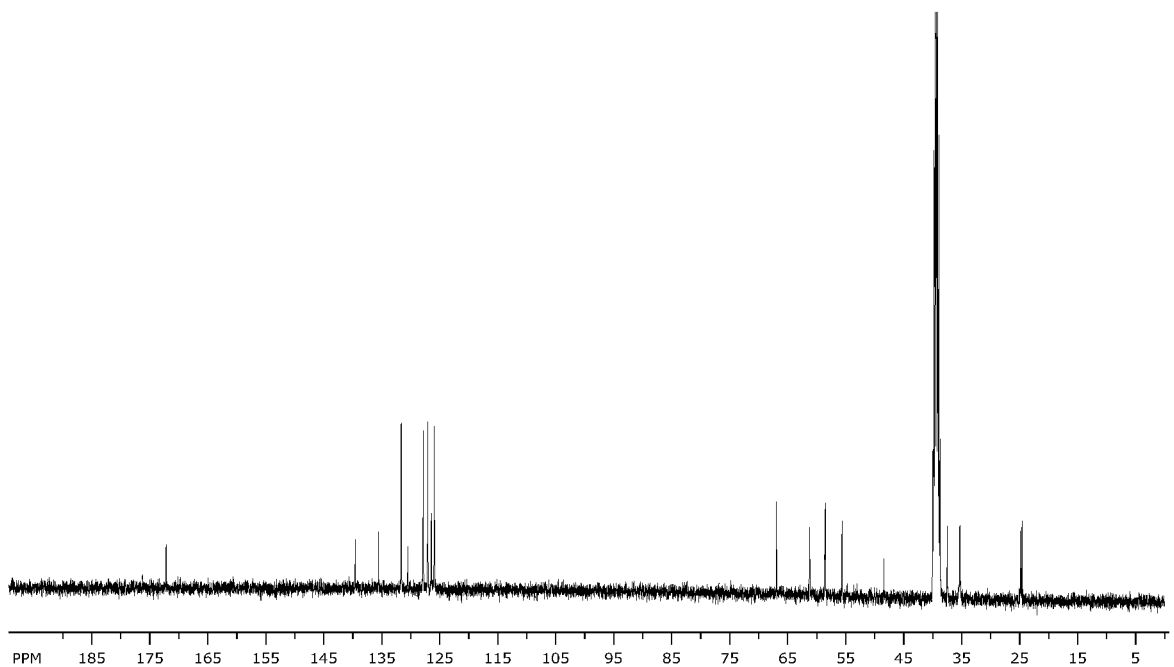
FIG. 24B is a ¹³C NMR spectrum of (1R,3r,5S)-8-Methyl-8-azabicyclo[3.2.1]octan-3-yl 3-hydroxy-2-(4-chlorobenzyl)-2-phenyl propanoate.

(1R,3r,5S)-8-Methyl-8-azabicyclo[3.2.1]octan-3-yl 3-hydroxy-2-(4-chlorobenzyl)-2-phenyl propanoate A solution of (1R,3r,5S)-8-methyl-8-azabicyclo[3.2.1]octan-3-yl 3-(4-chlorophenyl)-2-phenylpropanoate (2.22 g, 5.78 mmol) in DMF (10 mL) was treated with paraformaldehyde (0.26 g, 8.7 mmol). 21% Sodium ethoxide in ethanol solution (0.29 mL, 0.6 mmol) was added, and the resulting mixture stirred at RT for 14 H. The reaction mixture was diluted with water (50 mL) and EtOAc (100 mL) and the aqueous layer separated and further extracted with EtOAc. The combined organic layers were washed with 5% w/w aqueous lithium chloride solution (2×25 mL), brine, dried (Na₂SO₄), and filtered through a plug of celite. The solution was concentrated in vacuo and the residue purified on silica (40 g, 0.5-10% (2M NH$_3$ in MeOH) in DCM) to give the title compound as a white solid (0.86 g, 36%). $^1$H NMR (400 MHz, d$_6$-DMSO): δ 7.35-7.27 (2H, m), 7.27-7.21 (1H, m), 7.20-7.14 (2H, m), 7.09-7.01 (2H, m), 6.88-6.79 (2H, m), 5.14 (1H, broad t, J=4 Hz), 4.90 (1H, t, J=4.8 Hz), 3.98 (1H, dd, J=4.2, 10 Hz), 3.74 (1H, dd, J=3.8, 10 Hz), 3.36 (1H, d, J=13 Hz), 3.23 (1H, d, J=13 Hz), 2.90-2.84 (1H, m), 3.84-2.78 (1H, m), 2.06 (3H, s), 1.99-1.87 (2H, m), 1.72-1.27 (5H, m), 1.13-1.03 (1H, m); LCMS (ESI) [M+H]$^+$ 414.2. The $^1$H NMR and $^{13}$C NMR spectra for the title compound are shown in FIGS. 24A and 24B respectively.

Synthetic Scheme of Example 14: (1R,3r,5S)-8-Methyl-8-azabicyclo[3.2.1]octan-3-yl 3-hydroxy-2-(2-chlorobenzyl)-2-phenyl propanoate was separated and washed with brine, dried (Na$_2$SO$_4$) and concentrated in vacuo to give crude methyl 3-(2-chlorophenyl)-2-phenylpropanoate as an orange syrup. This was dissolved in a mixture of methanol (60 mL) and water (20 mL) and lithium hydroxide (0.80 g, 33.29 mmol) added. The resulting cloudy solution was stirred for 40 H, then concentrated in vacuo to give an orange aqueous solution, which was diluted with hydrochloric acid (1M, 20 mL), water (30 mL) and EtOAc (100 mL). The aqueous layer was separated and further extracted with EtOAc. The combined organic layers were washed with brine, dried (Na$_2$SO$_4$) and concentrated in vacuo to give the title compound as a mixture with unreacted methyl 3-(2-chlorophenyl)-2-phenylpropanoate. The mixture was re-dissolved in THF (50 mL), methanol (10 mL) and aqueous sodium hydroxide (2M, 17 mL, 34 mmol) and the resulting cloudy solution stirred at RT overnight. The

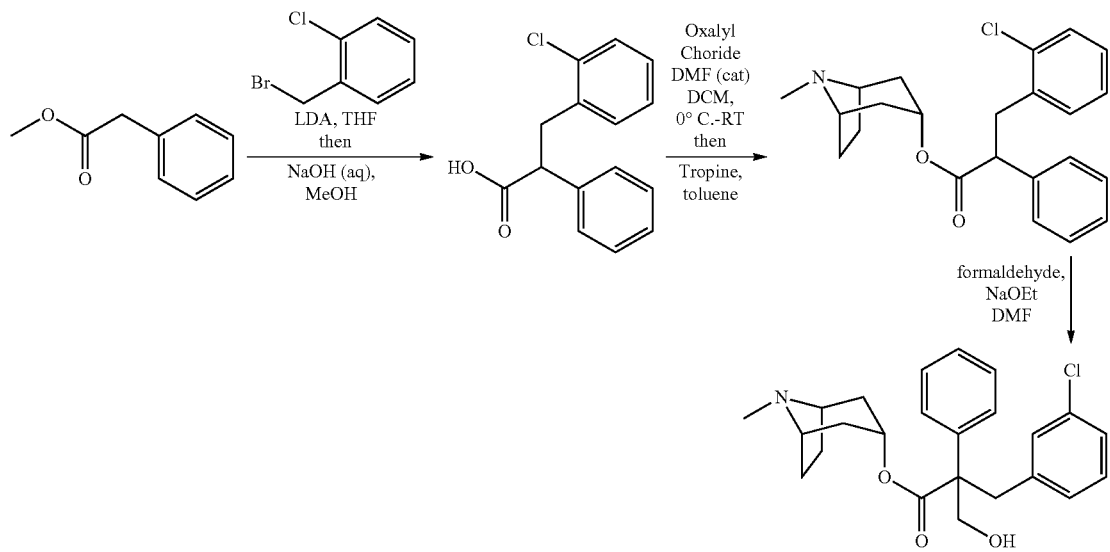

solvents were concentrated in vacuo and the residue partitioned between water (50 mL), hydrochloric acid (1M, 50 mL) and EtOAc (100 mL). The aqueous layer was separated and further extracted with EtOAc. The combined organic layers were washed with brine, dried (Na$_2$SO$_4$) and concentrated in vacuo to give the title compound as an off-white solid (4.10 g, 94%). $^1$H NMR (400 MHz, CDCl$_3$): δ 7.35-7.24 (6H, m), 7.16-7.08 (1H, m), 7.07-7.03 (2H, m), 4.00 (1H, dd, J=6.7, 8.5 Hz), 3.49 (1H, dd, J=8.5, 13.8 Hz), 3.15 (1H, dd, J=6.7, 13.8 Hz).

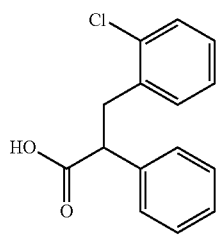

3-(2-Chlorophenyl)-2-phenylpropanoic acid n-Butyllithium (2.5 M solution in hexanes, 15.3 mL, 38.3 mmol) was added dropwise, under a nitrogen atmosphere, to a chilled solution of N,N-diisopropylamine (5.6 mL, 39.95 mmol) in dry THF (20 mL) maintaining T≤0° C. The resulting LDA solution was stirred for 20 min then cooled with a dry-ice/acetone bath to −74° C. A solution of methyl phenylacetate (5.0 g, 33.3 mmol) in dry THF (20 mL) was added dropwise via syringe, maintaining T≤−55° C. After stirring for 1 H, a solution of 2-chlorobenzyl bromide (4.8 mL, 36.6 mmol) in dry THF (10 mL) was added, and the resulting mixture stirred overnight, warming to RT. The mixture was diluted with EtOAc (50 mL) and saturated aqueous ammonium chloride (10 mL). The organic layer

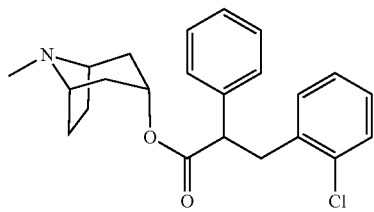 [SMILES: CN1C2CCC1CC(OC(=O)C(Cc1ccccc1Cl)c1ccccc1)C2]

1R,3r,5S)-8-Methyl-8-azabicyclo[3.2.1]octan-3-yl 3-(2-chlorophenyl)-2-phenylpropanoate A stirred solution of 3-(2-chlorophenyl)-2-phenylpropanoic acid (3.30 g, 12.7 mmol) in DCM (30 mL) containing DMF (45 µL) was treated with oxalyl chloride (2.2 mL, 25.3 mmol), and the resulting mixture stirred at RT overnight. The reaction mixture was concentrated in vacuo, and the crude product was azeotroped with toluene (20 mL). The residue was dissolved in dry toluene (50 mL) and tropine (1.62 g, 11.5 mmol) and triethylamine (4.8 mL, 34.5 mmol) were added, and the mixture stirred at 110° C. for 4 H, cooled to RT and stirred overnight. The reaction mixture was diluted with EtOAc (150 mL) and washed with saturated NaHCO₃, water, brine, dried (Na₂SO₄) and concentrated in vacuo. The residue was purified on silica (120 g, 0-10% (2M NH₃ in MeOH) in DCM) to give pure title compound as a viscous orange oil (3.26 g, 73%). ¹H NMR (400 MHz, CDCl₃) δ 7.37-7.22 (6H, m), 7.16-7.04 (3H, m), 4.91 (1H, t, J=5.4 Hz), 3.95 (1H, dd, J=6.5, 9 Hz), 3.51 (1H, dd, J=9, 13.5 Hz), 3.16 (1H, dd, J=6.5, 13.5 Hz), 2.97-2.88 (2H, m), 2.18 (3H, s), 2.05-1.94 (2H, m), 1.86-1.63 (2H, m), 1.55-1.40 (3H, m), 1.35-1.26 (1H, m); LCMS (ESI) [M+H]⁺ 384.1.

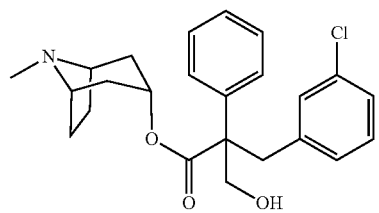 [SMILES: CN1C2CCC1CC(OC(=O)C(CO)(Cc1cccc(Cl)c1)c1ccccc1)C2]

Figure 25A:
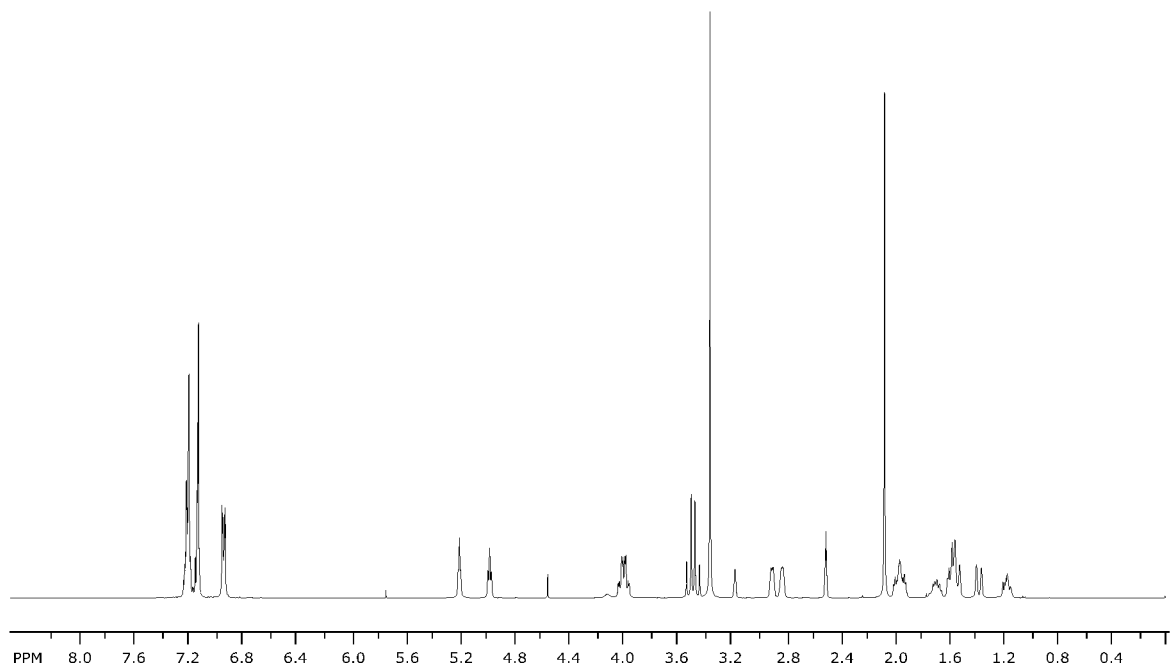
FIG. 25A is a ¹H NMR spectrum of (1R,3r,5S)-8-Methyl-8-azabicyclo[3.2.1]octan-3-yl 3-hydroxy-2-(2-chlorobenzyl)-2-phenyl propanoate.
Figure 25B:
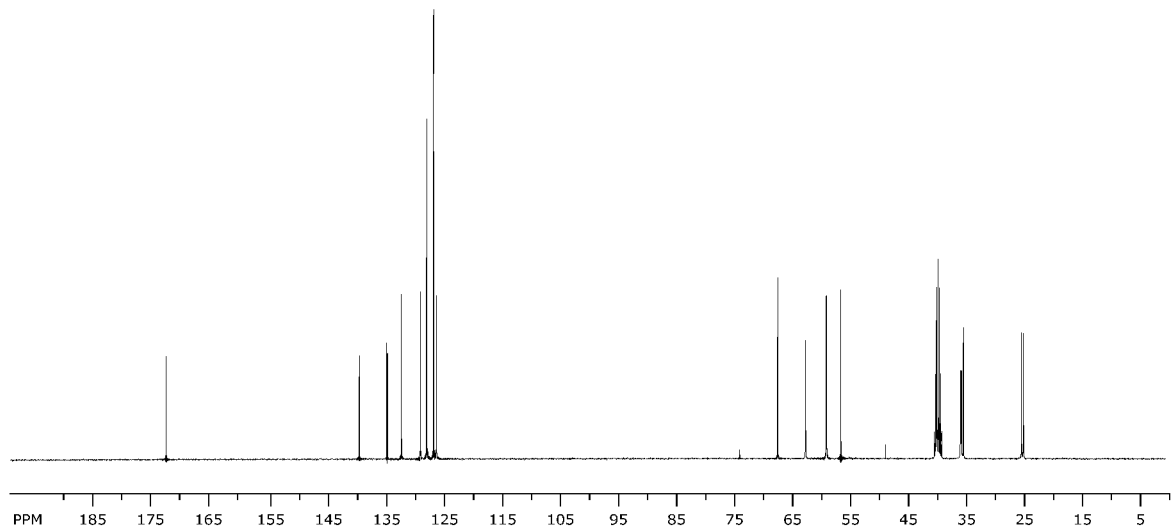
FIG. 25B is a ¹³C NMR spectrum of (1R,3r,5S)-8-Methyl-8-azabicyclo[3.2.1]octan-3-yl 3-hydroxy-2-(2-chlorobenzyl)-2-phenyl propanoate.

(1R,3r,5S)-8-Methyl-8-azabicyclo[3.2.1]octan-3-yl 3-hydroxy-2-(2-chlorobenzyl)-2-phenyl propanoate A solution of (1R,3r,5S)-8-methyl-8-azabicyclo[3.2.1]octan-3-yl 3-(2-chlorophenyl)-2-phenylpropanoate (1.92 g, 5.0 mmol) in DMF (10 mL) was treated with paraformaldehyde (0.23 g, 7.5 mmol). 21% Sodium ethoxide in ethanol solution (0.25 mL, 0.5 mmol) was added, and the resulting mixture stirred at RT for 3 H then heated to 45° C. overnight. Second portions of paraformaldehyde (0.23 g, 7.5 mmol) and 21% sodium ethoxide in ethanol (0.25 mL, 0.5 mmol) were added and the mixture stirred at 45° C. for 4.5 H, then at 80° C. for 1.5 H. Heating was stopped and the reaction mixture stirred at RT overnight. The mixture was diluted with water (50 mL) and EtOAc (100 mL), the aqueous layer separated and further extracted with EtOAc. The combined organic layers were washed with 5% w/w aqueous lithium chloride solution (2×25 mL), brine, dried (Na₂SO₄), filtered through celite, and concentrated in vacuo. The residue was purified on silica [40 g, 0.5-10% (2M NH₃ in MeOH) in DCM] to give the title compound as a white solid (1.0 g, 48%). ¹H NMR (400 MHz, d₆-DMSO): δ 7.26-7.18 (4H, m), 7.17-7.10 (3H, m), 6.99-6.91 (2H, m), 5.21 (1H, broad t, J=4 Hz), 4.99 (1H, t, J=5.2 Hz), 4.06-3.94 (2H, m), 3.51 (1H, d, J=14 Hz), 3.46 (1H, d, J=14 Hz), 2.93-2.87 (1H, m), 2.86-2.79 (1H, m), 2.07 (3H, s), 2.03-1.89 (2H, m), 1.76-1.62 (1H, m), 1.62-1.49 (3H, m), 1.42-1.33 (1H, m), 1.22-1.10 (1H, m); LCMS (ESI) [M+H]⁺ 414.2. The ¹H NMR and ¹³C NMR spectra for the title compound are shown in FIGS. 25A and 25B respectively.

Synthetic Scheme of Example 15: (1R,3r,5S)-8-Methyl-8-azabicyclo[3.2.1]octan-3-yl 3-hydroxy-2-(4-hydroxybenzyl)-2-phenyl propanoate formic acid salt

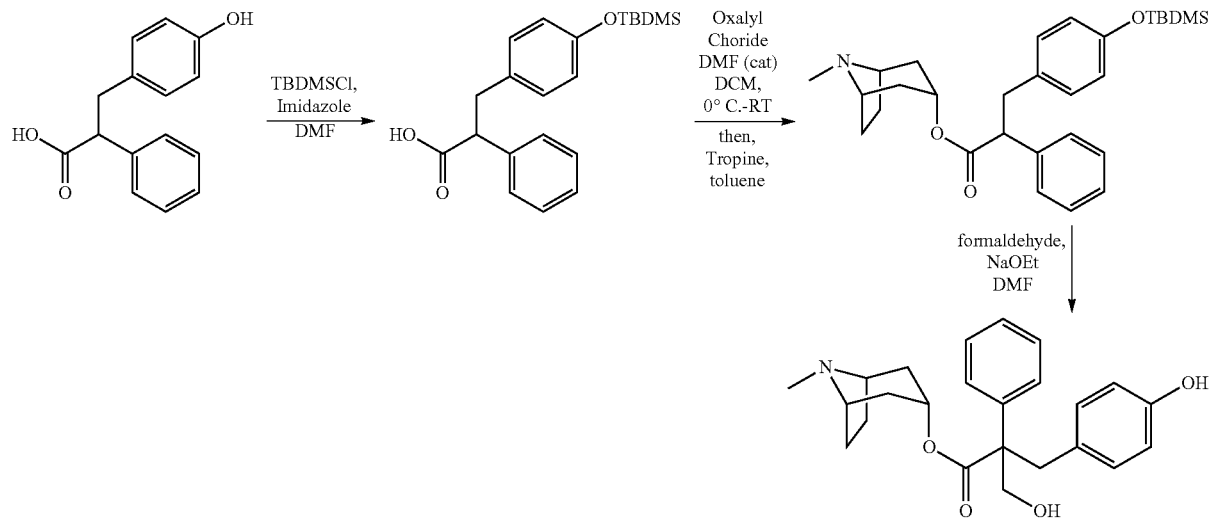

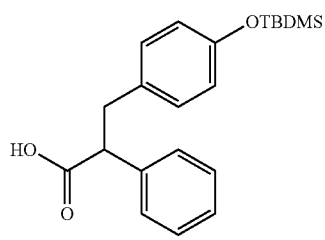 [SMILES: CC(C)(C)[Si](C)(C)Oc1ccc(CC(C(=O)O)c2ccccc2)cc1]

3-(4-((tert-Butyldimethylsilyl)oxy)phenyl)-2-phenyl-propanoic acid tert-Butyldimethylchlorosilane (3.16 g, 21.0 mmol) was added to a stirred solution of 3-(4-hydroxyphenyl)-2-phenylpropanoic acid (2.42 g, 10.0 mmol), and imidazole (2.04 g, 29.97 mmol) in dry DMF (40 mL), and the resulting mixture stirred at RT overnight. A further portion of tert-butyldimethylchlorosilane (0.75 g, 5.0 mmol) was added and stirring continued for 2 H. The reaction mixture was diluted with EtOAc and washed with water, saturated aqueous lithium chloride, brine, dried ($Na_2SO_4$) and concentrated in vacuo to give a straw coloured oil. The oil was dissolved in methanol (40 mL), potassium carbonate (1.52 g, 11.0 mmol) added, and the resulting suspension stirred at RT for 1.5 H. The reaction mixture was concentrated in vacuo and the residue partitioned between water and DCM, and the aqueous phase acidified to pH 3 by the careful addition of 1M hydrochloric acid. The aqueous layer was separated and further extracted with DCM. The combined organic layer was washed with brine, dried ($Na_2SO_4$) and concentrated in vacuo to give the crude title compound as a straw coloured oil. This was purified by chromatography on silica (80 g, 0-20% EtOAc in DCM gradient) to give the title compound as a straw coloured oil (1.58 g, 44%). $^1$H NMR (400 MHz, $CDCl_3$): δ 7.32-7.22 (5H, m), 6.95-6.89 (2H, m), 6.71-6.64 (2H, m), 3.79 (1H, apparent t, J=8 Hz), 3.32 (1H, dd, J=8.2, 13.9 Hz), 2.95 (1H, dd, J=7.2, 13.9 Hz), 0.95 (9H, s), 0.15 (6H, s).

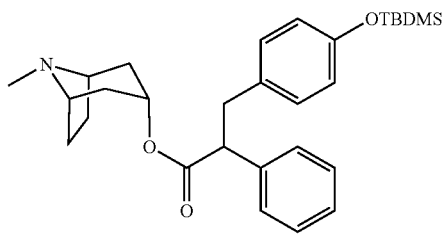 [SMILES: CN1C2CCC1CC(OC(=O)C(Cc1ccc(O[Si](C)(C)C(C)(C)C)cc1)c1ccccc1)C2]

(1R,3r,5S)-8-Methyl-8-azabicyclo[3.2.1]octan-3-yl 3-(4-((tert-butyldimethylsilyl)oxy)phenyl)-2-phenyl-propanoate A stirred solution of 3-(4-((tert-butyldimethylsilyl)oxy) phenyl)-2-phenylpropanoic acid (1.30 g, 3.65 mmol) in DCM (20 mL) containing one drop of DMF (45 μL), was treated dropwise at 0° C. with oxalyl chloride (0.64 mL, 7.3 mmol), and the resulting mixture stirred at 0° C. for 10 min then the cooling bath was removed and the reaction mixture stirred overnight, warming to RT. The mixture was concentrated in vacuo, and the crude acid chloride intermediate azeotroped with toluene (20 mL) to give 3-(4-((tert-butyldimethylsilyl)oxy)phenyl)-2-phenylpropanoyl chloride as a straw coloured oil. This was dissolved in dry toluene (20 mL) and tropine (0.51 g, 3.7 mmol) and triethylamine (1.5 mL, 11.0 mmol) added. The resulting mixture was stirred at 110° C. for 3 H. The mixture was cooled to RT, diluted with EtOAc (50 mL) and washed with water, saturated $NaHCO_3$, brine, dried ($Na_2SO_4$) and concentrated in vacuo. The product was purified on silica (25 g, 0-10% (2M $NH_3$ in MeOH) in DCM) to give pure title compound as a colourless syrup (0.778 g, 44%). $^1$H NMR (400 MHz, $CDCl_3$): δ 7.34-7.21 (5H, m), 7.02-6.94 (2H, m), 6.73-6.66 (2H, m), 4.90 (1H, t, J=5.3 Hz), 3.73 (1H, dd, J=6.6, 9 Hz), 3.35 (1H, dd, J=9, 13.8 Hz), 2.95 (1H, dd, J=6.6, 13.8 Hz), 2.98-2.89 (2H, m), 2.19 (3H, s), 2.05-1.94 (2H, m), 1.87-1.68 (2H, m), 1.60-1.51 (2H, m), 1.50-1.35 (3H, m), 0.96 (9H, s), 0.16 (6H, s).

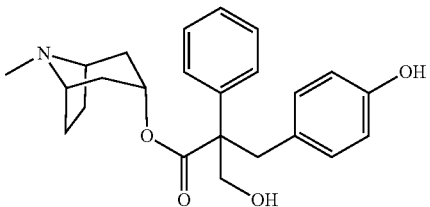 [SMILES: CN1C2CCC1CC(OC(=O)C(CO)(Cc1ccc(O)cc1)c1ccccc1)C2]

Figure 26A:
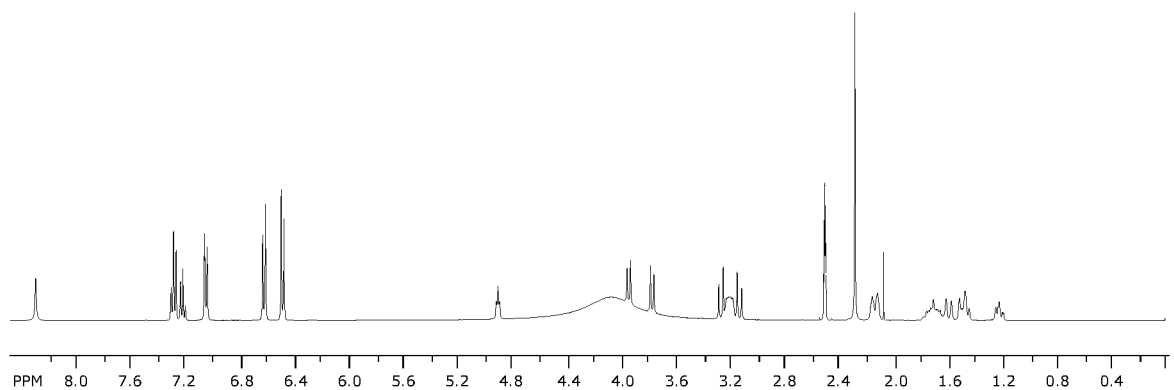
FIG. 26A is a ¹H NMR spectrum of (1R,3r,5S)-8-Methyl-8-azabicyclo[3.2.1]octan-3-yl 3-hydroxy-2-(4-hydroxybenzyl)-2-phenyl propanoate formic acid salt.
Figure 26B:
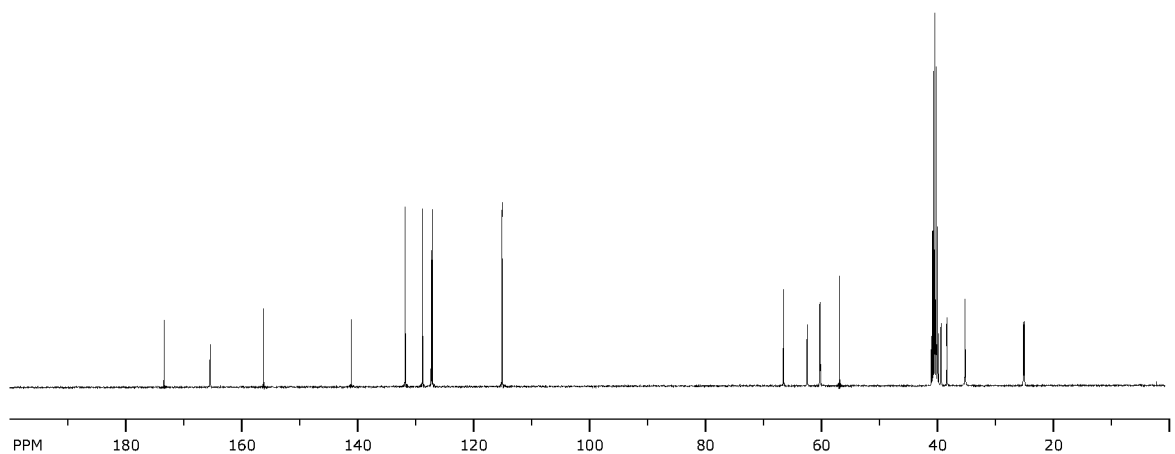
FIG. 26B is a ¹³C NMR spectrum of (1R,3r,5S)-8-Methyl-8-azabicyclo[3.2.1]octan-3-yl 3-hydroxy-2-(4-hydroxybenzyl)-2-phenyl propanoate formic acid salt.
Figure 27A:
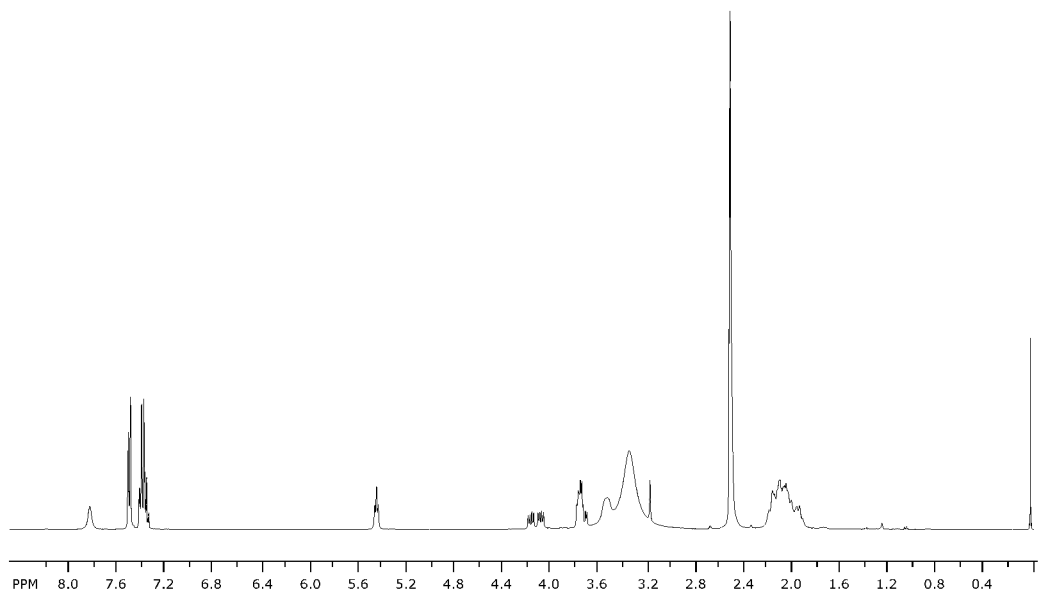
FIG. 27A is a ¹H NMR spectrum of 2-Fluoro-3-hydroxy-N-((1R,3r,5S)-8-methyl-8-azabicyclo[3.2.1]octan-3-yl)-2-phenylpropanamide.
Figure 27B:
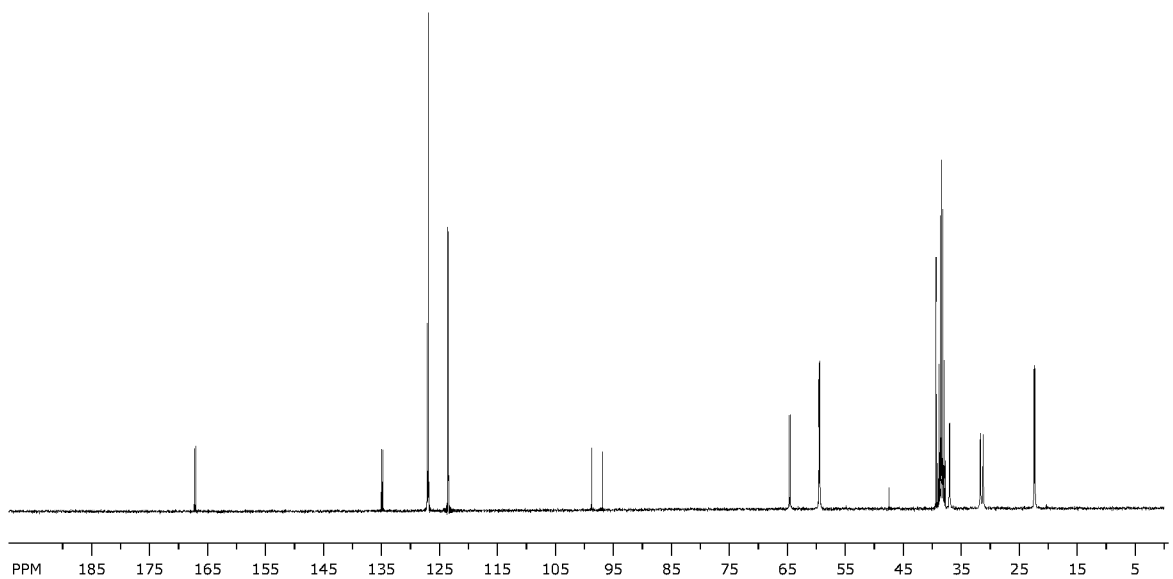
FIG. 27B is a ¹³C NMR spectrum of 2-Fluoro-3-hydroxy-N-((1R,3r,5S)-8-methyl-8-azabicyclo[3.2.1]octan-3-yl)-2-phenylpropanamide.

(1R,3r,5S)-8-Methyl-8-azabicyclo[3.2.1]octan-3-yl 3-hydroxy-2-(4-hydroxybenzyl)-2-phenyl propanoate formic acid salt A solution of (1R,3r,5S)-8-methyl-8-azabicyclo[3.2.1]octan-3-yl 3-(4-((tert-butyldimethylsilyl)oxy)-phenyl)-2-phenylpropanoate (0.77 g, 1.61 mmol) in DMF (10 mL) was treated with paraformaldehyde (0.072 g, 2.4 mmol), and 21% sodium ethoxide in ethanol solution (0.06 mL, 0.16 mmol) added at RT. The resulting mixture was stirred at RT for 6.5 H then second portions of paraformaldehyde (0.072 g, 2.4 mmol) and 21% sodium ethoxide in ethanol solution (0.06 mL, 0.15 mmol) were added and the mixture stirred overnight. A third portion of paraformaldehyde (0.072 g, 2.4 mmol) and 21% sodium ethoxide in ethanol solution (0.06 mL, 0.15 mmol) was added and stirring continued at RT for 3 days. The reaction mixture was diluted with EtOAc (100 mL) and washed with water, 5% aqueous lithium chloride, brine, dried ($Na_2SO_4$) and concentrated in vacuo. The product was partially purified on 15 μm silica (4 g, 0-20% (2M $NH_3$ in MeOH) in DCM) to give impure title compound as a white solid, which was further purified by reverse-phase preparative HPLC using a Kinetix Axia® C18 21.2×250 mm column, 18 mL/min 10-60/a MeCN in water with 0.1% HCOOH gradient eluent, with 220 nm UV monochromatic detection. To give the title compound as a white solid (0.273 g, 38%). $^1$H NMR (400 MHz, $d_6$-DMSO): δ 8.31 (1H, s), 7.34-7.26 (2H, m), 7.26-7.19 (1H, m), 7.10-7.02 (2H, m), 6.63 (2H, dm, J=8.5 Hz), 6.49 (2H, dm, J=8.5 Hz), 4.91 (1H, t, J=4.9 Hz), 4.48-3.60 (3H, bs), 3.95 (1H, d, J=10 Hz), 3.77 (1H, d, J=10 Hz), 3.26 (1H, d, J=13.3 Hz), 3.25-3.16 (2H, m), 3.13 (1H, d, J=13.3 Hz), 2.28 (3H, s), 2.19-2.09 (2H, m), 1.80-1.41 (5H, m), 1.26-1.17 (1H, m); LCMS (ESI) $[MH]^+$ 396.4. The $^1$H NMR and $^{13}$C NMR spectra for the title compound are shown in FIGS. 26A and 26B respectively.

Synthetic Scheme of Example 16: 2-Fluoro-3-hydroxy-N-((1R,3r,5S)-8-methyl-8-azabicyclo[3.2.1]octan-3-yl)-2-phenylpropanamide

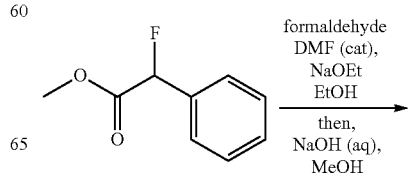

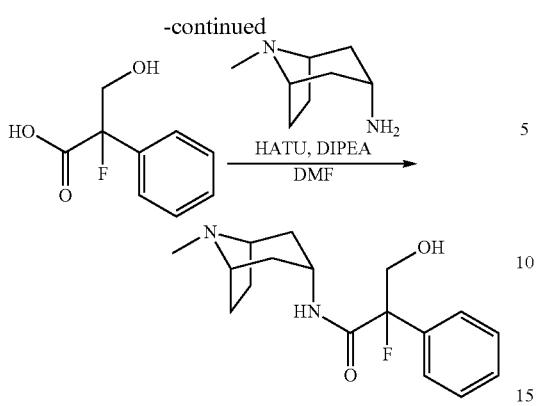

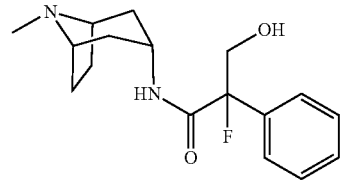

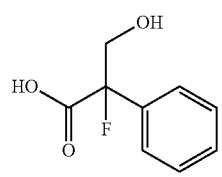 [SMILES: O=C(O)C(F)(CO)c1ccccc1]

2-Fluoro-3-hydroxy-2-phenylpropanoic acid

A stirred mixture of methyl 2-fluoro-2-phenylpropanoate (1.49 g, 7.62 mmol) and paraformaldehyde (0.55 g, 18.3 mmol) in DMF (5 mL) was treated with 21% sodium ethoxide in ethanol solution (0.43 mL, 1.14 mmol), and the resulting orange coloured suspension stirred at RT for 3.5 H. The mixture was diluted with EtOAc and washed with hydrochloric acid, 5% aqueous lithium chloride, brine, dried ($Na_2SO_4$), and concentrated in vacuo to give crude methyl 2-fluoro-3-hydroxy-2-phenylpropanoate as an orange oil (1.82 g). This was dissolved in a mixture of water (9 mL) and methanol (20 mL) then lithium hydroxide (0.44 g, 18.3 mmol) added and the resulting mixture stirred at RT for 4 H. A solution of hydrogen chloride in 1,4-dioxane (4N, 5 mL, 20 mmol) was added and the mixture concentrated in vacuo to give the crude title compound as a dark cream coloured solid (2.21 g, quantitative). This material was used without purification. $^1$H NMR (400 MHz, $d_6$-DMSO): δ 7.58-7.29 (5H, m), 4.11 (1H, dd, J=12.3, 30.7 Hz), 3.79 (1H, dd, J=12.3, 17.6 Hz), 3.10-3.09 (2H+water, broad s).

2-Fluoro-3-hydroxy-N-((1R,3r,5S)-8-methyl-8-azabicyclo[3.2.1]octan-3-yl)-2-phenylpropanamide HATU (3.77 g, 9.9 mmol) was added, in three portions, to a stirred ice-cold solution of crude 2-fluoro-3-hydroxy-2-phenylpropanoic acid (2.21 g, 7.6 mmol), 8-methyl-8-azabicyclo[3.2.1]octan-3-amine (1.18 g, 8.4 mmol), and DIPEA (4.0 mL, 22.9 mmol) in DMF (20 mL). The resulting orange mixture was warmed to RT and stirred for 40 H. The reaction mixture was concentrated in vacuo, and the residue partitioned between water and EtOAc. The aqueous layer was separated and further extracted with EtOAc. The combined organic layers were washed with 5% aqueous lithium chloride solution, brine, dried ($Na_2SO_4$) and concentrated in vacuo to give an orange gum. The product was purified on silica (40 g, 15 μm pore-size silica, 5-20% (2M $NH_3$ in MeOH) in DCM) to give the title compound as a pale yellow solid (0.631 g, 27%). $^1$H NMR (400 MHz, $d_6$-DMSO): δ 7.84 (1H, bs), 7.63-7.47 (2H, m), 7.44-7.33 (3H, m), 5.45 (1H, t, J=5.8 Hz), 4.12 (1H, ddd, J=6.3, 12.3, 33 Hz), 3.80-3.67 (2H, m), 3.61-3.47 (2H, m), 2.49 (3H, bs), 2.25-1.86 (8H, m); LCMS (ESI) $[M+H]^+$ 307.2. The $^1$H NMR and $^{13}$C NMR spectra for the title compound are shown in FIGS. 37A and 37B respectively.

Synthetic Scheme of Example 17: (1R,3r,5S)-8-Methyl-8-azabicyclo[3.2.1]octan-3-yl 2-(4-fluorobenzyl)-3-hydroxy-2-phenyl propanoate

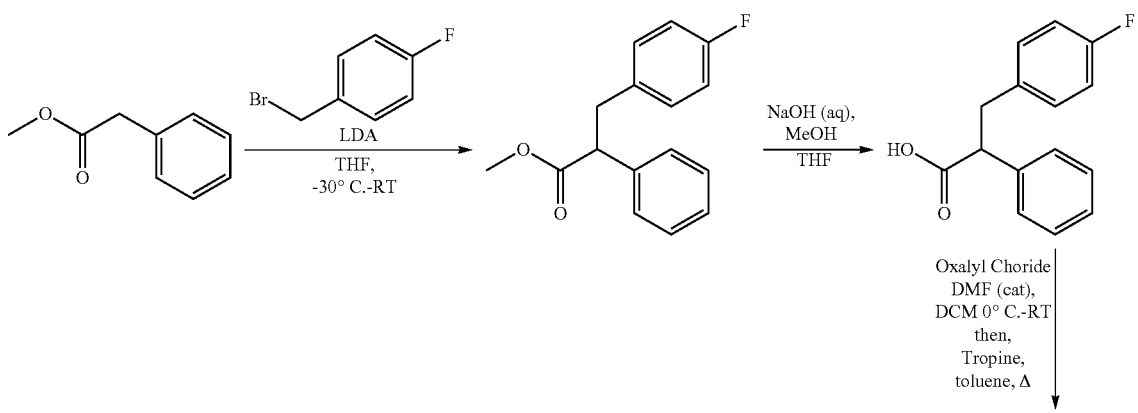

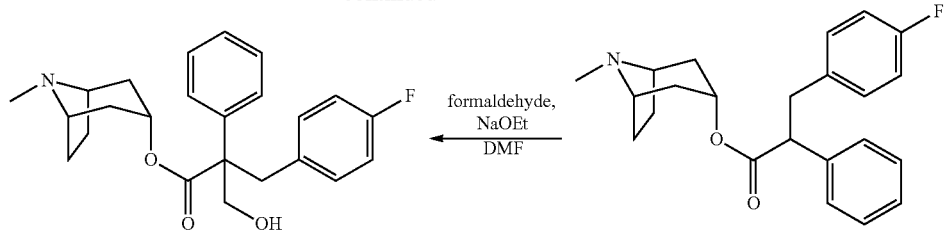

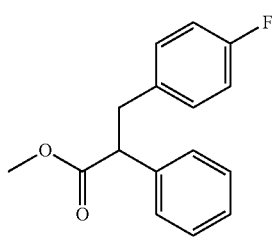 [SMILES: COC(=O)C(Cc1ccc(F)cc1)c1ccccc1]

Methyl 3-(4-fluorophenyl)-2-phenylpropanoate

Lithium diisopropylamine 2M in THF/Heptane/Ethylbenzene (10 mL, 20 mmol) was added to a stirred solution of methyl phenyl acetate (3.00 g, 20.0 mmol) in dry THF (40 mL) under Argon, at −30° C. After stirring for 15 min the reaction mixture was allowed to warm to 0° C. and stirred for 30 min. The reaction mixture was cooled to −30° C. and a solution of 4-fluorobenzyl bromide (4.10 g, 21.7 mmol) in dry THF (10 mL) was added dropwise maintaining T≤−25° C. The resulting mixture was stirred for 10 min before being allowed to warm to RT over 16 H. The solvent was removed in vacuo and the residue diluted with EtOAc washed with water and brine, and the layers separated. The organic fraction was dried ($Na_2SO_4$) and concentrated in vacuo. The residue was purified on silica (40 g, 0-10% MTBE in cyclohexane) to give the title compound as pale yellow oil (1.51 g, 29/6) impure but used without further purification. $^1$H NMR (400 MHz, $CDCl_3$): δ 7.33-7.26 (5H, m), 7.08-7.03 (2H, m), 6.93-6.88 (2H, m), 3.81-3.77 (1H, m), 3.37 (1H, dd, J=8.7, 13.8 Hz), 2.99 (1H, ddd, J=4.1, 6.7, 13.5 Hz).

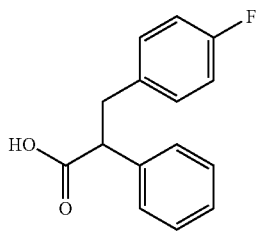 [SMILES: O=C(O)C(Cc1ccc(F)cc1)c1ccccc1]

3-(4-Fluorophenyl)-2-phenylpropanoic acid

Methyl 3-(4-fluorophenyl)-2-phenylpropanoate (1.51 g, 5.9 mmol) was stirred in THF (30 mL) and MeOH (3 mL) and treated with 2M NaOH (aq) (12 mL, 24.0 mmol). The reaction mixture was stirred at RT for 18 H. The solvent was removed in vacuo, the residue diluted with $H_2O$ and washed with EtOAc. The aqueous fraction was acidified with 1M HCl to pH 1.0 and extracted with EtOAc. The combined organic extracts were dried ($MgSO_4$) and concentrated in vacuo to give the title compound as light brown oil that crystallised on standing (1.13 g, 79%). Material used without purification. $^1$H NMR (400 MHz, $CDCl_3$): δ 7.34-7.27 (5H, m), 7.06 (2H, ddd, J=3.1, 5.3, 11.8 Hz), 6.93-6.88 (2H, m), 3.81 (1H, dd, J=7.1, 8.4 Hz), 3.37 (1H, dd, J=8.4, 13.9 Hz), 3.01 (1H, dd, J=7.1, 13.9 Hz); LCMS (ESI) [M−H]$^+$ 243.

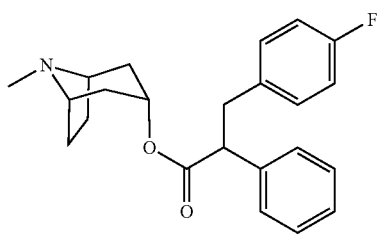 [SMILES: CN1C2CCC1CC(OC(=O)C(Cc1ccc(F)cc1)c1ccccc1)C2]

(1R,3r,5S)-8-Methyl-8-azabicyclo[3.2.1]octan-3-yl 3-(4-fluorophenyl)-2-phenylpropanoate A stirred solution 3-(4-fluorophenyl)-2-phenylpropanoic acid (1.13 g, 4.6 mmol) in DCM (10 mL) containing DMF (200 μL) under argon was treated dropwise at 0° C. with oxalyl chloride (573 μL, 6.6 mmol). The resulting mixture was stirred at 0° C. for 10 min then allowed to warm to RT and stirred for 18 H. The solvents were removed in vacuo, and the residue azeotroped with toluene (2×15 mL) to give crude acid chloride, which was stirred in dry toluene (10 mL) with (1R,3r,5S)-8-methyl-8-azabicyclo[3.2.1]octan-3-ol (790 mg, 5.6 mmol) under argon at 100° C. for 4 H. The reaction mixture was concentrated in vacuo and the residue treated with DCM (60 mL) and $H_2O$ (40 mL) and basified to pH 10 with 1M NaOH (aq). The organic fraction was separated, washed brine, dried ($MgSO_4$) and concentrated in vacuo to give crude the product as pale yellow oil (1.27 g). This was used crude without purification. $^1$H NMR (400 MHz, $CDCl_3$): δ 7.26 (4H, s), 7.19-7.07 (3H, m), 6.94-6.89 (2H, m), 4.99-4.89 (1H, m), 3.73 (1H, dd, J=6.8, 8.8 Hz), 3.40 (1H, dd, J=8.8, 13.8 Hz), 3.03-2.88 (3H, m), 2.36-2.32 (2H, m), 2.25-2.20 (3H, m), 2.09-1.43 (5H, m), 1.36-1.25 (1H, m); LCMS (ESI) [M+H]$^+$ 368.1.

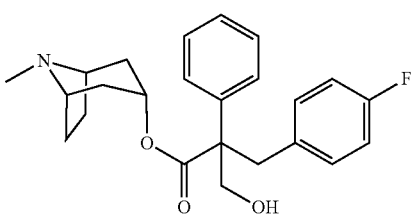 [SMILES: CN1C2CCC1CC(OC(=O)C(CO)(Cc1ccc(F)cc1)c1ccccc1)C2]

Figure 28A:
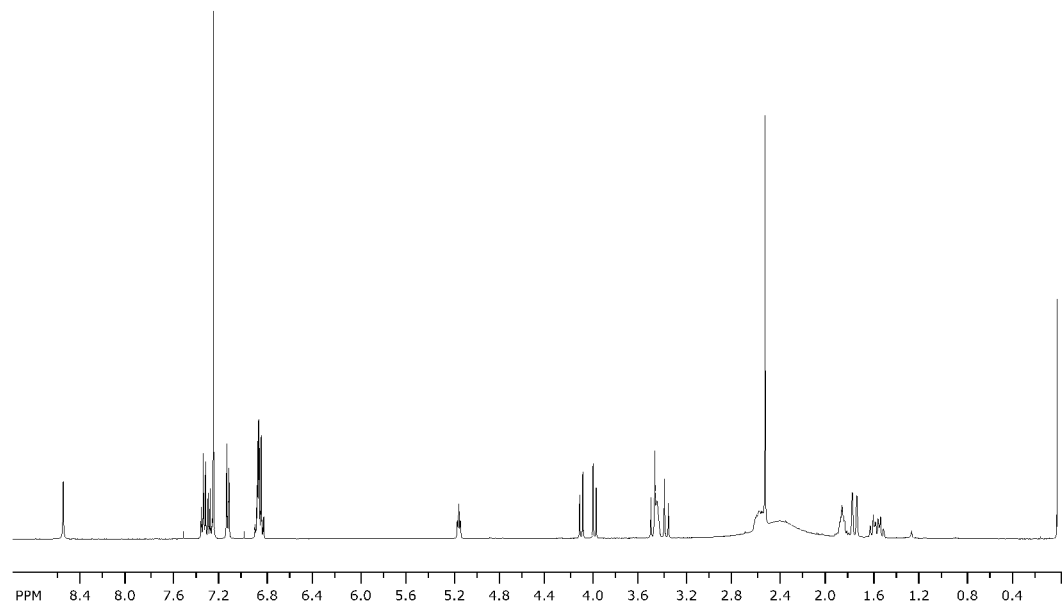
FIG. 28A is a ¹H NMR spectrum of (1R,3r,5S)-8-Methyl-8-azabicyclo[3.2.1]octan-3-yl 2-(4-fluorobenzyl)-3-hydroxy-2-phenyl propanoate.
Figure 28B:
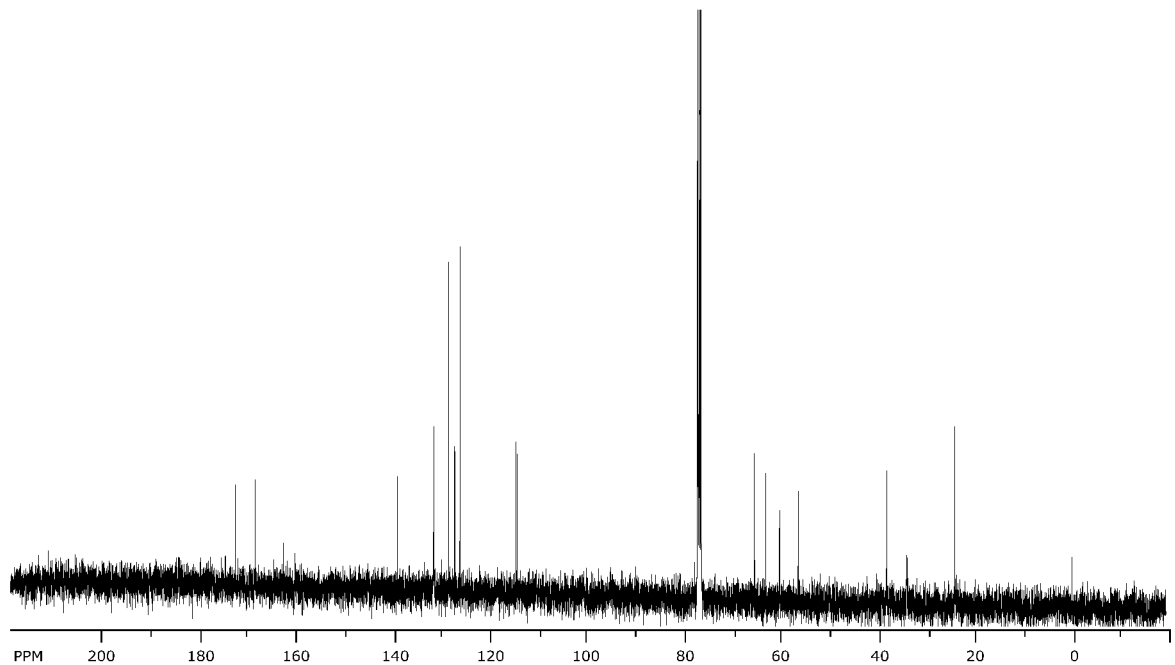
FIG. 28B is a ¹³C NMR spectrum of (1R,3r,5S)-8-Methyl-8-azabicyclo[3.2.1]octan-3-yl 2-(4-fluorobenzyl)-3-hydroxy-2-phenyl propanoate.

(1R,3r,5S)-8-Methyl-8-azabicyclo[3.2.1]octan-3-yl 2-(4-fluorobenzyl)-3-hydroxy-2-phenyl propanoate (1R,3r,5S)-8-Methyl-8-azabicyclo[3.2.1]octan-3-yl 3-(4-fluorophenyl)-2-phenylpropanoate (154 mg, 0.4 mmol), in DMF (3 mL) was treated paraformaldehyde (160 mg, 5.3 mmol) followed by 21% sodium ethoxide solution, (4 µL, 0.05 mmol) and stirred at 50±5° C. for 24 H. The reaction mixture was cooled, diluted with DCM (15 mL) and filtered through Celite. The filtrate was concentrated in vacuo to low volume and purified on silica (4 g, 0-10% 2M NH$_3$/MeOH in DCM) to give the title compound as a white solid 108 mg. This was further purified by HPLC, Kinetix Axia C18 RP column (Long) using 10-60% CH$_3$CN in H$_2$O [0.1% HCOOH] over 10 min ramp @ 18 mL/min (UV @ 200 nm) to give the title compound as white solid (64 mg, 38%). $^1$H NMR (400 MHz, CDCl$_3$): δ 7.38-7.27 (3H, m), 7.16-7.12 (2H, m), 6.90-6.85 (4H, m), 5.15 (1H, t, J=5.1 Hz), 4.12-4.08 (1H, m), 3.98 (1H, d, J=10.6 Hz,), 3.50-3.34 (4H, m), 2.61-2.53 (3H, m), 2.52 (4H, s), 1.91-1.80 (2H, m), 1.75 (2H, d, J=16.4 Hz), 1.62-1.48 (2H, m), LCMS (ESI) [M+H]$^+$ 398.3. The $^1$H NMR and $^{13}$C NMR spectra for the title compound are shown in FIGS. 28A and 28B respectively.

Synthetic Scheme of Example 18: (1R,3r,5S)-8-Methyl-8-azabicyclo[3.2.1]octan-3-yl 3-hydroxy-2-(4-methylbenzyl)-2-phenyl propanoate

Methyl 2-phenyl-3-(p-tolyl)propanoate

Potassium tert-butoxide (4.08 g, 22.1 mmol) was added to a stirred solution of methyl phenyl acetate (3.00 g, 20 mmol) in dry THF (30 mL) under argon, at 0° C. After stirring for 15 min, a solution of 4-methylbenzyl bromide in dry THF (10 mL) was added dropwise, maintaining T≤5° C. The resulting mixture was stirred for 10 min before being allowed to warm to RT over 16 H. The resulting mixture was diluted EtOAc washed with water then brine. The organic fraction was dried (Na$_2$SO$_4$) and concentrated in vacuo to give the crude product as yellow oil. This was purified on silica (40 g 0-25% EtOAc in cyclohexane) to give the title compound as a pale yellow oil (3.60 g 70%) impure but used without further purification.

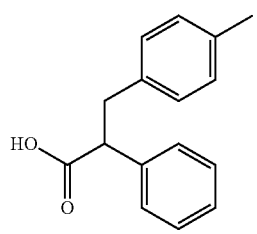

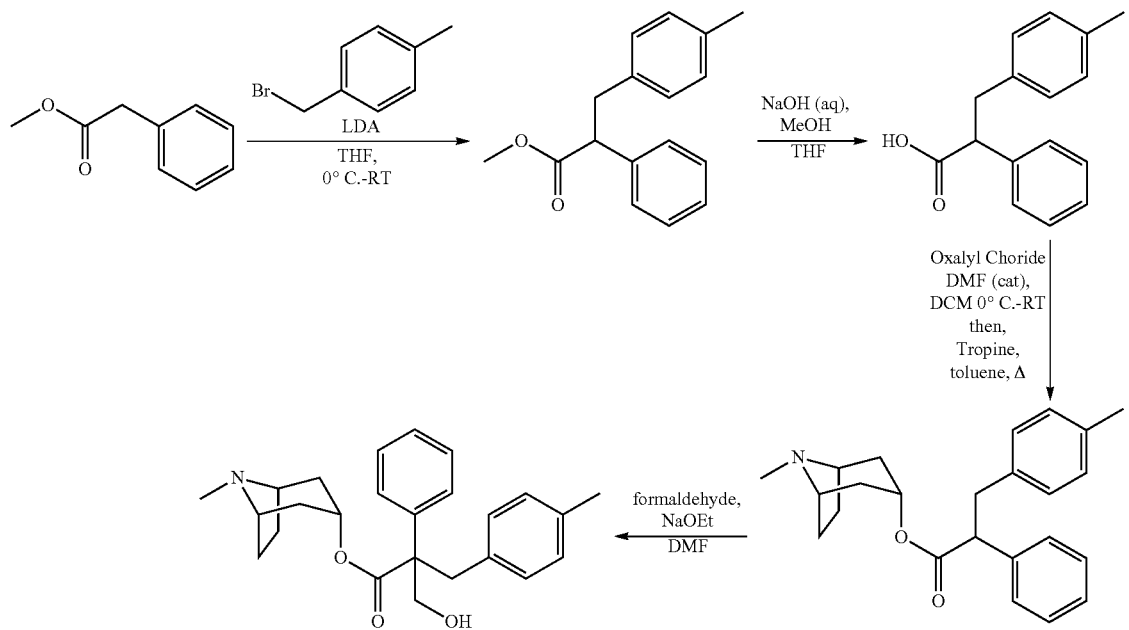

2-Phenyl-3-(p-tolyl)propanoic acid

Methyl 2-phenyl-3-(p-tolyl)propanoate (3.60 g, 14.2 mmol) in THF (60 mL) and MeOH (6 mL) was treated with 2M NaOH (aq) (20 mL, 40 mmol) and the reaction mixture stirred at RT for 18 H. The reaction mixture was concentrated in vacuo and the residue diluted with water (100 mL) and washed with EtOAc. The aqueous fraction was acidified with 1M HCl to pH 1.0 and extracted with EtOAc. The combined organic fractions were dried (MgSO$_4$) and concentrated in vacuo to give the crude title compound as light brown oil which crystallised on standing (1.67 g, 49%).

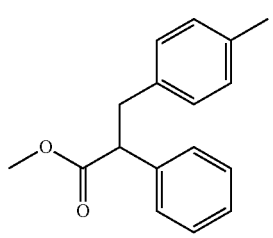

Used without purification. ¹H NMR (400 MHz, CDCl₃): δ 7.31 (3H, d, J=4.3 Hz), 7.29-7.27 (2H, m), 7.02 (4H, dd, J=8.2, 12.7 Hz), 3.84 (1H, dd, J=6.8, 8.6 Hz), 3.37 (1H, dd, J=8.6, 13.9 Hz), 3.00 (1H, dd, J=6.8, 13.9 Hz), 2.29 (3H, s). (3H, m), 2.89, (3H, s), 2.17 (3H, s), 2.07-1.91 (4H, m), 1.63-1.44 (3H, m); LCMS (ESI) [M+H]⁺ 364.2.

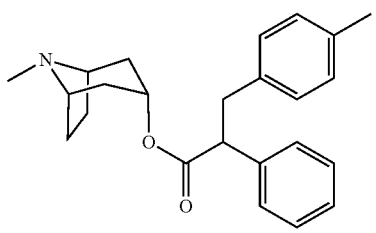

(1R,3r,5S)-8-Methyl-8-azabicyclo[3.2.1]octan-3-yl 2-phenyl-3-(p-tolyl)propanoate A stirred solution of 2-phenyl-3-(p-tolyl)propanoic acid (1.0 g, 4.2 mmol) in DCM (10 mL) containing DMF (200 μL) under argon was treated dropwise at 0° C. with oxalyl chloride (518 μL, 5.9 mmol). The reaction mixture was stirred at 0° C. for 10 min then allowed to warm to RT and stirred for 18 H. The reaction mixture was concentrated in vacuo, and the residue azeotroped with toluene (2×15 mL) to give the crude acid chloride. This was stirred in dry toluene (10 mL) with (1R,3r,5S)-8-methyl-8-azabicyclo[3.2.1]octan-3-ol (710 mg, 5.1 mmol) under argon at 100° C. for 4 H. The reaction mixture was concentrated in vacuo. The resultant residue was treated with DCM (60 mL) and water (40 mL) and basified to pH 10 with 1M NaOH (aq). The organic fraction was separated, washed with brine, dried (MgSO₄) concentrated in vacuo. The residue was purified on silica (12 g, 0-10% 2M NH₃/MeOH in DCM) to give the title compound as a light brown oil (688 mg 45%). ¹H NMR (400 MHz, CDCl₃): δ 7.33-7.25 (5H, m), 7.03 (4H, m), 4.88 (1H, m), 3.78-3.72 (1H, m), 3.38 (1H, m), 3.18 (1H, m) 3.02-2.88

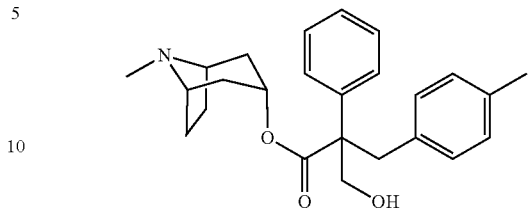

Figure 29A:
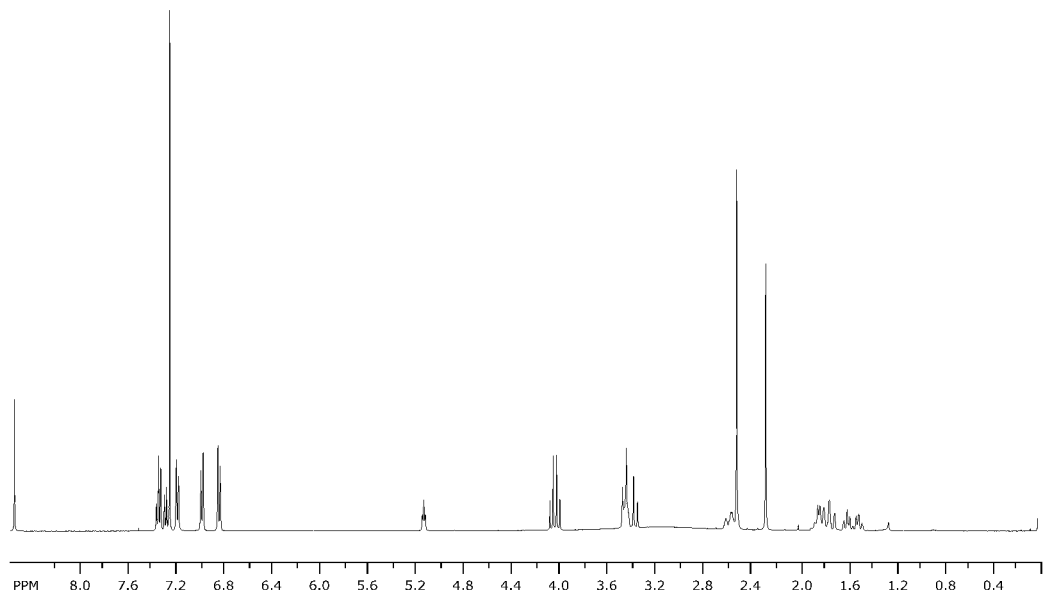
FIG. 29A is a ¹H NMR spectrum of (1R,3r,5S)-8-Methyl-8-azabicyclo[3.2.1]octan-3-yl 3-hydroxy-2-(4-methylbenzyl)-2-phenyl propanoate.
Figure 29B:
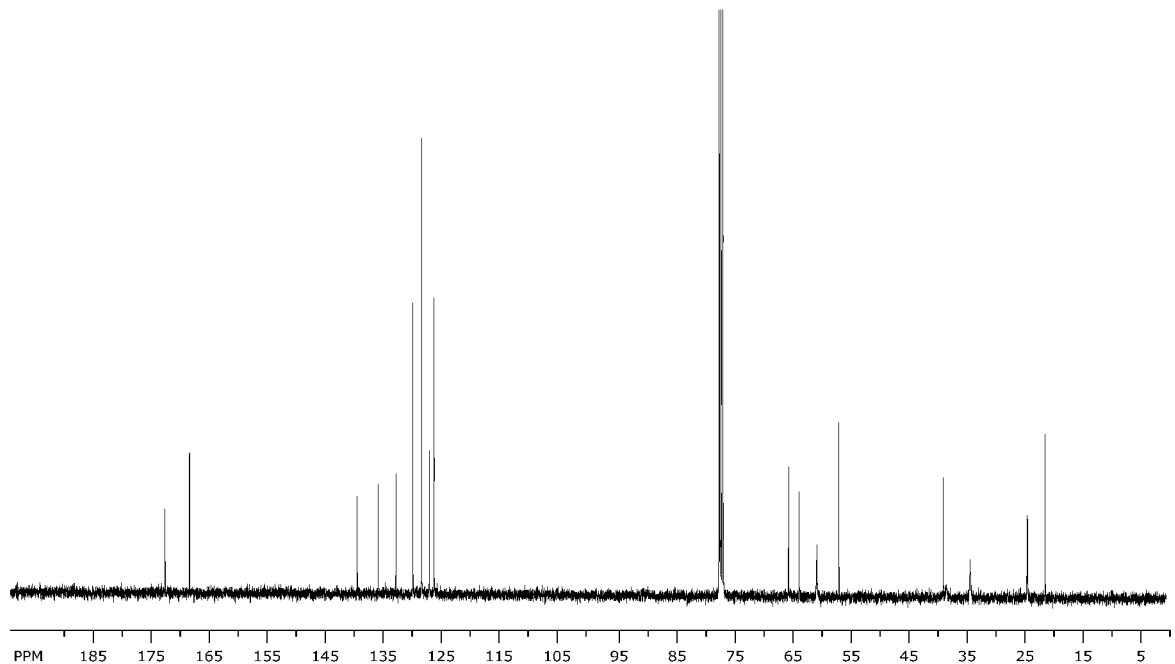
FIG. 29B is a ¹³C NMR spectrum of (1R,3r,5S)-8-Methyl-8-azabicyclo[3.2.1]octan-3-yl 3-hydroxy-2-(4-methylbenzyl)-2-phenyl propanoate.

(1R,3r,5S)-8-Methyl-8-azabicyclo[3.2.1]octan-3-yl 3-hydroxy-2-(4-methylbenzyl)-2-phenyl propanoate (1R,3r,5S)-8-Methyl-8-azabicyclo[3.2.1]octan-3-yl 2-phenyl-3-(p-tolyl)propanoate (688 mg, 1.9 mmol), in DMF (10 mL) was treated paraformaldehyde (722 mg, 24.0 mmol) followed by 21% sodium ethoxide solution (20 μL, 0.054 mmol) and stirred at 50±5° C. for 24 H. The reaction mixture was diluted with DCM (50 mL) and filtered through Celite. The filtrate was concentrated in vacuo and the residue purified on silica (12 g 0-10% 2M NH₃/MeOH in DCM) the resultant residue was further purified by HPLC, Kinetix Axia C18 RP col. (Long) using 10-60% CH₃CN in H₂O [0.1% HCOOH] over 10 min ramp @ 18 mL/min, (UV=200 nm) to give the title compound as a white solid (260 mg, 35%). ¹H NMR (400 MHz, CDCl₃): δ 7.38-7.33 (2H, m), 7.31-7.27 (1H, m), 7.20 (2H, d, J=7.3 Hz,), 7.01-6.97 (2H, m), 6.87-6.83 (2H, m), 5.14 (1H, t, J=5.0 Hz), 4.04 (2H, q, J=11.0 Hz), 3.49-3.34 (5H, m), 2.62-2.55 (2H, m), 2.52 (3H, s), 2.29-2.27 (3H, m), 1.87-1.69 (4H, m), 1.63-1.46 (2H, m); LCMS (ESI) [M+H]⁺ 394.3. The ¹H NMR and ¹³C NMR spectra for the title compound are shown in FIGS. 29A and 29B respectively.

Synthetic Scheme of Example 19: (1R,3r,5S)-8-methyl-8-azabicyclo[3.2.1]octan-3-yl 2-(3-chlorobenzyl)-3-hydroxy-2-phenyl propanoate

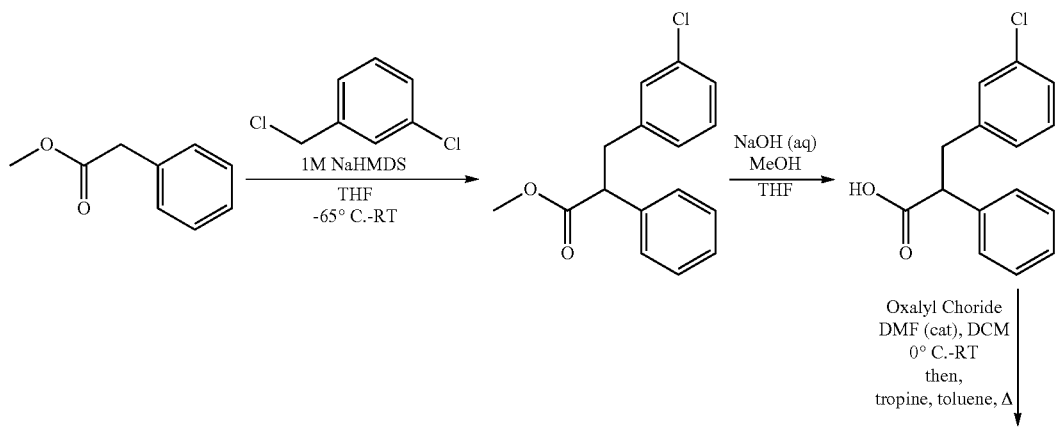

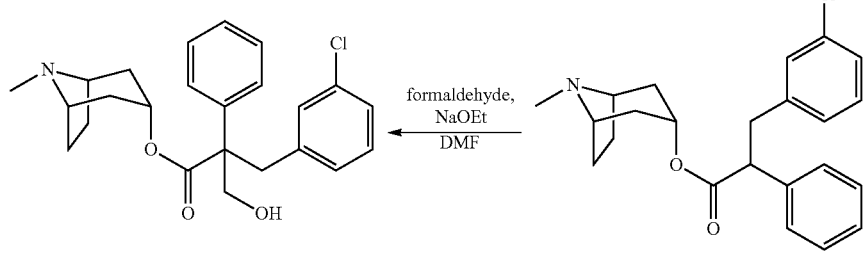

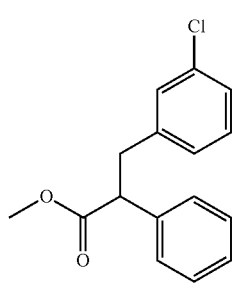 [SMILES: COC(=O)C(Cc1cccc(Cl)c1)c1ccccc1]

Methyl 3-(3-chlorophenyl)-2-phenylpropanoate

Sodium bis(trimethylsilyl)amide 1M in THF (20 mL, 20 mmol) was added dropwise to a stirred solution of methyl phenyl acetate (3.00 g, 20.0 mmol) and 3-chlorobenzyl chloride (3.16 g, 19.6 mmol) in dry THF (40 mL) under argon at −78° C., maintaining T≤−65° C. The reaction mixture was stirred for 1 H then allowed to warm to RT over 16 H. The reaction mixture was concentrated in vacuo and the residue diluted EtOAc, washed with water then brine. The organic fraction was dried (Na$_2$SO$_4$) and concentrated in vacuo to give crude product as yellow oil (5.48 g, 100%). This was used crude without purification. $^1$H NMR (400 MHz, CDCl$_3$): δ 7.32-7.26 (6H, m), 7.16-7.14 (2H, m), 7.13-7.10 (1H, m), 3.82 (1H, dd, J=6.7, 9.2 Hz), 3.61 (3H, s), 3.39 (1H, dd, J=13.6, 9.6 Hz), 2.99 (1H, dd, J=13.6, 6.8 Hz).

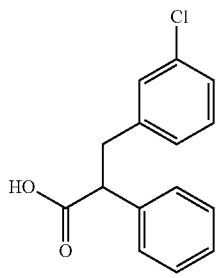 [SMILES: O=C(O)C(Cc1cccc(Cl)c1)c1ccccc1]

3-(3-Chlorophenyl)-2-phenylpropanoic acid

Methyl 3-(3-chlorophenyl)-2-phenylpropanoate (5.48 g, 20 mmol) in a mixture of THF (70 mL) and MeOH (7 mL) was treated with 2M NaOH (aq) (28.5 mL, 57 mmol) and the reaction mixture stirred at RT for 18 H. The reaction mixture was concentrated in vacuo and the residue diluted water and washed with EtOAc. The aqueous fraction was acidified with 1M HCl to pH1.0 and extracted with EtOAc. The combined organic fractions were dried (MgSO$_4$) and concentrated in vacuo to give crude product as yellow oil which crystallised on standing (3.82 g 73%). Used without purification. $^1$H NMR (400 MHz, CDCl$_3$): 7.34-7.27 (5H, m), 7.16-7.11 (3H, m), 7.00-6.96 (1H, m), 3.84 (1H, dd, J=7.0, 8.5 Hz), 3.38 (1H, dd, J=8.5, 13.9 Hz), 3.01 (1H, dd, J=7.0, 13.9 Hz).

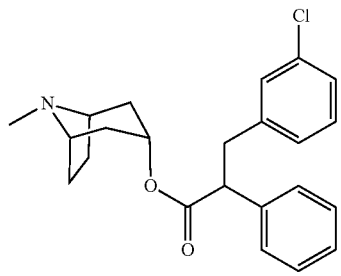 [SMILES: CN1C2CCC1CC(OC(=O)C(Cc1cccc(Cl)c1)c1ccccc1)C2]

(1R,3r,5S)-8-Methyl-8-azabicyclo[3.2.1]octan-3-yl 3-(3-chlorophenyl)-2-phenylpropanoate A stirred solution of 3-(3-chlorophenyl)-2-phenylpropanoic acid (2.0 g, 7.7 mmol) in DCM (20 mL) containing DMF (300 μL) under argon was treated dropwise at 0° C. with oxalyl chloride (955 μL, 5.9 mmol). The reaction mixture was stirred at 0° C. for 10 min then allowed to warm to RT and stirred for 18 H. The reaction mixture was concentrated in vacuo, and the residue azeotroped with toluene (2×15 mL) to give crude acid chloride. The resultant residue was stirred in dry toluene (10 mL) with (1R,3r,5S)-8-methyl-8-azabicyclo[3.2.1]octan-3-ol (1.31 g, 9.3 mmol) under argon at 100° C. for 3 H. The reaction mixture was concentrated in vacuo. The resultant residue was treated with DCM (60 mL) and water (40 mL) and basified to pH 10 with 1M NaOH (aq). The organic fraction was separated, washed with brine, dried (MgSO$_4$) and concentrated in vacuo. The residue was purified on silica (40 g, 0-10% 2M NH$_3$/MeOH in DCM) to give the title compound as a light brown oil (1.06 g, 36%). $^1$H NMR (400 MHz, CDCl$_3$): δ 7.33-7.26 (5H, m), 7.16-7.15 (3H, m), 7.03-7.00 (1H, m), 4.91 (1H, t, J=5.4 Hz), 3.75 (1H, dd, J=6.5, 9.0 Hz), 3.48 (2H, s), 3.03-2.91 (2H, m), 2.19 (3H, s), 2.07-1.94 (3H, m), 1.83-1.42 (4H, m), 1.36-1.28 (1H, m); LCMS (ESI) [M+H]$^+$ 384.1/386.1.

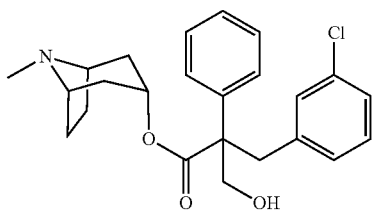 [SMILES: CN1C2CCC1CC(OC(=O)C(CO)(Cc1cccc(Cl)c1)c1ccccc1)C2]

Figure 30A:
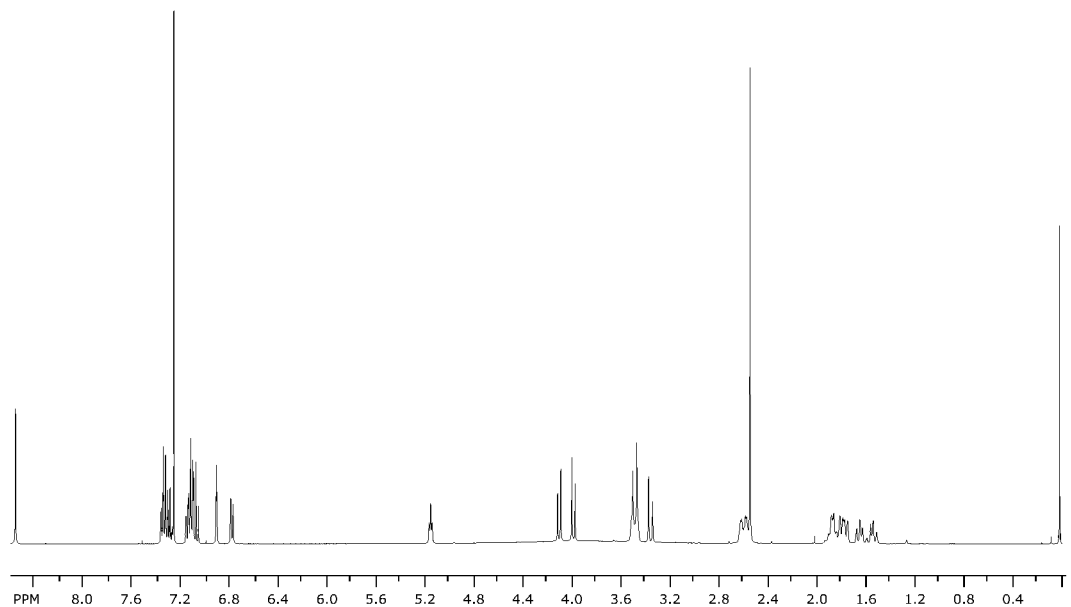
FIG. 30A is a ¹H NMR spectrum of (1R,3r,5S)-8-Methyl-8-azabicyclo[3.2.1]octan-3-yl 2-(3-chlorobenzyl)-3-hydroxy-2-phenyl propanoate.
Figure 30B:
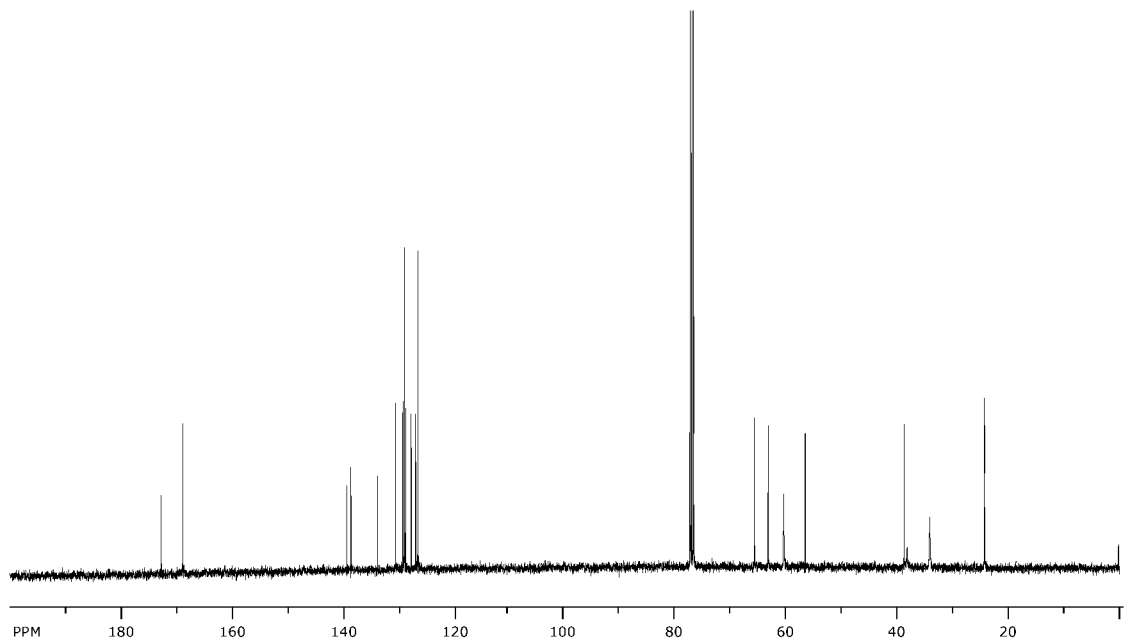
FIG. 30B is a ¹³C NMR spectrum of (1R,3r,5S)-8-Methyl-8-azabicyclo[3.2.1]octan-3-yl 2-(3-chlorobenzyl)-3-hydroxy-2-phenyl propanoate.

(1R,3r,5S)-8-Methyl-8-azabicyclo[3.2.1]octan-3-yl 2-(3-chlorobenzyl)-3-hydroxy-2-phenyl propanoate (1R,3r,5S)-8-Methyl-8-azabicyclo[3.2.1]octan-3-yl 3-(3-chlorophenyl)-2-phenylpropanoate (1.10 g, 2.9 mmol), in DMF (15 mL) was treated paraformaldehyde (1.10 g, 36.0 mmol) followed by 21% sodium ethoxide solution (30 μL, 0.006 mmol) and stirred at 100±5° C. for 24 H. The reaction mixture was diluted with DCM (50 mL) and filtered through Celite. The filtrate was concentrated in vacuo and the residue purified on silica (24 g, 0-10% 2M $NH_3$/MeOH in DCM). The product was further purified by HPLC, Kinetix Axia C18 RP col. (Long) using 10-60% $CH_3CN$ in $H_2O$ [0.1% HCOOH] over 10 min ramp @ 18 mL/min (UV=200 nm) to give product as white solid (554 mg, 50%). $^1$H NMR (400 MHz, $CDCl_3$): δ 7.38-7.27 (3H, m), 7.16-7.06 (4H, m), 6.91 (1H, t, J=1.7 Hz), 6.79 (1H, d, J=7.6 Hz), 5.16 (1H, t, J=5.0 Hz), 4.10 (1H, d, J=10.6 Hz), 3.98 (1H, d, J=10.6 Hz), 3.52-3.45 (3H, m), 3.35 (1H, d, J=13.3 Hz), 2.64-2.55 (1H, m), 2.54 (3H, s), 1.91-1.72 (4H, m), 1.68-1.48 (2H, m); LCMS (ESI) [M+H]$^+$ 414.2. The $^1$H NMR and $^{13}$C NMR spectra for the title compound are shown in FIGS. 30A and 30B respectively.

Synthetic Scheme of Example 20: (1R,3r,5S)-8-Methyl-8-azabicyclo[3.2.1]octan-3-yl 3-hydroxy-2-(4-methoxybenzyl)-2-phenyl propanoate

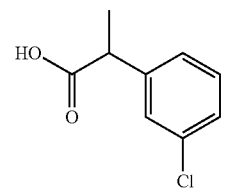

2-(3-Chlorophenyl)propanoic acid

Methyl 2-(3-chlorophenyl)propanoate (590 mg, 2.97 mmol) in THF (12 mL) and MeOH (1 mL) at RT was treated with 2N NaOH (aq) (4.2 mL, 8.41 mmol) and stirred overnight. The reaction mixture was concentrated in vacuo and the resulting aqueous layer was acidified with 1N HCl to pH 1 and extracted with EtOAc. The combined organic fractions were washed with brine, dried ($MgSO_4$) and concentrated in vacuo. The residue was purified on silica (40 g 0-30% EtOAc in cyclohexane) to give the title compound as a pale yellow oil (229 mg, 42%). $^1$H NMR (400 MHz, $CDCl_3$): δ 7.34-7.15 (4H, m), 3.72 (1H, q, J=7.3 Hz), 1.51 (3H, d, J=7.3 Hz).

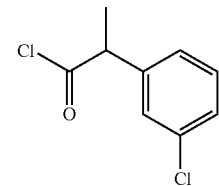

2-(3-Chlorophenyl)propanoyl chloride

A stirred solution of 2-(3-chlorophenyl)propanoic acid (229 mg, 1.24 mmol) in DCM (3 mL) containing DMF (55

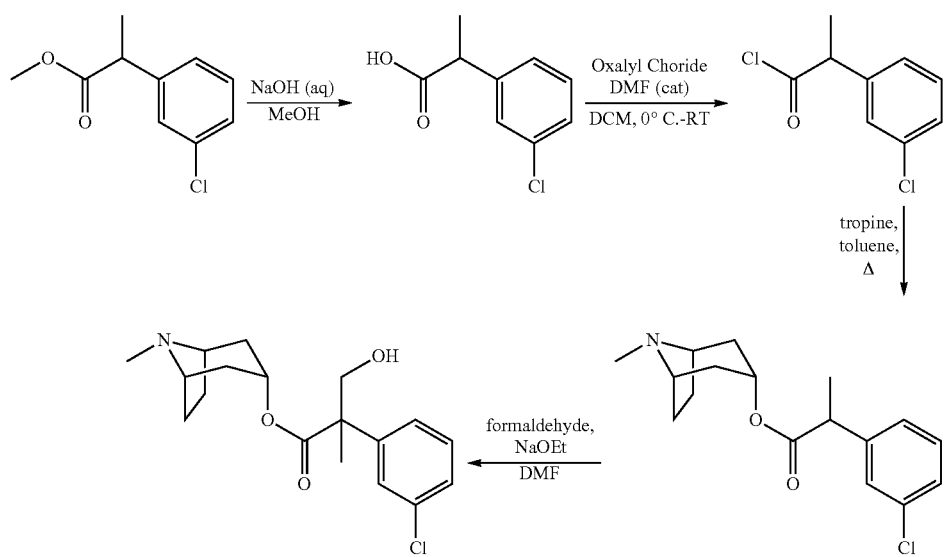

μL) was treated dropwise with oxalyl chloride (150 μL, 1.77 mmol) at 0° C., under argon. The resulting mixture was stirred at 0° C. for 30 min before being allowed to warm to RT overnight. The reaction mixture was concentrated in vacuo to give the title crude compound which was used immediately without purification.

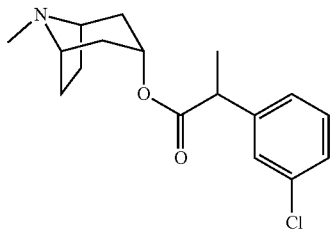 [SMILES: CC(C(=O)OC1CC2CCC(C1)N2C)c1cccc(Cl)c1]

(1R,3r,5S)-8-Methyl-8-azabicyclo[3.2.1]octan-3-yl 2-(3-chlorophenyl)propanoate

Crude 2-(3-chlorophenyl)propanoyl chloride was stirred in dry toluene (3 mL) with tropine (214 mg, 1.51 mmol) at 100° C., under argon for 3 H. The reaction mixture was concentrated in vacuo. The residue was diluted with aqueous saturated NaHCO$_3$ and extracted with EtOAc. Combined organic fractions were washed with brine, dried (MgSO$_4$) and concentrated in vacuo. The resulting residue was purified on silica (40 g 0-10% 2N NH$_3$ MeOH in DCM) to give the title compound as a yellow oil (272 mg, 71%). LCMS (ESI) [M+H]$^+$ 308.2.

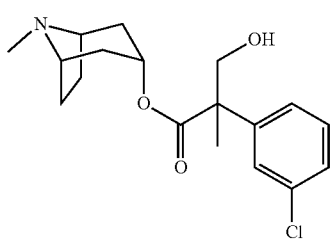 [SMILES: CN1C2CCC1CC(OC(=O)C(C)(CO)c1cccc(Cl)c1)C2]

Figure 31A:
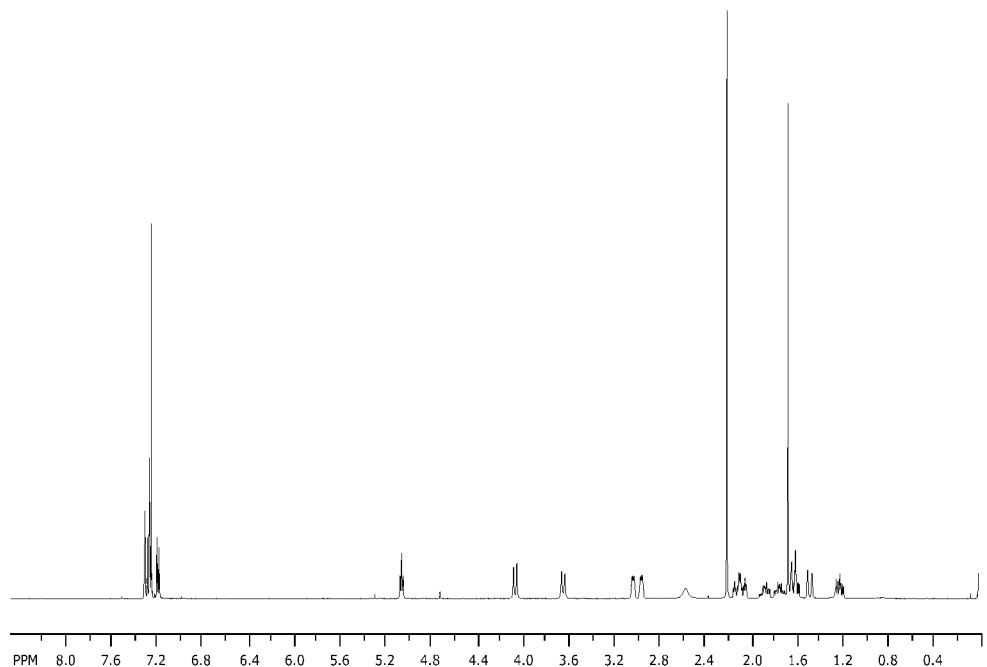
FIG. 31A is a ¹H NMR spectrum of (1R,3r,5S)-8-Methyl-8-azabicyclo[3.2.1]octan-3-yl 2-(3-chlorophenyl)-3-hydroxy-2-methyl propanoate.
Figure 31B:
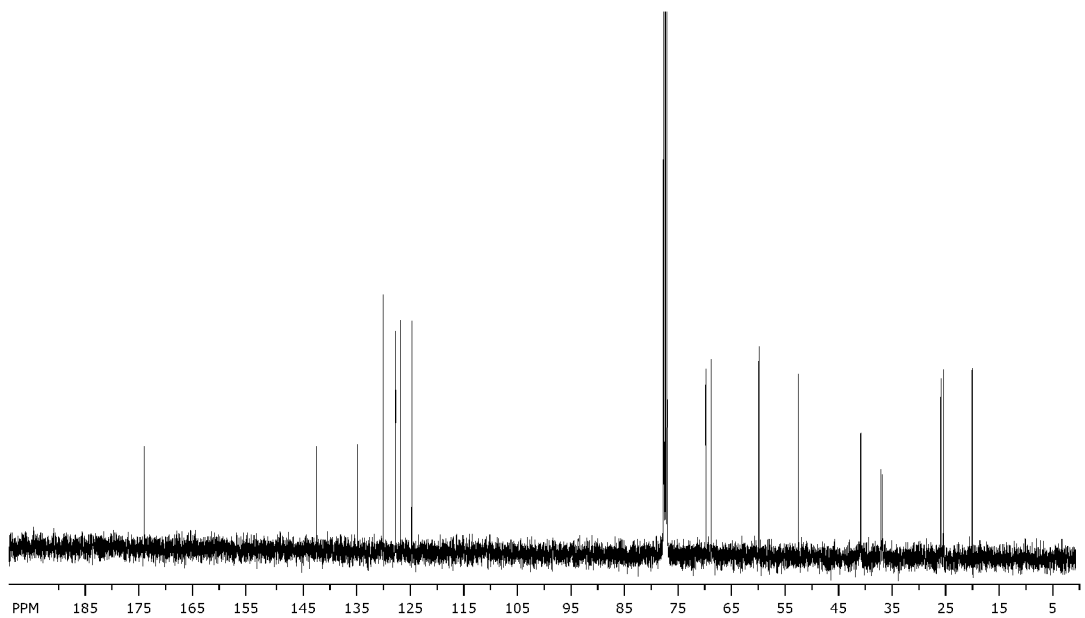
FIG. 31B is a ¹³C NMR spectrum of (1R,3r,5S)-8-Methyl-8-azabicyclo[3.2.1]octan-3-yl 2-(3-chlorophenyl)-3-hydroxy-2-methyl propanoate.

(1R,3r,5S)-8-Methyl-8-azabicyclo[3.2.1]octan-3-yl 2-(3-chlorophenyl)-3-hydroxy-2-methyl propanoate (1R,3r,5S)-8-Methyl-8-azabicyclo[3.2.1]octan-3-yl 2-(3-chlorophenyl)propanoate (337 mg, 1.09 mmol) in DMF (2.5 mL) was treated with paraformaldehyde (49 mg, 1.64 mmol) followed by 21% sodium ethoxide solution, (4.3 μL, 0.055 mmol) and the reaction mixture stirred at RT for 1 H. The reaction mixture was diluted with 1N HCl and extracted with EtOAc. The combined aqueous fractions were then basified with 1N NaOH to pH 13 and extracted with EtOAc. The combined organic fractions were washed with brine, dried (MgSO$_4$) and concentrated in vacuo. The resulting residue was purified on silica (40 g, 0-10% 2N NH$_3$ MeOH in DCM) to give the title compound as an off-white solid (193 mg, 52%). $^1$H NMR (400 MHz, CDCl$_3$): δ 7.34-7.26 (3H, m), 7.23-7.17 (1H, m), 5.06 (1H, t, J=5.4 Hz), 4.07 (1H, d, J=11.3 Hz), 4.64 (1H, d, J=11.3 Hz), 3.06-3.00 (1H, m), 2.99-2.93 (1H, m), 2.57 (1H, br s), 2.21 (3H, m), 2.16-2.03 (2H, m), 1.93-1.82 (1H, m), 1.80-1.69 (1H, m), 1.67 (3H, s), 1.66-1.56 (2H, m), 1.51-1.44 (1H, m), 1.27-1.17 (1H, m); LCMS (ESI) [M+H]$^+$ 338.12. The $^1$H NMR and $^{13}$C NMR spectra for the title compound are shown in FIGS. 31A and 31B respectively.

Synthetic Scheme of Example 21: (1R,3r,5S)-8-Methyl-8-azabicyclo[3.2.1]octan-3-yl 3-hydroxy-2-(4-methoxybenzyl)-2-phenyl propanoate

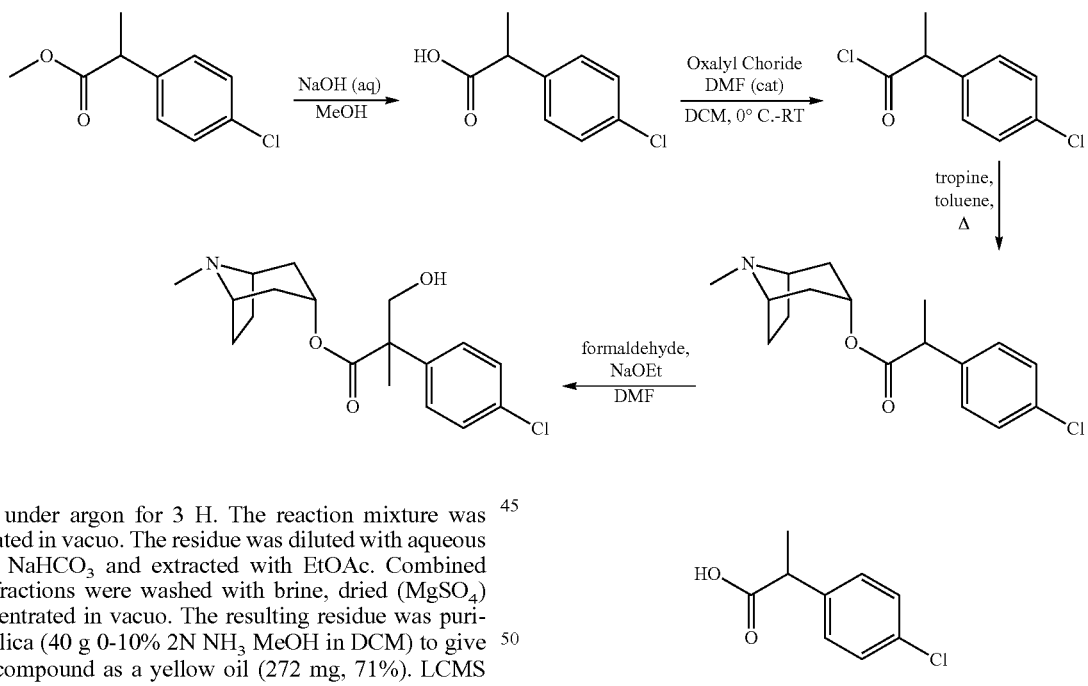

2-(4-Chlorophenyl)propanoic acid

Methyl 2-(4-chlorophenyl)propanoate (547 mg, 2.75 mmol) in THF (12 mL) and MeOH (1 mL) at RT was treated with 2N NaOH (aq) (3.9 mL, 7.79 mmol) and stirred for 8 H. The reaction mixture was concentrated in vacuo and the resulting aqueous layer acidified with 1N HCl to pH 1 and extracted with EtOAc. The combined organic fractions were washed with brine, dried (MgSO$_4$) and concentrated in vacuo. The residue was purified on silica (40 g 0-30% EtOAc in cyclo-hexane) to give the title compound as an off-white solid (137 mg, 27%). $^1$H NMR (400 MHz, CDCl$_3$): δ 7.35-7.16 (4H, m), 3.71 (1H, q, J=9.4 Hz), 1.49 (3H, d, J=9.6 Hz).

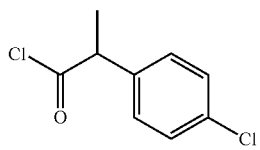

2-(4-Chlorophenyl)propanoyl chloride

A stirred solution of 2-(4-chlorophenyl)propanoic acid (265 mg, 1.44 mmol) in DCM (4 mL) containing DMF (70 µL) was treated dropwise with oxalyl chloride (180 µL, 2.05 mmol) at 0° C., under argon. The resulting mixture was stirred at 0° C. for 30 min. The reaction mixture was concentrated in vacuo to give the title crude compound and used immediately without purification.

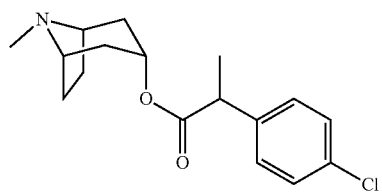 [SMILES: CC(C(=O)OC1CC2CCC(C1)N2C)c1ccc(Cl)cc1]

(1R,3r,5S)-8-Methyl-8-azabicyclo[3.2.1]octan-3-yl 2-(4-chlorophenyl)propanoate

Crude 2-(4-chlorophenyl)propanoyl chloride was stirred in dry toluene (4 mL) with tropine (247 mg, 1.75 mmol) at 100° C., under argon overnight. The reaction mixture was concentrated in vacuo. The residue was diluted with EtOAc and extracted with 1N HCl. The combined aqueous fractions were then basified with 1N NaOH to pH 13 and extracted with EtOAc. The combined organic fractions were washed with brine, dried (MgSO$_4$) and concentrated in vacuo to give the title compound as a brown oil, which was used crude in the next reaction (230 mg, 52%). LCMS (ESI) [M+H]$^+$ 308.1.

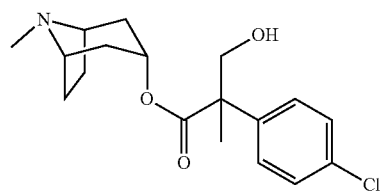 [SMILES: CN1C2CCC1CC(OC(=O)C(C)(CO)c1ccc(Cl)cc1)C2]

Figure 32A:
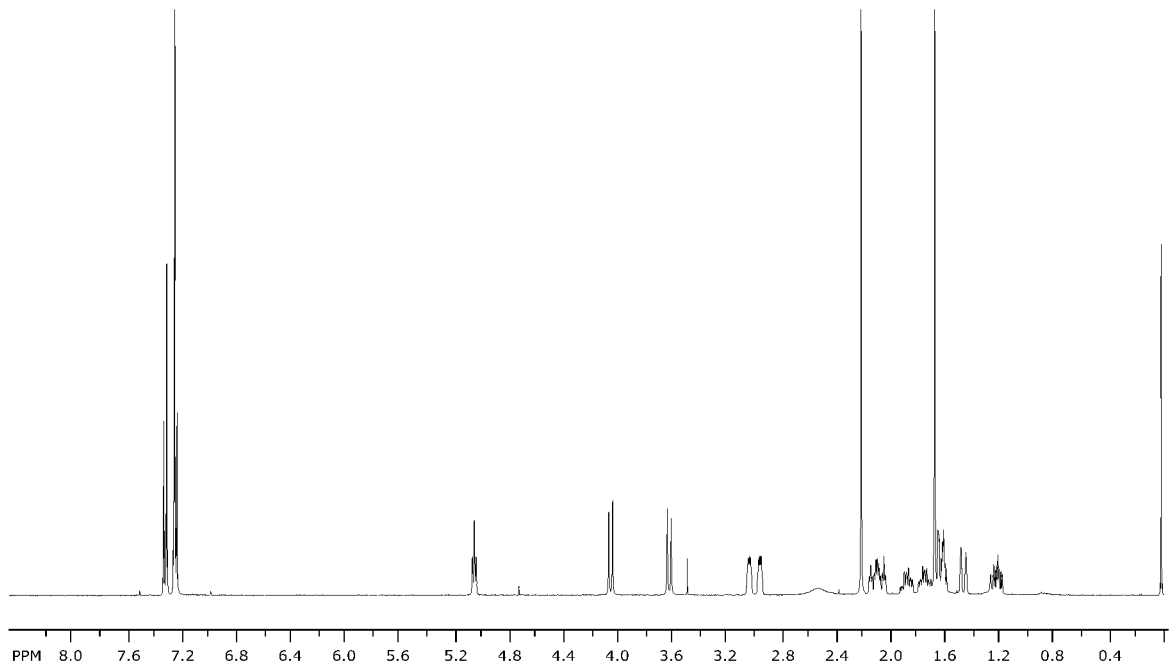
FIG. 32A is a ¹H NMR spectrum of (1R,3r,5S)-8-Methyl-8-azabicyclo[3.2.1]octan-3-yl 2-(4-chlorophenyl)-3-hydroxy-2-methyl propanoate.
Figure 32B:
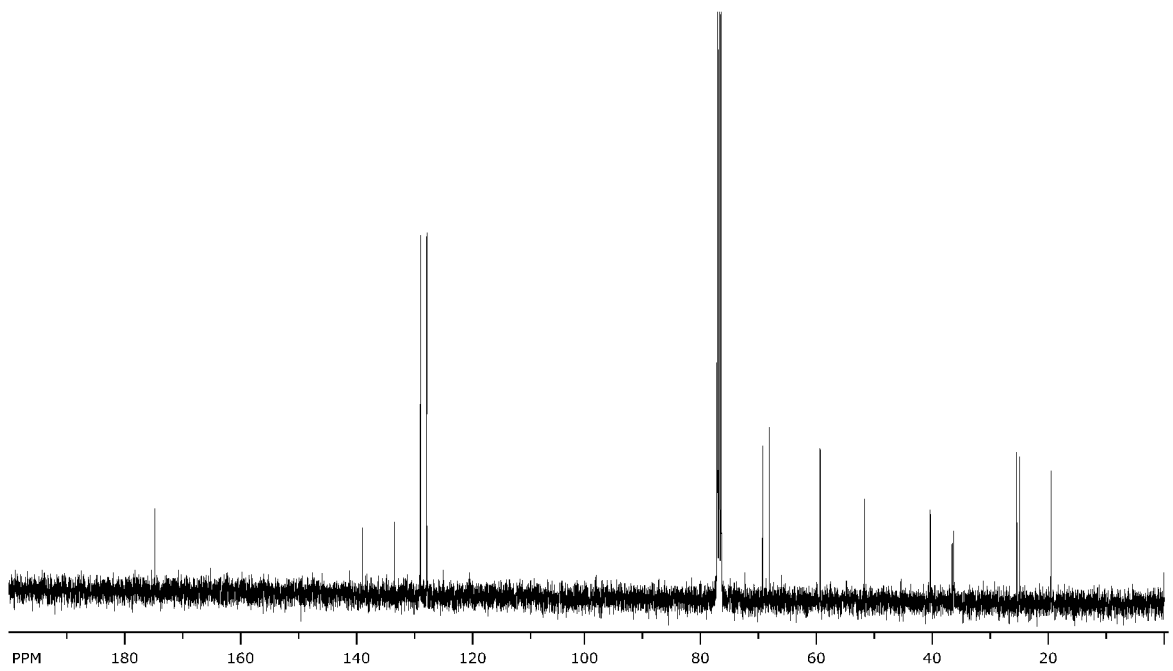
FIG. 32B is a ¹³C NMR spectrum of (1R,3r,5S)-8-Methyl-8-azabicyclo[3.2.1]octan-3-yl 2-(4-chlorophenyl)-3-hydroxy-2-methyl propanoate.

(1R,3r,5S)-8-Methyl-8-azabicyclo[3.2.1]octan-3-yl 2-(4-chlorophenyl)-3-hydroxy-2-methyl propanoate (1R,3r,5S)-8-Methyl-8-azabicyclo[3.2.1]octan-3-yl 2-(4-chlorophenyl)propanoate (230 mg, 0.75 mmol) in DMF (2 mL) was treated with paraformaldehyde (34 mg, 1.12 mmol) followed by 21% sodium ethoxide solution, (3 µL, 0.037 mmol) and the reaction mixture stirred at RT for 1 H. Further paraformaldehyde (34 mg, 1.12 mmol) followed by 21% sodium ethoxide solution, (3 µL, 0.037 mmol) were added and stirring continued at RT for 1 H. The reaction mixture was diluted with 1N HCl and extracted with EtOAc. The combined aqueous fractions were then basified with 1N NaOH to pH 13 and extracted with EtOAc. The combined organic fractions were washed with brine, dried (MgSO$_4$) and concentrated in vacuo. The resulting residue was purified on silica (40 g, 0-10% 2N NH$_3$ MeOH in DCM) to give the title compound as an off-white solid (118 mg, 47%). $^1$H NMR (400 MHz, CDCl$_3$): δ 7.36-7.31 (2H, m), 7.28-7.22 (2H, m), 5.06 (1H, t, J=5.5 Hz), 4.05 (1H, d, J=11.1 Hz), 3.62 (1H, d, J=11.1 Hz), 3.06-3.00 (1H, m), 2.99-2.92 (1H, m), 2.52 (1H, br s), 2.21 (3H, s), 2.16-2.01 (2H, m), 1.93-1.82 (1H, m), 1.80 (1H, m), 1.67 (3H, s), 1.65-1.56 (2H, m), 1.49-1.42 (1H, m), 1.25-1.15 (1H, m); LCMS (ESI). [M+H]$^+$ 338.1. The $^1$H NMR and $^{13}$C NMR spectra for the title compound are shown in FIGS. 32A and 32B respectively.

Synthetic Scheme of Example 22: (1R,3r,5S)-8-Methyl-8-azabicyclo[3.2.1]octan-3-yl 2-(4-(benzyloxy)phenyl)propanoate

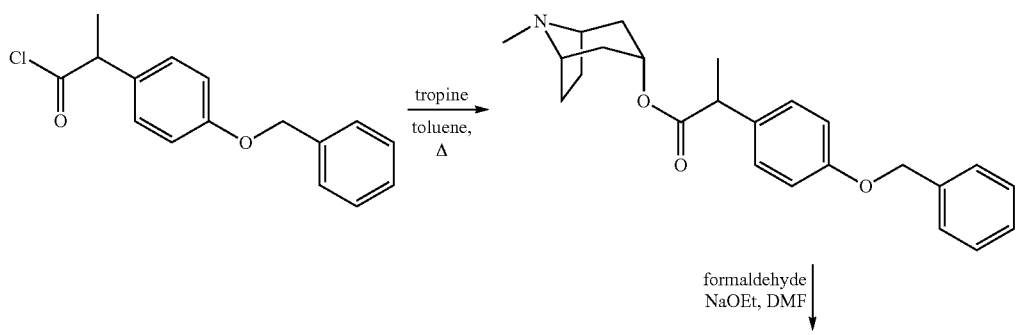

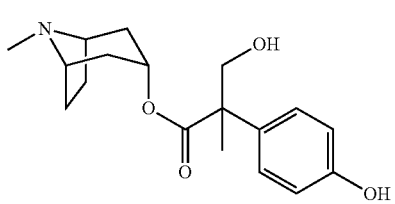 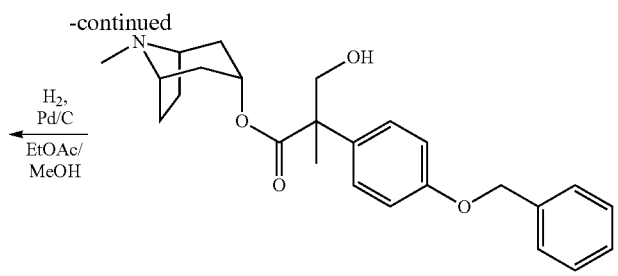

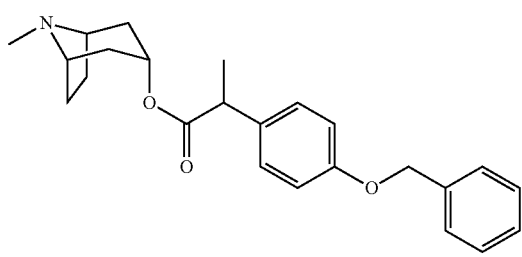 [SMILES: CC(C(=O)OC1CC2CCC(C1)N2C)c1ccc(OCc2ccccc2)cc1]

(1R,3r,5S)-8-methyl-8-azabicyclo[3.2.1]octan-3-yl 2-(4-(benzyloxy)phenyl)propanoate To a solution of 2-(4-(benzyloxy)phenyl)propanoyl chloride (1.61 g, 5.86 mmol) in toluene (20 mL) was added tropine (750 mg, 5.33 mmol) and the reaction stirred at 90° C. for 3 H, then at 50° C. for 16 H. The reaction was diluted with 1N HCl and extracted with EtOAc and the organics discarded. The combined aqueous fractions were made basic with 1N NaOH and extracted with EtOAc. The combined organic fractions were washed with brine, dried (MgSO₄) and concentrated in vacuo to give the title compound (750 mg, 37%). ¹H NMR (400 MHz, CDCl₃) δ 7.47-7.29 (5H, m), 7.23-7.19 (2H, m), 6.97-6.90 (2H, m), 5.06 (2H, s), 4.94 (1H, t, J=5.3 Hz), 3.62 (1H, q, 7.1 Hz), 3.06-3.00 (1H, m), 2.98-2.93 (1H, m), 2.22 (3H, s), 2.12-1.98 (3H, m), 1.92-1.57 (4H, m), 1.48 (3H, d, J=7.2 Hz), 1.43-1.35 (1H, m). LCMS (ESI) [M+H]⁺ 380.2, R$_t$=0.97 min (Method 2).

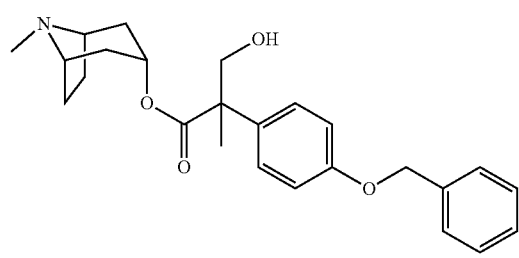 [SMILES: CN1C2CCC1CC(OC(=O)C(C)(CO)c1ccc(OCc3ccccc3)cc1)C2]

(1R,3r,5S)-8-Methyl-8-azabicyclo[3.2.1]octan-3-yl 2-(4-(benzyloxy)phenyl)-3-hydroxy-2-methyl propanoate (1R,3r,5S)-8-Methyl-8-azabicyclo[3.2.1]octan-3-yl 2-(4-(benzyloxy)phenyl)propanoate (750 mg, 1.98 mmol) in DMF (8 mL) was treated with paraformaldehyde (89 mg, 2.96 mmol) followed by 21% sodium ethoxide solution (37 µL, 0.10 mmol) and the reaction mixture stirred at RT for 1 H. The reaction mixture was diluted with EtOAc and extracted with 1N HCl. The combined aqueous fractions were made basic with 1N NaOH and extracted with EtOAc. The combined organic fractions were washed with brine, dried (MgSO₄) and concentrated in vacuo. The resulting residue was purified on silica (12 g, 0-10% MeOH in DCM) to give the title compound (685 mg, 85%). ¹H NMR (400 MHz, CDCl₃) δ 7.45-7.29 (5H, m), 7.25-7.20 (2H, m), 6.99-6.92 (2H, m), 5.06 (2H, s), 5.04 (1H, t, J=5.5 Hz), 4.09 (1H, d, J=11.1 Hz), 3.59 (1H, d, J=11.2 Hz), 3.04-2.99 (1H, m), 2.94-2.89 (1H, m), 2.50 (1H, br s), 2.20 (3H, s), 2.14-1.99 (2H, m), 1.90-1.78 (1H, m), 1.74-1.58 (6H, m), 1.49-1.41 (1H, m), 1.25-1.14 (1H, m). LCMS (ESI) [M+H]⁺ 410.2 R$_t$=0.87 min (Method 2).

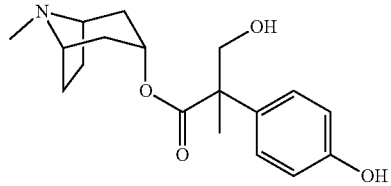 [SMILES: CN1C2CCC1CC(OC(=O)C(C)(CO)c1ccc(O)cc1)C2]

Figure 33A:
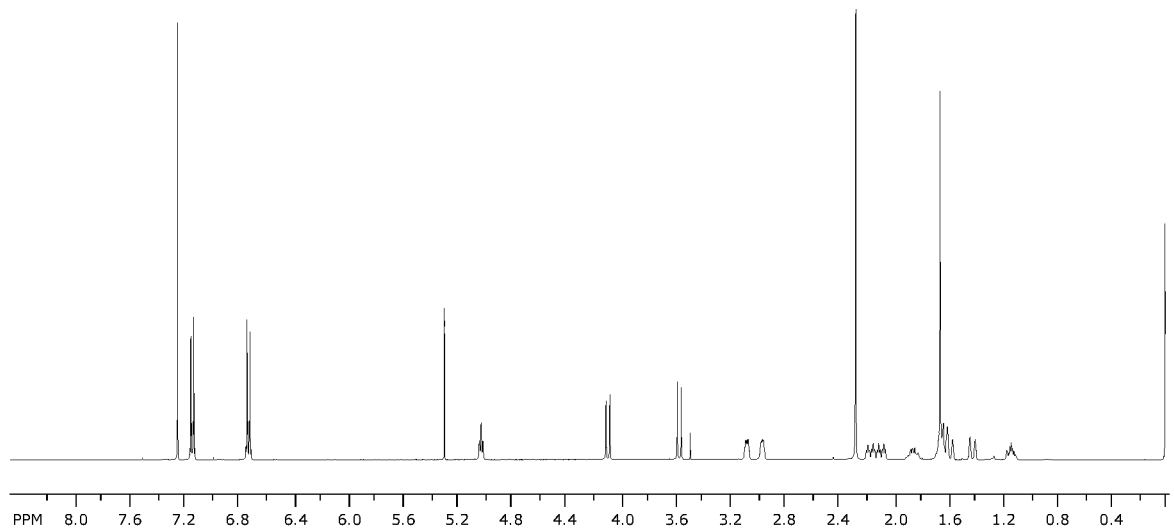
FIG. 33A is a ¹H NMR spectrum of (1R,3r,5S)-8-Methyl-8-azabicyclo[3.2.1]octan-3-yl 3-hydroxy-2-(4-hydroxyphenyl)-2-methyl propanoate.
Figure 33B:
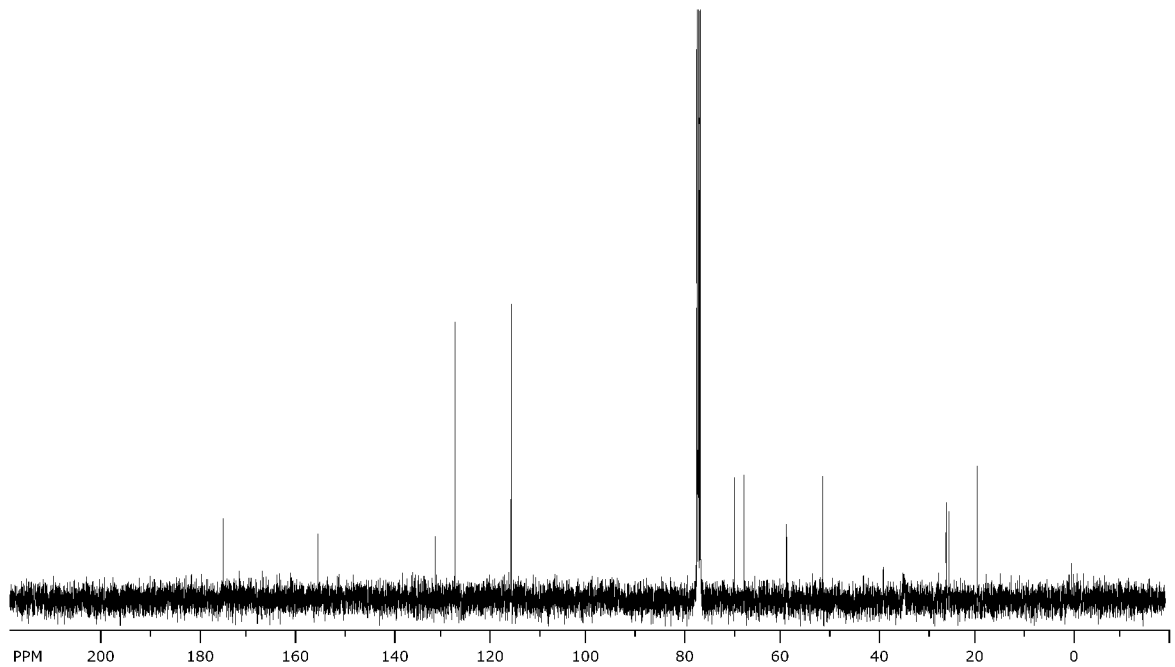
FIG. 33B is a ¹³C NMR spectrum of (1R,3r,5S)-8-Methyl-8-azabicyclo[3.2.1]octan-3-yl 3-hydroxy-2-(4-hydroxyphenyl)-2-methyl propanoate.

(1R,3r,5S)-8-Methyl-8-azabicyclo[3.2.1]octan-3-yl 3-hydroxy-2-(4-hydroxyphenyl)-2-methyl propanoate (1R,3r,5S)-8-Methyl-8-azabicyclo[3.2.1]octan-3-yl 2-(4-(benzyloxy)phenyl)-3-hydroxy-2-methylpropan-oate (685 mg, 1.67 mmol) in EtOAc (10 mL) and MeOH (3 mL) was treated with palladium on carbon (10% wt, 150 mg) and stirred at RT, under hydrogen for 16 H. The reaction mixture was filtered and the filtrate concentrated in vacuo. The residue was purified on silica (12 g, 0-10% MeOH in DCM) to give the title compound as a white solid (278 mg, 52%). ¹H NMR (400 MHz, CDCl₃): δ 7.18-7.12 (2H, m), 6.77-6.71 (2H, m), 5.03 (1H, t, J=5.1 Hz), 4.10 (1H, d, J=11.4 Hz), 3.57 (1H, d, J=11.4 Hz), 3.11-3.05 (1H, m), 3.01-2.92 (1H, m), 2.27 (3H, s), 2.17 (1H, dt, J=15.2, 4.1 Hz), 2.08 (1H, dt, J=15.3, 4.3 Hz), 1.92-1.78 (1H, m), 1.67-1.54 (6H, m), 1.41 (1H, d, J=15.3 Hz), 1.18-1.07 (1H, m); LCMS (ESI) [M+H]⁺ 320.3. The ¹H NMR and ¹³C NMR spectra for the title compound are shown in FIGS. 33A and 33B respectively.

Synthetic Scheme of Example 23: 6-Chloro-11H-benzo[e]pyrido[3,2-b][1,4]diazepine

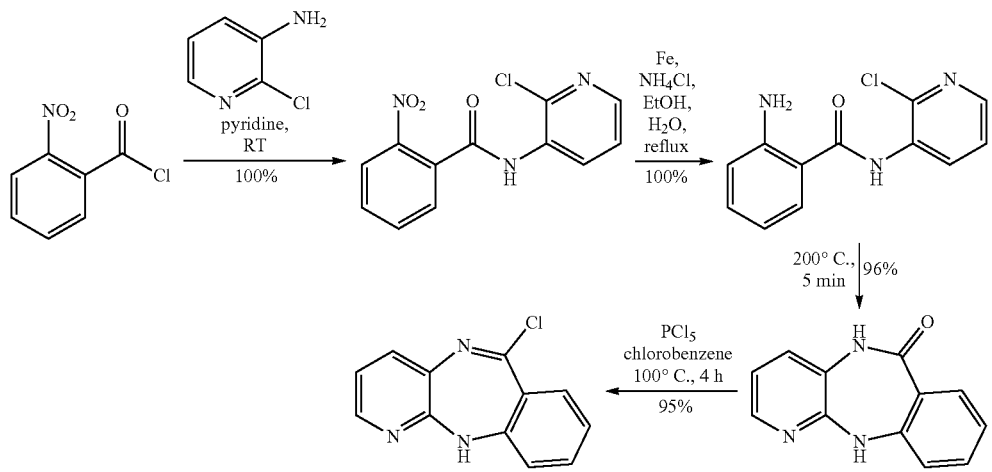

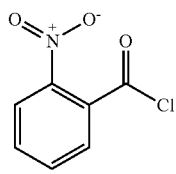

2-Nitrobenzoyl chloride

To a solution of 2-nitrobenzoic acid (5 g, 29.9 mmol) in DCM (140 mL) was added 1 drop of DMF followed by oxalyl chloride (3.7 mL, 41.9 mmol) causing effervescence. The reaction was stirred at RT for 20 min. The reaction mixture was concentrated in vacuo to give the title compound as a straw coloured oil (5.55 g, quant.). Material was used without purification. $^1$H NMR (400 MHz, CDCl$_3$): δ 8.13-8.07 (1H, m), 7.84-7.68 (3H, m).

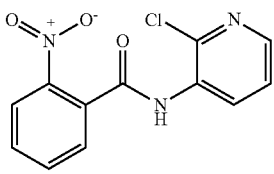

N-(2-Chloropyridin-3-yl)-2-nitrobenzamide

To a solution of 2-nitrobenzoyl chloride (5.55 g, 29.9 mmol) in THF (120 mL) was added pyridine (14.5 mL, 0.18 mol) and 3-amino-2-chloropyridine (4.23 g, 32.9 mmol) causing a precipitate to form. The reaction stirred at RT for 2 h before being diluted with 10% aq citric acid and extracted with ethyl acetate. The combined organic fractions were washed with brine, dried (MgSO$_4$) and concentrated in vacuo to give the product as a buff coloured solid (8.6 g, quant.). Material was used without purification. $^1$H NMR (400 MHz, d$_6$-DMSO) δ 10.61 (1H, s), 8.31 (1H, dd, J=4.3, 1.5 Hz), 8.25-8.16 (2H, m), 7.94-7.87 (1H, m), 7.84-7.75 (2H, m), 7.54 (1H, dd, J=8.3, 4.3 Hz).

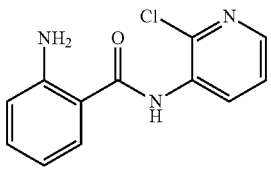 [SMILES: Nc1ccccc1C(=O)Nc1cccnc1Cl]

2-Amino-N-(2-chloropyridin-3-yl)benzamide

To a solution of N-(2-chloropyridin-3-yl)-2-nitrobenzamide (8.3 g, 29.9 mmol) in ethanol (100 mL) was added water (20 mL), iron (2.67 g, 47.8 mmol) and ammonium chloride (16 g, 0.3 mol). The mixture was heated at reflux for 40 min then diluted with water and filtered. The filtrate was extracted with ethyl acetate, the combined organic fractions washed with brine, dried (MgSO$_4$) and concentrated in vacuo to give the title product as a beige solid (7.4 g, quant.). Material was used without purification. $^1$H NMR (400 MHz, d$_6$-DMSO) δ 9.93 (1H, s), 8.29 (1H, dd, J=4.7, 1.8 Hz), 8.05 (1H, dd, J=7.9, 1.8 Hz), 7.73 (1H, dd, J=8.0, 1.5 Hz), 7.48 (1H, dd, J=7.8, 4.7 Hz), 7.24 (1H, ddd, J=8.4, 7.1, 1.5 Hz), 6.78 (1H, dd, J=8.3, 0.9 Hz), 6.61 (1H, ddd, J=8.1, 7.2, 1.1 Hz), 6.48 (2H, br s).

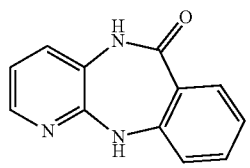 [SMILES: O=C1Nc2cccnc2Nc2ccccc21]

5,11-Dihydro-6H-benzo[e]pyrido[3,2-b][1,4]diazepin-6-one

2-Amino-N-(2-chloropyridin-3-yl)benzamide (3.5 g, 14.1 mmol) was heated at 210° C. for 5 min. Upon reaching 200° C. the reaction mixture turned black and effervescence was observed. The reaction mixture was cooled to room temperature and the solid residue washed with sat. aq. NaHCO₃ solution then DCM to give the title product as grey solid (2.89 g, 96%). Material was used without purification. $^1$H NMR (400 MHz, d$_6$-DMSO): δ 9.94 (1H, s), 8.63 (1H, s), 7.90 (1H, dd, J=4.84, 1.6 Hz), 7.72 (1H, dd, J=7.9, 1.6 Hz), 7.41-7.29 (2H, m), 7.13 (1H, dd, J=8.3, 0.8 Hz), 6.97 (1H, dd, J=7.8, 4.8 Hz), 6.95-6.89 (1H, m).

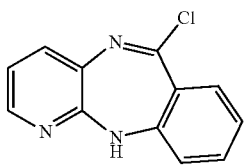 [SMILES: ClC1=Nc2cccnc2Nc2ccccc21]

6-Chloro-11H-benzo[e]pyrido[3,2-b][1,4]diazepine

A mixture of 5,11-dihydro-6H-benzo[e]pyrido[3,2-b][1,4]diazepin-6-one (500 mg, 2.37 mmol) and phosphorus pentachloride in chlorobenzene (12 mL) was heated at 100° C. for 4 h. The reaction mixture was cooled to ~4° C., isohexane (10 mL) added and solids filtered off. The solid was washed with further isohexane (10 mL) and dried in vacuo to give the product as a yellow solid (520 mg, 95%). Material was used without purification. $^1$H NMR (400 MHz, CDCl₃): δ 9.96 (1H, s), 7.72-7.59 (3H, m), 7.41 (1H, td, J=8.0, 1.3 Hz), 7.16-7.04 (3H, m).

6-Chloro-11H-benzo[e]pyrido[3,2-b][1,4]diazepine obtained in Example 23 can be used to prepare a pirenzepine of formula (II) of the invention according to the following reaction scheme

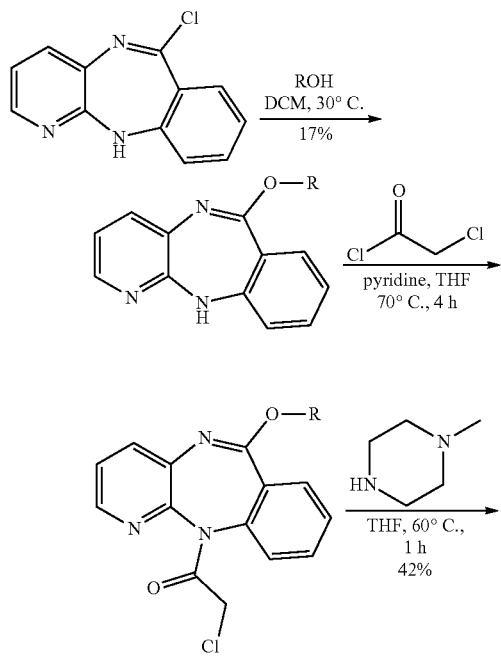

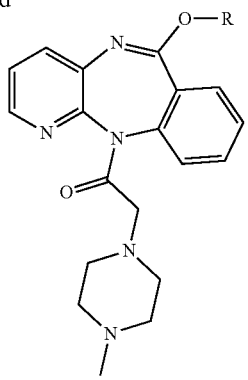

in which R can be hexyl.

Example 24

Human Muscarinic Receptor ASSAY

I. Assay Protocol M₁-M₅

M₁

Cell membrane homogenates (45 μg protein) are incubated for 60 min at 22° C. with 2 nM [3H]pirenzepine in the absence or presence of the test compound in a buffer containing 50 mM Tris-HCl (pH 7.4), 120 mM NaCl, 5 mM KCl, 5 mM MgCl₂ and 1 mM EDTA. Nonspecific binding is determined in the presence of 1 μM atropine. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is pirenzepine, which is tested in each experiment at several concentrations to obtain a competition curve from which its K$_i$ and IC₅₀ are calculated.

M₂

Cell membrane homogenates (60 μg protein) are incubated for 60 min at 22° C. with 2 nM [3H]AF-DX 384 in the absence or presence of the test compound in a buffer containing 50 mM Tris-HCl (pH 7.4), 120 mM NaCl, 5 mM KCl, 5 mM MgCl2 and 1 mM EDTA. Nonspecific binding is determined in the presence of 1 μM atropine. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is methoctramine, which is tested in each experiment at several concentrations to obtain a competition curve from which its K$_i$ and IC₅₀ are calculated.

M₃

Cell membrane homogenates (8 μg protein) are incubated for 60 min at 22° C. with 0.2 nM [3H]4-DAMP in the absence or presence of the test compound in a buffer containing 10 mM Tris-HCl (pH 7.4) and 2 mM EDTA.

Nonspecific binding is determined in the presence of 1 μM atropine. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is 4-DAMP, which is tested in each experiment at several concentrations to obtain a competition curve from which its $K_i$ and $IC_{50}$ are calculated.

$M_4$

Cell membrane homogenates (16 μg protein) are incubated for 60 min at 22° C. with 0.2 nM [3H]4-DAMP in the absence or presence of the test compound in a buffer containing 10 mM Tris-HCl (pH 7.4) and 2 mM EDTA. Nonspecific binding is determined in the presence of 1 μM atropine. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is 4-DAMP, which is tested in each experiment at several concentrations to obtain a competition curve from which its $K_i$ and $IC_{50}$ are calculated.

$M_5$

Cell membrane homogenates (15 μg protein) are incubated for 60 min at 22° C. with 0.3 nM [3H]4-DAMP in the absence or presence of the test compound in a buffer containing 10 mM Tris-HCl (pH 7.4) and 2 mM EDTA. Nonspecific binding is determined in the presence of 1 μM atropine. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is 4-DAMP, which is tested in each experiment at several concentrations to obtain a competition curve from which its $K_i$ and $IC_{50}$ are calculated.

II. Binding Affinity $M_1$-$M_5$

The results of Human muscarinic receptor assay of some compounds of the invention are shown in Table below.

| Compounds | Assay: $K_i$ (nM) | | | | |
|---|---|---|---|---|---|
| | $M_1$ | $M_2$ | $M_3$ | $M_4$ | $M_5$ |
| (structure 1) | 3.4 | 6.8 | 1 | 0.58 | 0.6 |
| (structure 2) | 3.5 | 15 | 2.9 | 0.48 | 0.71 |
| (structure 3) | 3.1 | 11 | 2 | 0.58 | 0.68 |
| (structure 4) | 19 | 72 | 13 | 7.4 | 8.5 |

-continued
| Compounds | Assay: $K_i$ (nM) | | | | |
|---|---|---|---|---|---|
| | $M_1$ | $M_2$ | $M_3$ | $M_4$ | $M_5$ |
| 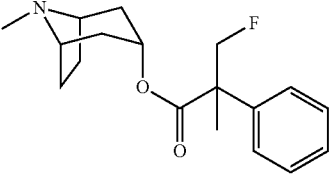 [SMILES: CN1C2CCC1CC(OC(=O)C(C)(CF)c1ccccc1)C2] | 27 | 110 | 14 | 5.8 | 7.2 |
| 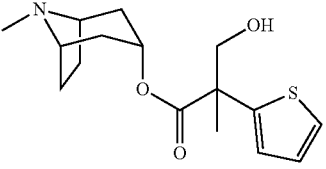 [SMILES: CN1C2CCC1CC(OC(=O)C(C)(CO)c1cccs1)C2] | 2.5 | 7.9 | 0.78 | 0.39 | 0.71 |
| 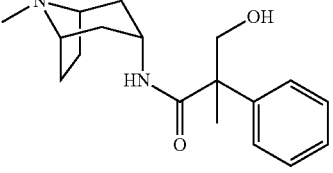 | 230 | <50% @ 1 μM | 150 | 83 | 52 |
| 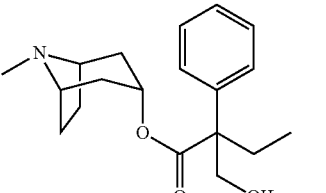 | 4.4 | 35 | 1.3 | 0.71 | 1.1 |
| 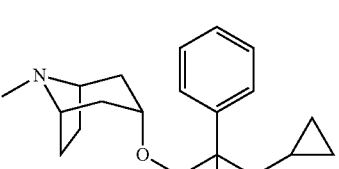 | 3.4 | 39 | 1.3 | 0.57 | 0.99 |
| 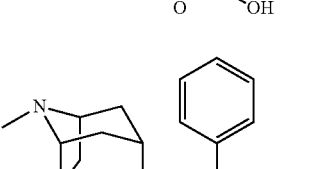 | 8.2 | 240 | 2.0 | 1.7 | 1.9 |
| 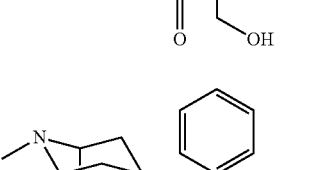 | 17 | 54 | 4.1 | 3.0 | 4.5 |

-continued

| Compounds | Assay: $K_i$ (nM) | | | | |
|---|---|---|---|---|---|
| | $M_1$ | $M_2$ | $M_3$ | $M_4$ | $M_5$ |
| [structure: N-methyl tropane ester with diphenyl, CH2OH] | 600 | <50% @ 1 µM | <50% @ 1 µM | 230 | 280 |
| [structure: N-methyl tropane ester with phenyl and 4-F-benzyl, CH2OH] | 300 | <50% @ 1 µM | 310 | 200 | 160 |
| [structure: N-methyl tropane ester with phenyl and 4-OMe-benzyl, CH2OH] | 570 | <50% @ 1 µM | 610 | <50% @ 1 µM | 320 |

Results showing an inhibition or stimulation higher than 50% are considered to represent significant effects of the test compounds The compounds of the present invention and pharmaceutically acceptable salts thereof may be in combination with one or more pharmaceutical carriers to form various types of formulations for delivery. For example, topical formulations can be used and can include ophthalmically acceptable preservatives, surfactants, viscosity enhancers, buffers, sodium chloride, and water to form aqueous ophthalmically compatible solutions and suspensions. Suitable topical formulations are described in review articles, e.g., "Recent Advances in Topical Ocular Drug Delivery", by V. K. Yellepeddi and S. Palakurthi (J. Ocul. Pharmacol. Ther. 2016, 32(2):67-82), herein incorporated by reference in its entirety. Systemic formulations (for example, orally ingested tablets) and formulations for intraocular injection are also contemplated. (pharmaceutically acceptable carriers) Examples of suitable pharmaceutically acceptable carriers are described in Remington's Pharmaceutical Sciences, Mack Publishing Company (herein incorporated by reference in its entirety), a standard reference text in the pharmaceutical field.

The specific type of formulation selected will depend on various factors, such as the compound or its salt being used, the dosage frequency, the location of the disease being treated, the chosen route of administration, and the standard pharmaceutical practice. Topical ophthalmically compatible aqueous solutions, suspensions, ointments, and gels are the preferred dosage forms for the treatment of ocular diseases in the front of the eye (the cornea, iris, trabecular meshwork); or ocular diseases of the back of the eye if the compound can be formulated such that it can be delivered topically and is able to penetrate the tissues in the front of the eye. A compound according to formula (I) will normally be contained in these formulations in an amount from about 0.01 to about 10.0 weight/percent. Preferable concentrations for topical administration range from about 0.1 to about 5.0 weight/percent. Thus, for topical administration, these formulations are delivered to the surface of the eye one to six times a day, depending on the routine discretion of the skilled clinician. Systemic administration, for example, in the form of tablets is useful for the treatment of ocular disease particularly of the back of the eye, for example, the retina.

The compounds of the present invention are preferably incorporated into ophthalmically compatible formulations for delivery to the eye. The compounds may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an ophthalmologically acceptable surfactant to assist in dissolving the compound. Furthermore, the ophthalmic solution may contain an agent to increase viscosity such as hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle such as mineral oil, liquid lanolin, or white petrolatum. Sterile ophthalmic gel formulations may be prepared by suspending the compound in a hydrophilic base prepared from the combination of, for example, carbopol-974, or the like, according to the published formulations for analogous ophthalmic formulations; preservatives and tonicity agents can be incorporated.

The pharmaceutical compositions may include one or more buffering agent(s) or pH adjusting agent(s) to provide improved pH control. In certain topical embodiments, a pharmaceutical composition of the invention has a pH between 5.0 and 8.0, between 5.0 and 7.0, between 6.0 and 8.0, or between 6.0 and 7.0. In one embodiment, the pH of a pharmaceutical composition of the invention is about 6.3 to about 7.3. In a specific embodiment, an aqueous pharmaceutical composition of the invention has an approximately neutral pH of about 6.8.

Other contemplated excipients, which may be utilized in the pharmaceutical compositions of the invention include, for example, antimicrobial agents, antioxidants, antistatic agents, lipids such as phospholipids or fatty acids, steroids such as cholesterol, protein excipients such as serum albumin (human serum albumin), recombinant human albumin, gelatin, casein, salt-forming counterions such sodium and the like. These and additional known pharmaceutical excipients and/or additives suitable for use in the formulations of the invention are known in the art, e.g., as listed in "The Handbook of Pharmaceutical Excipients, 4th edition, Rowe et al., Eds., American Pharmaceuticals Association (2003), and Remington: the Science and Practice of Pharmacy, $21^{st}$ edition, Gennaro, Ed., Lippincott Williams & Wilkins (2005).

In another aspect, the present invention provides a pharmaceutical composition comprising: (1) a compound of the present invention, a pharmaceutically acceptable salt thereof, a pharmaceutically acceptable and a pharmaceutically acceptable carrier. In an embodiment, the composition comprises a therapeutically effective amount of, preferably from about 0.01 to about 10.0 weight percent, more preferably from about 0.01 to about 5 weight/volume percent of or from about 0.1 to 5.0 weight percent of, (a) said compound and/or (b) said pharmaceutically acceptable salt. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

In another embodiment of the present invention, the pharmaceutical compositions are tablets or gelatin capsules comprising the active ingredient together with one or more of:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol: for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and
e) absorbents, colorants, flavors and sweeteners.

Tablets may be either film coated or enteric coated according to methods known in the art.

The pharmaceutical compositions of the invention may include an additional therapeutic agent in addition to compounds of the present invention. Further therapeutic agents may include, for instance, other compounds and antibodies useful for treating ocular diseases.

Pharmaceutical compositions of the invention can be administered to a patient. As used herein, the term "subject" or "patient" refers to human and non-human mammals, including but, not limited to, primates, rabbits, pigs, horses, dogs, cats, sheep, and cows. Preferably, a subject or patient is a human.

Various delivery methods for administration of the pharmaceutical compositions are contemplated and may include, for example, topical, intravitreal, oral, IV, intracameral, and other methods known to those of skill in the art.

In one embodiment, administration will typically be via a syringe. Thus the invention provides a delivery device (e.g. a syringe) including a pharmaceutical composition of the invention (e.g., pre-filled syringe). Patients will receive an effective amount of a compound according to formula (I) as the principal active ingredient.

In yet another embodiment, ocular inserts or films are used to deliver a compound of the present invention. In one such embodiment, a compound of formula (I) is formulated in a polymeric ocular insert comprising one or more mucoadhesive polymers that are biocompatible with the ocular surface and tear film of the eye. In certain embodiments, upon insertion of the polymeric eye insert in the cul-de-sac of the eye, the thickness of the tear film may increase for at least 30 minutes post-insertion. The one or more mucoadhesive polymers may be selected from the group comprising: hyaluronic acid (in acid or salt form), hydroxypropylmethylcellulose (HPMC), methylcellulose, tamarind seed polysaccharide (TSP), guar, hydroxypropyl guar (HP guar), scleroglucan poloxamer, poly(galacturonic) acid, sodium alginate, pectin, xanthan gum, xyloglucan gum, chitosan, sodium carboxymethylcellulose, polyvinyl alcohol, polyvinyl pyrrolidine, carbomer, polyacrylic acid and combinations thereof. In an embodiment of the present disclosure, the one or more mucoadhesive polymers may be HP guar, hyaluronic acid, and sodium hyaluronate.

The invention further provides a method for delivering a compound according to formula (I) to a patient, comprising a step of administering to the patient a pharmaceutical composition of the invention one or more times daily.

As used herein, all percentages are percentages by weight, unless stated otherwise. Unless otherwise indicated, the terms "a" and "an" are taken to mean "one", "at least one" or "one or more". Unless otherwise required by context, singular terms used herein shall include pluralities and plural terms shall include the singular. For clarity, the contents of any patents, patent applications, and references cited throughout this specification are hereby incorporated by reference in their entireties.

FORMULATION EXAMPLES

The following examples are included to demonstrate embodiments of the present invention. Those of skill in the art will appreciate that changes to the specific embodiments described herein can be made and still obtain a like result without departing from the spirit and scope of the invention.

Formulation Example 1—Topical Ophthalmic Preparation

| Ingredients | Concentration (w/v %) |
|---|---|
| Compound of formula (I) | 0.01-2% |
| Hydroxypropyl methylcellulose | 0.5% |
| Dibasic sodium phosphate (anhydrous) | 0.7% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein. The claims should not be read as limited to the described order or elements unless stated to that effect. It should be understood that various changes in form and detail may be made without departing from the scope of the appended claims.

What is claimed is:

1. A compound or a pharmaceutically acceptable salt thereof, wherein the compound is presented by formula (II):

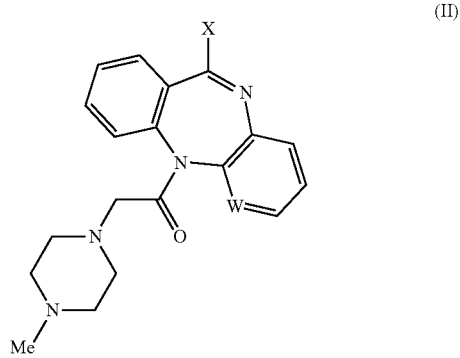

(II)

wherein
Me=$CH_3$;
W=N or CH;
X=—O—Y—Z, —S—Y—Z, or —$NR_5$—Y—Z;
$R_5$=H or $C_1$-$C_{20}$ straight or branched alkyl groups, $C_1$-$C_{10}$ straight or branched haloalkyl groups;
Y is a bivalent radical having the following meaning:
a) straight or branched $C_1$-$C_{20}$ alkyl, being optionally substituted with one or more of the substituents selected from the group consisting of: halogen atoms and hydroxyl;
b) —C(O)($C_1$-$C_{10}$ alkyl)- or —C(O)($CH_2$)$_n$C(O)O—($C_1$-$C_{10}$ alkyl)- or —($C_1$-$C_{10}$ alkyl)—;

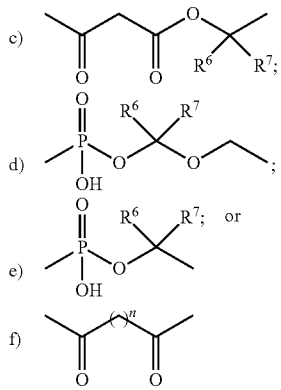

wherein n is an integer from 0 to 20;
$R_6$ and $R_7$ are independently H or $C_1$-$C_{10}$, straight or branched alkyl groups, $C_1$-$C_{10}$ straight or branched haloalkyl groups;
and
Z is H, —OH, $C_{1-6}$ alkoxy, —COOH.

2. A pharmaceutical composition comprising: (1) a compound of claim 1 and/or a pharmaceutically acceptable salt thereof; and (2) one or more pharmaceutically acceptable carriers.

3. The composition according to claim 2, wherein said composition is an ophthalmically compatible composition.

4. The composition according to claim 3, wherein said composition comprises a therapeutically effective amount of said compound, and/or said pharmaceutically acceptable salt.

5. The composition according to claim 3, wherein said composition comprises from about 0.01 to about 10.0 weight percent of said compound and/or said pharmaceutically acceptable salt.

6. The composition according to claim 3, wherein said composition comprises: from about 0.01 percent weight/volume to about 5 weight/volume percent of said compound and/or said pharmaceutically acceptable salt; or from about 0.1 to 5.0 weight percent of said compound and/or said pharmaceutically acceptable salt.

7. The composition according to claim 2, wherein said composition is a topical composition.

8. The composition according to claim 3, wherein said composition is a topical composition.

9. The composition according to claim 4, wherein said composition is a topical composition.

10. The composition according to claim 5, wherein said composition is a topical composition.

11. The composition according to claim 6, wherein said composition is a topical composition.

12. A method of treating a mammalian subject having or at risk of having an ocular disorder, said method comprising administering to the subject an effective amount of: (a) a compound according to claim 1 and/or (b) a pharmaceutically acceptable salt thereof.

13. A combination comprising: (1) a therapeutically effective amount of a compound according to claim 1 and/or a pharmaceutically acceptable salt thereof; and (2) one or more therapeutically active agents.

* * * * *